(12) United States Patent
Oost et al.

(10) Patent No.: US 9,475,779 B2
(45) Date of Patent: Oct. 25, 2016

(54) SUBSTITUTED BICYCLIC DIHYDROPYRIMIDINONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Thorsten Oost, Biberach an der Riss (DE); Ralf Anderskewitz, Laupheim (DE); Christian Gnamm, Biberach an der Riss (DE); Holger Hoesch, Biberach an der Riss (DE); Gerd Morschhaeuser, Biberach an der Riss (DE); Stefan Peters, Biberach an der Riss (DE); Uwe Joerg Ries, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/809,307

(22) Filed: Jul. 27, 2015

(65) Prior Publication Data
US 2016/0031829 A1    Feb. 4, 2016

(30) Foreign Application Priority Data
Jul. 31, 2014  (EP) .................... 14179288

(51) Int. Cl.
C07D 239/70   (2006.01)
A61K 31/517   (2006.01)
C07D 401/04   (2006.01)

(52) U.S. Cl.
CPC .......... *C07D 239/70* (2013.01); *C07D 401/04* (2013.01)

(58) Field of Classification Search
None
See application file for complete search history.

(56) References Cited

U.S. PATENT DOCUMENTS

| | | | |
|---|---|---|---|
| 8,580,800 B2 | 11/2013 | Von Nussbaum et al. | |
| 8,889,700 B2 | 11/2014 | Von Nussbaum et al. | |
| 9,040,516 B2 | 5/2015 | Shiro et al. | |
| 9,290,459 B1 * | 3/2016 | Gnamm | C07D 403/12 |
| 2009/0093477 A1 | 4/2009 | Ray et al. | |
| 2010/0010024 A1 | 1/2010 | Von Nussbaum et al. | |
| 2011/0034433 A1 | 2/2011 | Von Nussbaum et al. | |
| 2012/0004203 A1 | 1/2012 | Von Nussbaum et al. | |
| 2012/0094968 A1 | 4/2012 | Von Nussbaum et al. | |
| 2013/0065913 A1 | 3/2013 | Blench et al. | |
| 2014/0221335 A1 | 8/2014 | Gnamm et al. | |

FOREIGN PATENT DOCUMENTS

| | | |
|---|---|---|
| CA | 2656307 A1 | 1/2008 |
| DE | 102006031314 A1 | 1/2008 |
| DE | 102007061766 A1 | 6/2009 |
| DE | 102009004197 A1 | 7/2010 |
| GB | 2392910 A | 3/2004 |
| WO | 03053930 | 7/2003 |
| WO | 2004020410 A2 | 3/2004 |
| WO | 2004020412 A1 | 3/2004 |
| WO | 2004024700 A1 | 3/2004 |
| WO | 2004024701 A1 | 3/2004 |
| WO | 2005082863 A2 | 9/2005 |
| WO | 2005082864 A1 | 9/2005 |
| WO | 2006082412 A2 | 8/2006 |

(Continued)

OTHER PUBLICATIONS

International Search Report and Written Opinion for corresponsing application, PCT/EP2015/067501, date of mailing Sep. 24, 2015.

(Continued)

*Primary Examiner* — Emily Bernhardt
(74) *Attorney, Agent, or Firm* — Michael P. Morris; Edward S. Lazer

(57) ABSTRACT

Substituted bicyclic dihydropyrimidinones of formula 1

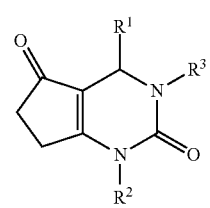

which are inhibitors of neutrophil elastase and useful as medicaments for the treatment of, inter alia, COPD. An exemplary compound is:

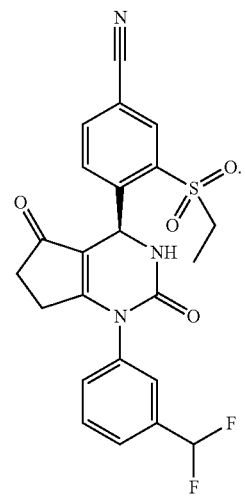

14 Claims, No Drawings

(56) References Cited

FOREIGN PATENT DOCUMENTS

| | | |
|---|---|---|
| WO | 2006136857 A1 | 12/2006 |
| WO | 2007129060 A1 | 11/2007 |
| WO | 2008135537 A1 | 11/2008 |
| WO | 2009013444 A1 | 1/2009 |
| WO | 2009037413 A1 | 3/2009 |
| WO | 2009060158 A1 | 5/2009 |
| WO | 2009060203 A1 | 5/2009 |
| WO | 2009060206 A1 | 5/2009 |
| WO | 2009080199 A1 | 7/2009 |
| WO | 2009135599 A1 | 11/2009 |
| WO | 2010078953 A1 | 7/2010 |
| WO | 2010115548 A1 | 10/2010 |
| WO | 2011110858 A1 | 9/2011 |
| WO | 2011110859 A1 | 9/2011 |
| WO | 2012002502 A1 | 1/2012 |
| WO | 2013018804 A1 | 2/2013 |
| WO | 2014009425 A1 | 1/2014 |
| WO | 2014029830 A1 | 2/2014 |
| WO | 2014029831 A1 | 2/2014 |
| WO | 2014029832 A1 | 2/2014 |
| WO | 2014035414 A1 | 3/2014 |
| WO | 2014122160 A1 | 8/2014 |

OTHER PUBLICATIONS

Abstract in English for DE102007061766, Jun. 25, 2009.
Abstract in English for WO2012002502, May 1, 2012.
Sjo et al., "Neutrophil elastase inhibitors: recent advances in the development of mechanism-based and nonelectrophilic inhibitors", Future Medicinal Chemistry, vol. 4, 2012, p. 651-660.

* cited by examiner

SUBSTITUTED BICYCLIC DIHYDROPYRIMIDINONES AND THEIR USE AS INHIBITORS OF NEUTROPHIL ELASTASE ACTIVITY

This invention relates to substituted bicyclic dihydropyrimidinones of formula 1

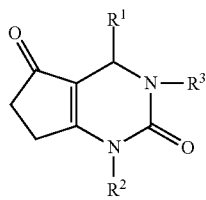

1 and their use as inhibitors of neutrophil elastase activity, pharmaceutical compositions containing the same, and methods of using the same as agents for treatment and/or to prevention of pulmonary, gastrointestinal and genitourinary diseases, inflammatory diseases of the skin and the eye and other autoimmune and allergic disorders, allograft rejection, and oncological diseases.

BACKGROUND INFORMATION

The following references describe neutrophil elastase inhibitors with a monocyclic dihydro-pyrimidinone core: GB2392910, WO04024700, WO05082864, WO05082863, DE102006031314, U.S. Ser. No. 10/001,0024, WO10115548, WO09080199, DE102007061766, WO06136857, WO06082412, WO12002502.

The following references describe neutrophil elastase inhibitors with a bicyclic tetra-hydropyrrolopyrimidinedione core: WO07129060, WO08135537, U.S. Ser. No. 09/009,3477, WO09013444, WO09060206, WO09060203, WO09060158, U.S. Ser. No. 11/003,4433.

The following references describe neutrophil elastase inhibitors with core structures other than those herein before mentioned: WO04020412, WO04020410, WO03053930, WO10078953, WO09135599, DE102009004197, WO11110858, WO11110859, WO09060158, WO009037413, WO004024701, U.S. Ser. No. 13/006,5913, WO13018804, WO12002502, US 2014/0171414, WO14009425, WO2014029831, WO2014029832 and WO2014029830, WO14122160, WO14135414.

For a review on various inhibitors of neutrophil elastase see: P. Sjö (*Future Med. Chem.* 2012, 4, 651-660).

BRIEF SUMMARY OF THE INVENTION

Neutrophil elastase (NE) is a 29 kDa serine protease. It is expressed in bone marrow precursor cells, stored in the granula of peripheral blood granulocytes at high concentrations and it is released upon cellular activation. To the substrates of NE belong major elements of the extracellular matrix (ECM): elastin, fibronectin, laminin, collagen and proteoglycans. Neutrophil elastase activity leads to ECM degradation, increases migration and chemotaxis of monocytes and vascular smooth muscle cells and directly affects components of the coagulation and fibrinolytic pathways (PAI-1 and TFPI). Increased activity of neutrophil elastase is associated with chronic inflammatory and fibrotic diseases of several organs. The potential of neutrophil elastase inhibitors as is anti-inflammatory therapies has been reviewed by P. A. Henriksen in *Current Opinion in Hematology* 2014, 21, 23-28. Inhibitors of neutrophil elastase will therefore have an important role for the treatment of different diseases like COPD, idiopathic pulmonary fibrosis and other fibrotic diseases, cancer, acute lung injury, acute respiratory distress syndrome, bronchiectasis, cystic fibrosis, alpha1-antitrypsin deficiency and others.

The problem of the present invention is to prepare new compounds which on the basis of their pharmaceutical effectiveness as inhibitors of neutrophil elastase activity, may be used therapeutically, that is for the treatment of pathophysiological processes caused by increased activity of neutrophil elastase.

It has surprisingly been found that the compounds of the present invention have the following properties which are advantageous in view of the indications of the current invention.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, are additionally effective as inhibitors of neutrophil serine protease proteinase 3 and exhibit favourable inhibitory potency, as determined by the half maximal inhibitory concentration ($IC_{50}$), in an enzymatic inhibition assay. This inhibitory activity on a second neutrophil serine protease may be beneficial for pharmacological efficacy.

Some compounds according to the present invention, including the physiologically acceptable salts, exhibit favourable inhibitory potency, as determined by the half maximal effective concentration ($EC_{50}$), in a plasma or whole-blood assay, for instance as described is in T. Stevens et al. (*J. Pharm. Exp. Ther.* 2011, 339, 313-320).

Some compounds according to the present invention, including the physiologically acceptable salts, exhibit favourable in vivo potency, as determined, for example, by the half maximal effective dose ($ED_{50}$), in models of human neutrophil elastase-induced lung injury in mouse or rat, for instance as described in Tremblay et al. (*Chest* 2002, 121, 582-588) or T. Stevens et al. (*J. Pharm. Exp. Ther.* 2011, 339, 313-320).

Some compounds according to the present invention, including the physiologically acceptable salts, exhibit favourable metabolic stability in an in vitro microsomal assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

Some compounds according to the present invention, including the physiologically acceptable salts, exhibit favourable metabolic stability in an in vitro hepatocytes assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

An improved metabolic stability in an in vitro test system is expected to translate into a reduced in vivo clearance (CL), because the metabolic conversion in the liver is reduced. Based on the pharmacokinetic equation CL/F$_{oral}$=Dose/AUC (F$_{oral}$: oral bioavailability, AUC: area under the curve), a reduced in vivo clearance is expected to lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di (*Drug-like properties: concepts, structure design and methods: from ADME to toxicity optimization*, Elsevier, 1$^{st}$ ed, 2008), chapter 26 and references therein. For an oral drug, improved permeability is expected to translate is into a higher fraction of the drug absorbed in the intestinal tract, thus, resulting in higher dose-normalized systemic exposure (AUC).

Some compounds according to the present invention, including the physiologically acceptable salts, exhibit a favourable, that is low efflux ratio (permeability in the efflux direction divided by the permeability in the influx direction) in an in vitro Caco-2 or MDCK cell layer method as described in E. Kerns & L. Di (*Drug-like properties: concepts, structure design and methods: from ADME to toxicity optimization*, Elsevier, 1$^{st}$ ed, 2008), chapter 26 and 27 and references therein. For an oral drug, an improved, that is reduced efflux ratio is expected to translate into a higher fraction of the drug absorbed in the intestinal tract, thus, resulting in higher dose-normalized systemic exposure (AUC).

Some compounds according to the present invention, including the physiologically acceptable salts, exhibit favourable aqueous solubility in a kinetic or thermodynamic solubility method as described in E. Kerns & L. Di (*Drug-like properties: concepts, 15 structure design and methods: from ADME to toxicity optimization*, Elsevier, 1$^{st}$ ed, 2008), chapter 25 and references therein. For an oral drug, improved aqueous solubility is expected to translate into a higher fraction of the drug absorbed in the intestinal tract resulting in higher dose-normalized systemic exposure (AUC) and/or oral bioavailability (F$_{oral}$) and/or peak plasma concentration after administration (C$_{max}$). Furthermore, improved aqueous solubility is expected to reduce the risk of development challenges, such as expensive formulations, increased development time, high drug load.

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or prolonged duration of action of the drug when the same dose is applied.

Some compounds according to the present invention, including the physiologically acceptable salts, exhibit favourable metabolic stability, favourable permeability and favourable aqueous solubility. Accordingly, some compounds of the present invention are expected to exhibit favourable pharmacokinetic (PK) properties after oral dosing, in particular favourable systemic exposure (area under the curve, AUC), thus, leading to favourable efficacy in vivo.

Some compounds according to the present invention, including the physiologically acceptable salts, exhibit favourable pharmacokinetic (PK) properties. The PK properties can be determined in pre-clinical animal species, for example mouse, rat, hamster, dog, guinea pig, mini pig, cynomolgus monkey, rhesus monkey. The PK properties of a compound can be described, for example, by the following parameters: Mean residence time (MRT), elimination half-live (t$_{1/2}$), volume-of-distribution (V$_D$), area under the curve (AUC), clearance (CL) and bioavailability after oral administration (F$_{oral}$), peak plasma concentration after administration (C$_{max}$), time to reach Cmax (T$_{max}$).

Some compounds according to the present invention, including the physiologically acceptable salts, exhibit favourable, that is, low inhibition of cytochrome P450 (CYP) isozymes in corresponding in vitro assays for CYP isozyme inhibition as described in E. Kerns & L. Di (*Drug-like properties: concepts, structure design and methods: from ADME to toxicity optimization*, Elsevier, 1$^{st}$ ed, 2008), chapter 32 and references therein. Reduced inhibition of CYP isozymes is expected to translate into a reduced risk for undesirable drug-drug interactions which is the interference of one drug with the normal metabolic or pharmacokinetic behaviour of a co-administered drug.

Some compounds according to the present invention, including the physiologically acceptable salts, exhibit favourable, that is low Cytochrome P450 (CYP) induction potential. CYP induction can affect the pharmacokinetics of a drug molecule upon multiple dosing, which can result in undesirable pharmacokinetic drug-drug interactions with co-administered drugs. CYP induction can lead to decreased exposure of the inducing is compound (e.g. autoinduction) or decreased exposure of a co-administered compound metabolized by the induced enzyme. CYP induction can also lead to an increase in the metabolism of a drug causing changes in pharmacological (active metabolite) and toxicological (toxic metabolite) outcomes.

Some compounds according to the present invention, including the physiologically acceptable salts, exhibit favourable, that is, low, inhibition of the hERG channel in a patch clamp assay as described in E. Kerns & L. Di (*Drug-like properties: concepts, structure design and methods: from ADME to toxicity optimization*, Elsevier, 1$^{st}$ ed, 2008), chapter 34 and references cited therein.

DETAILED DESCRIPTION OF THE INVENTION

A compound of formula 1,

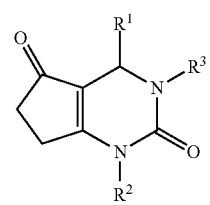

1 wherein
R$^1$ is phenyl,
  substituted with CN and
  substituted with a second substituent R$^{1.1}$,
  R$^{1.1}$ is selected from the group consisting of
    —CH$_2$OH, —CH(CH$_3$)OH, —C(CH$_3$)$_2$OH,
    —SO$_2$—CH$_2$CH$_3$, —SO$_2$—CH$_3$, —SO$_2$—CH$_2$CH$_2$—OCH$_3$, —SO$_2$—CH$_2$CH$_2$—OH, —SO$_2$—CH$_2$CH$_2$CH$_2$—OH and —SO—CH$_2$CH$_3$, —SO—CH$_3$,
R$^2$ is phenyl or pyridyl, each ring substituted with R$^{2.1}$,
  R$^{2.1}$ is selected from the group consisting of
    CF$_3$, CHF$_2$, Br and Cl, $R^3$ is selected from the group consisting of
H, $CH_3$, —CO—NH—$CH_3$, —CO—NH—$CH_2CH_3$, —$CH_2CH_2$—OH, —$CH_2CH_2CH_2$—OH, and —$CH_2$-oxetane
or optical and geometrical isomers, solvates, hydrates or salts, preferably pharmaceutically acceptable salts thereof,
provided that a compound of formula 1 is not a compound selected from the group consisting of
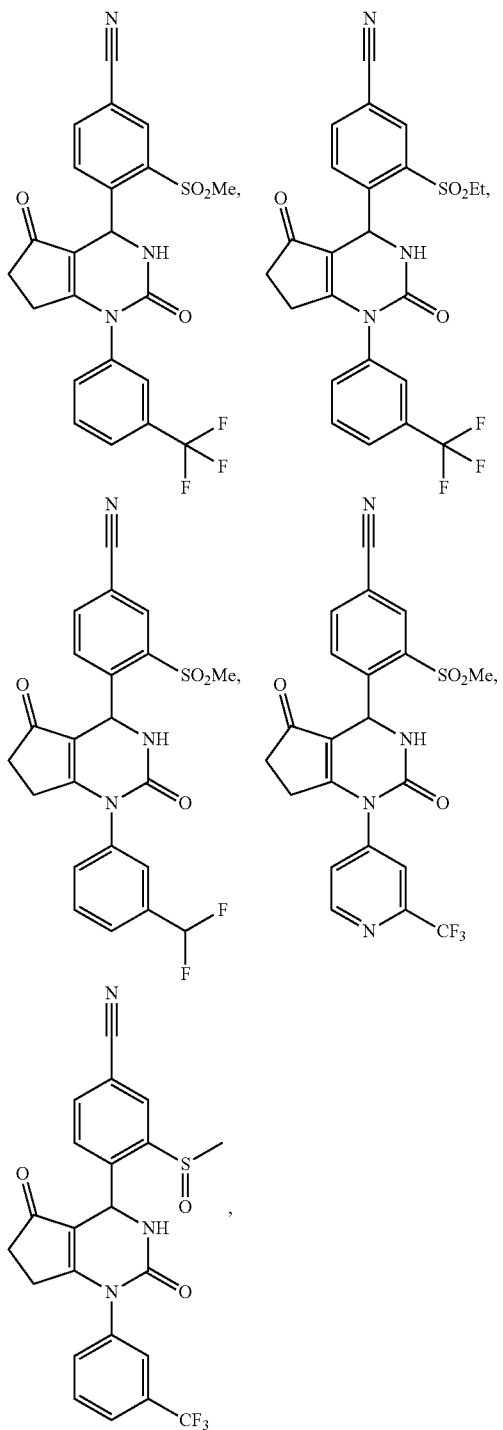
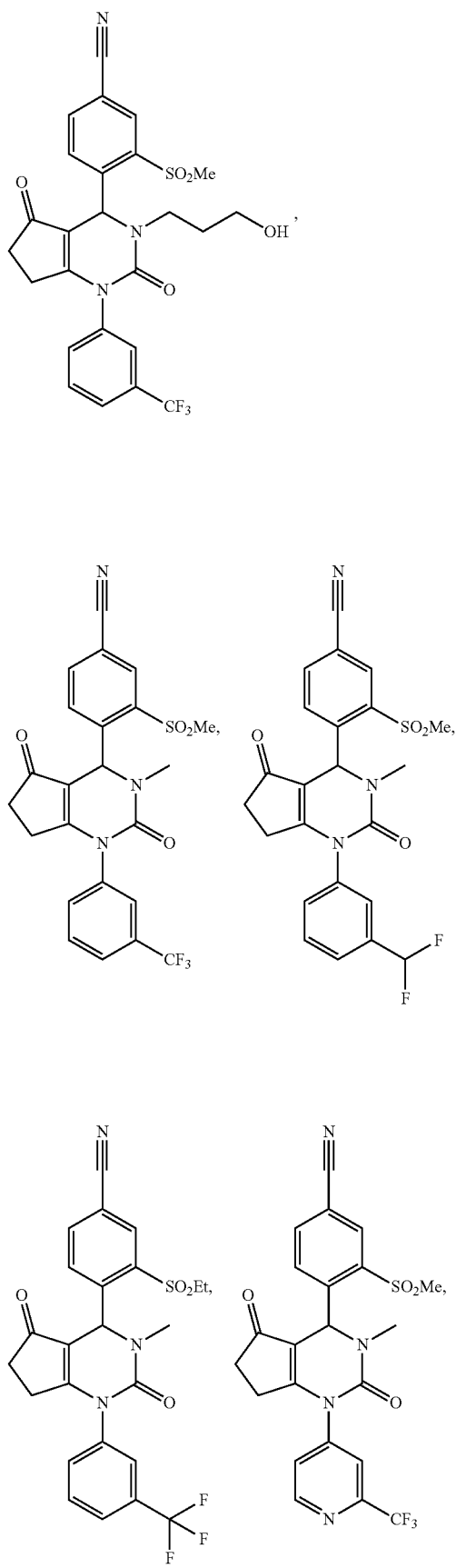

-continued
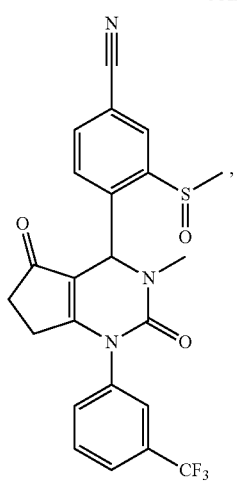
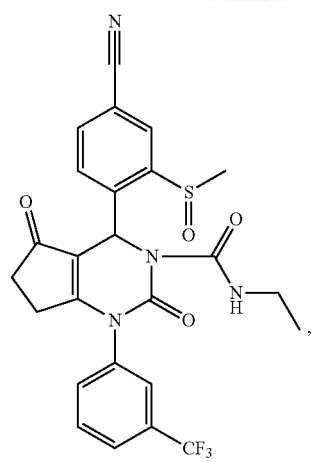
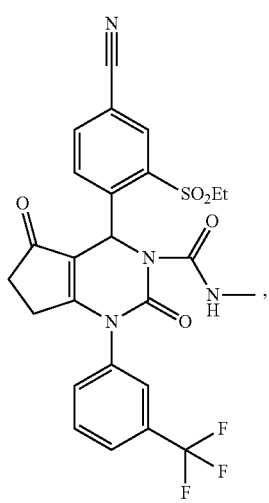
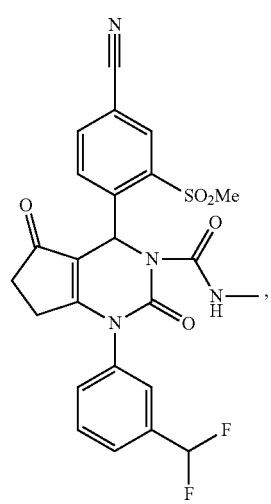
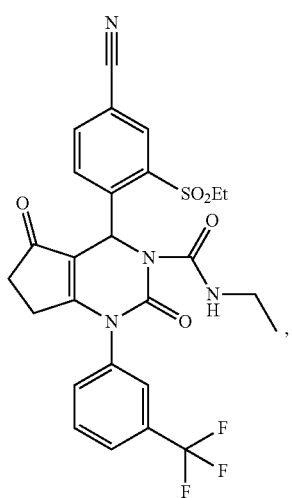
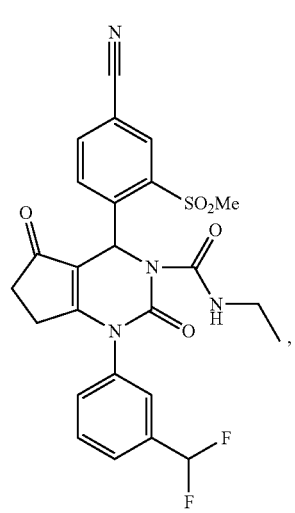

-continued

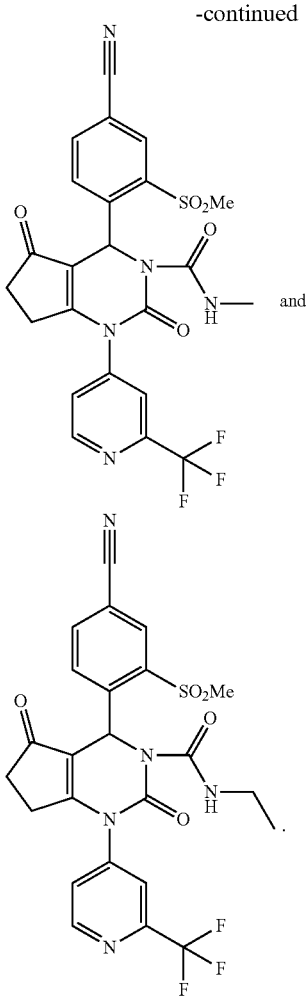
and

For example, the term "3-carboxypropyl-group" represents the following substituent:

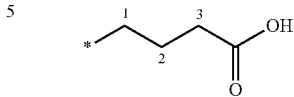

wherein the carboxy group is attached to the third carbon atom of the propyl group. The is terms "1-methylpropyl-", "2,2-dimethylpropyl-" or "cyclopropylmethyl-" group represent the following groups:

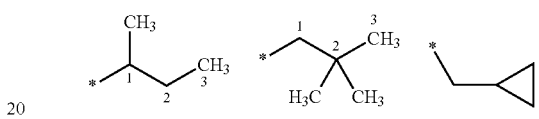

The asterisk may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected is statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well Used Terms and Definitions Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, S(O), $S(O)_2$, NC (cyano), HOOC, $F_3C$ or the like, is the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk may be used in sub-formulas to indicate the bond which is connected to the core molecule as defined.

as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

All isomeric forms (especially all stereoisomeric forms, e.g. all chiral, enantiomeric, diastereomeric and racemic forms, all tautomeric and all geometric isomeric forms) of a compound of the present invention are intended with this invention, unless the specific isomer is specifically indicated. Obviously, the isomer which is pharmacologically more potent and/or more efficacious is preferred.

It will be appreciated that the compounds of the present invention contain at least one asymmetrically substituted carbon atom, and may therefore be isolated as pure enantiomers or as a racemic or non-racemic mixture of both enantiomers. It will be appreciated that some of the compounds of the present invention contain more than one stereogenic center, that is more than one asymmetrically substituted carbon or sulfur atom, and may therefore be isolated as pure diastereomers or as diastereomeric mixtures, both in optically active or racemic forms.

The invention contemplates all conceivable stereoisomers, particularly the diastereomers and enantiomers mentioned herein, e.g. in substantially pure form, in enriched form (e.g. substantially free of any or all other undesired enantiomers and/or diastereomers and/or in any mixing ratio, including the racemic forms, as well as the salts thereof.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (that is an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, to improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, is particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris-(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethane-sulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (–)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (–)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

By the term "halo" added to a "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: H$_2$FC—, HF$_2$C—, F$_3$C—.

The above mentioned provision that a compound of formula 1 is not a compound selected from the above mentioned group means specifically that a compound of formula 1 is not a compound selected from a group consisting of

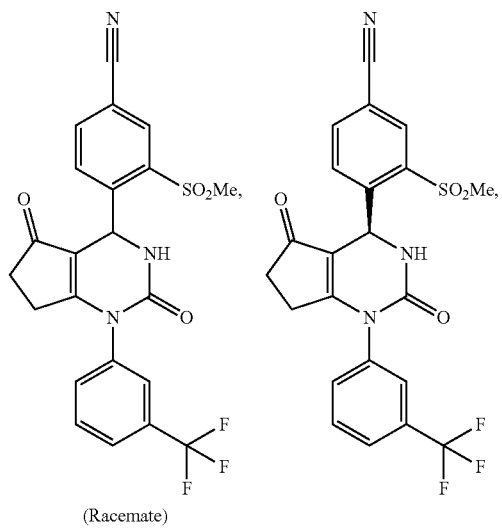

(Racemate)

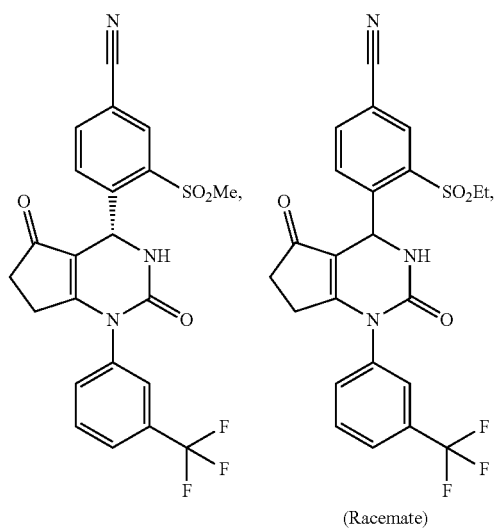

(Racemate)

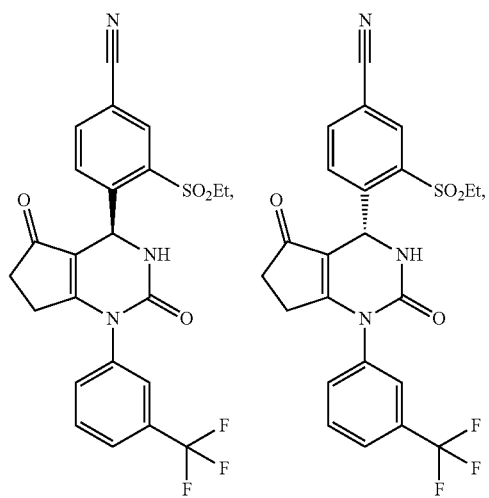

-continued
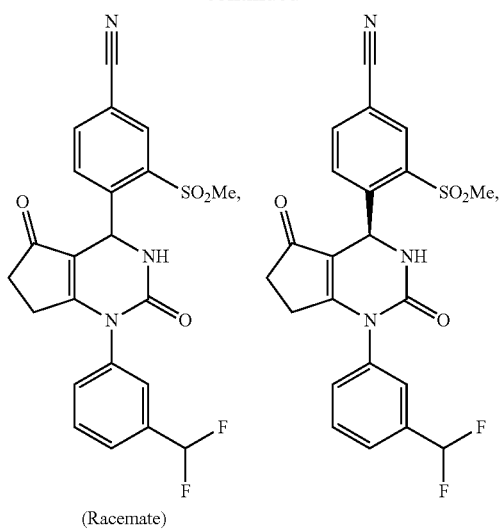
(Racemate)
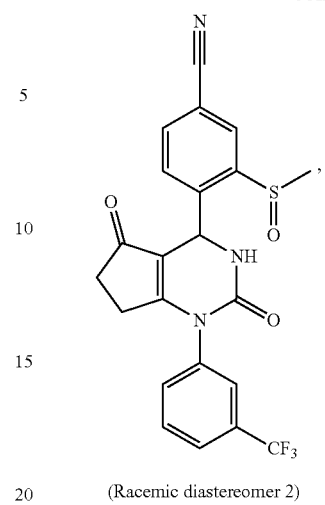
(Racemic diastereomer 2)
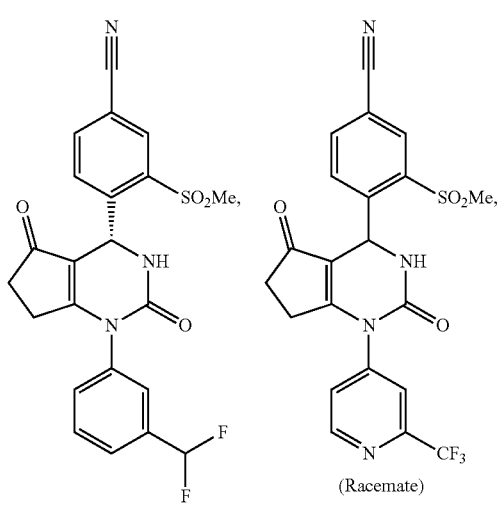
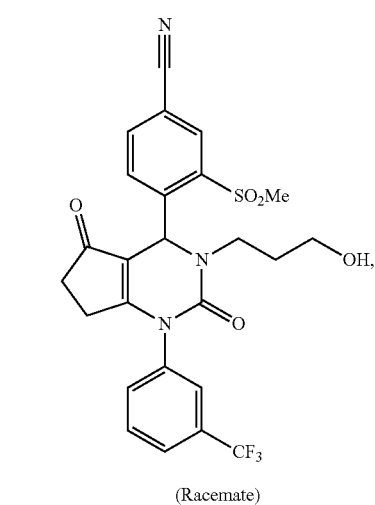
(Racemate)
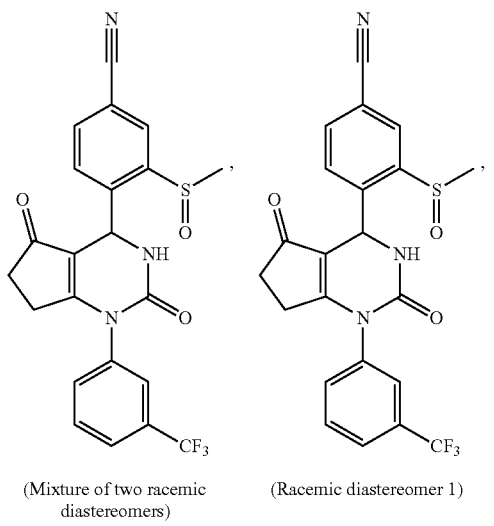
(Mixture of two racemic diastereomers)   (Racemic diastereomer 1)
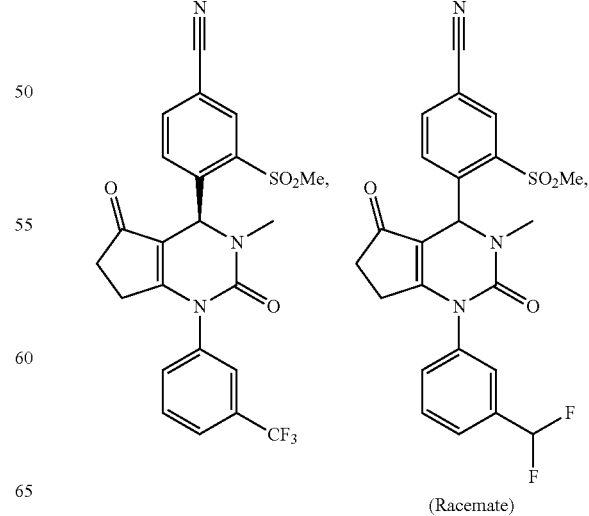
(Racemate)

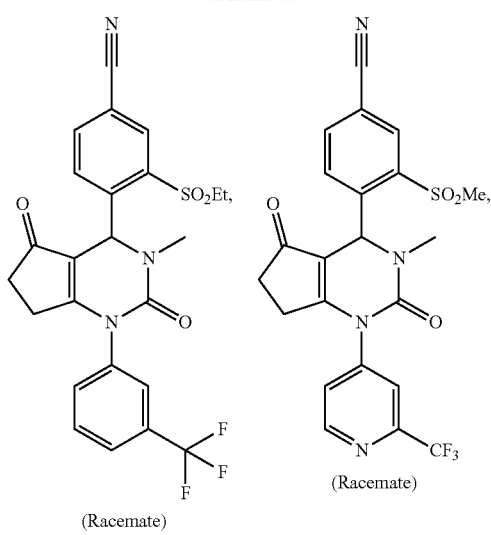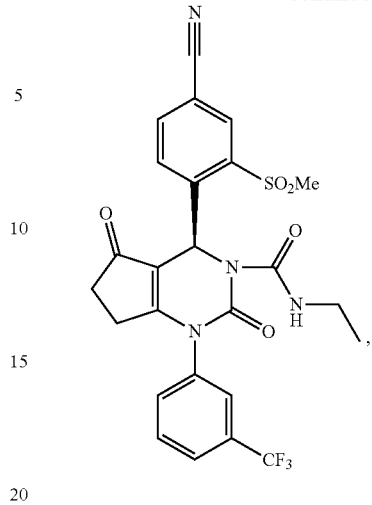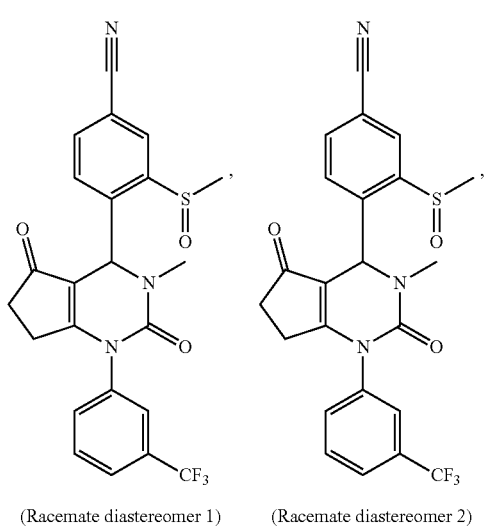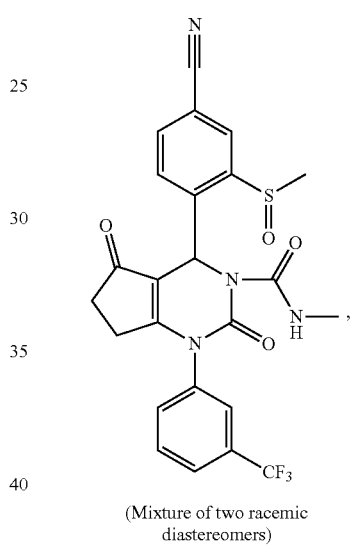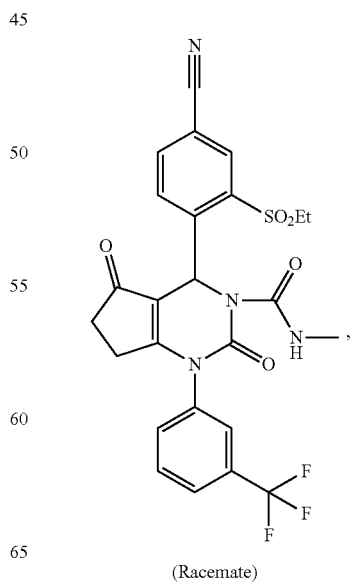

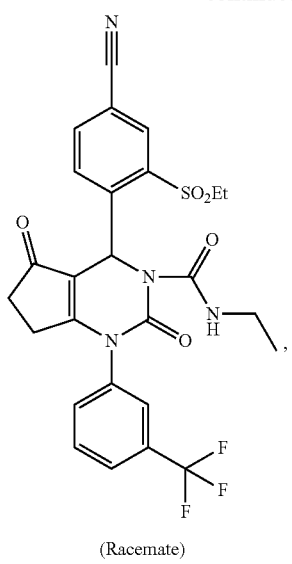
(Racemate)
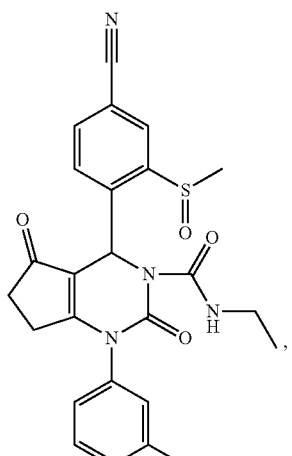
(Mixture of two racemic diastereomers)
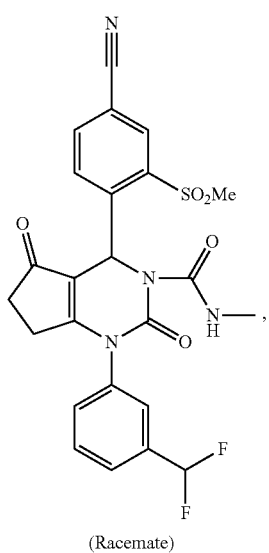
(Racemate)
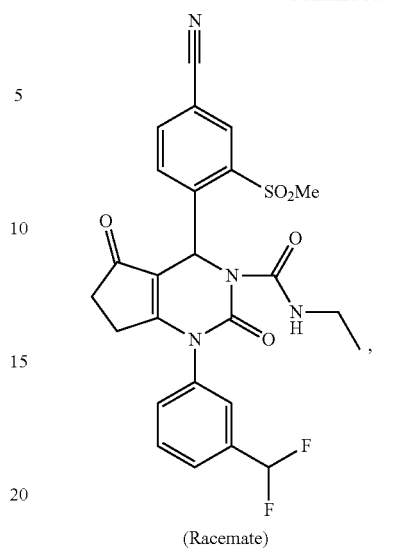
(Racemate)
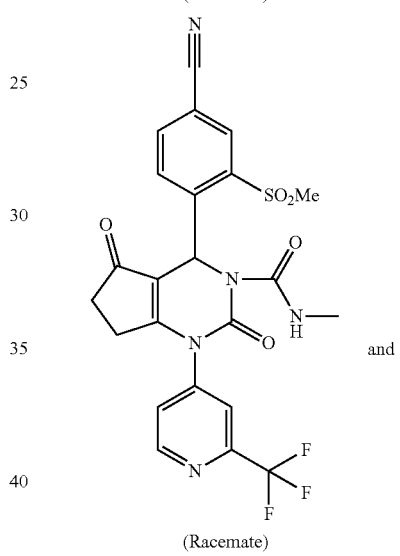
and
(Racemate)
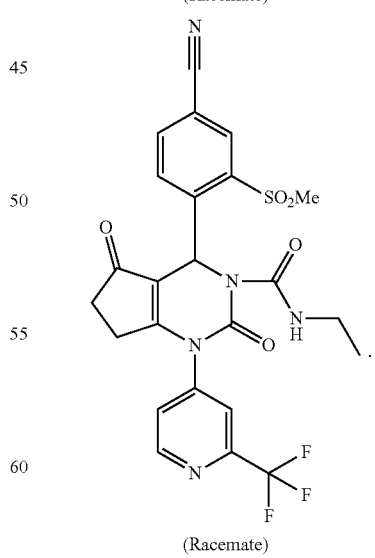
(Racemate)
which are disclosed in the European patent application No. 13154256.5.

Embodiments

Embodied are the above compounds of formula 1, wherein
$R^1$ is phenyl,
  substituted with CN and
  substituted with a second substituent $R^{1.1}$,
  $R^{1.1}$ is selected from the group consisting of
    —CH$_2$OH, —SO$_2$—CH$_2$CH$_3$, —SO$_2$—CH$_2$CH$_2$—OH, —SO$_2$—CH$_2$CH$_2$CH$_2$—OH —SO—CH$_2$CH$_3$ and —SO—CH$_3$,
$R^2$ is phenyl substituted with $R^{2.1}$,
  $R^{2.1}$ is selected from the group consisting of
    CF$_3$ and CHF$_2$,
$R^3$ is selected from the group consisting of
  H and CH$_3$,
or a pharmaceutical acceptable salt thereof, Embodied are the above compounds of formula 1, wherein
$R^1$ is phenyl,
  substituted with CN and
  substituted with a second substituent $R^{1.1}$,
  $R^{1.1}$ is —CH$_2$OH,
or a pharmaceutical acceptable salt thereof.

Embodied are the above compounds of formula 1, selected from the group consisting of compounds 1.a to 1.h.

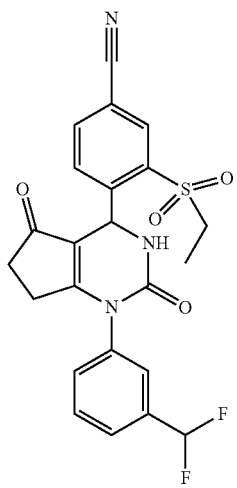

1.a

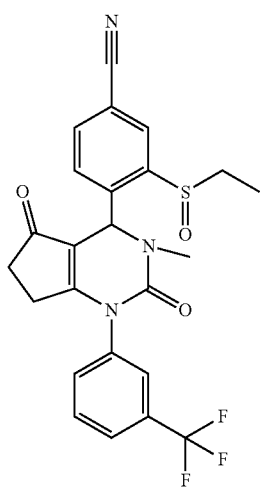

1.b

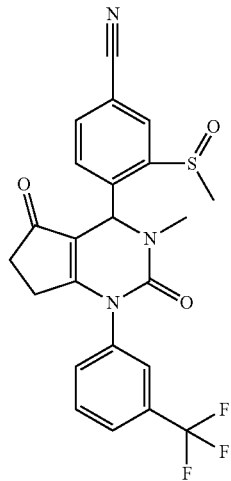

1.c

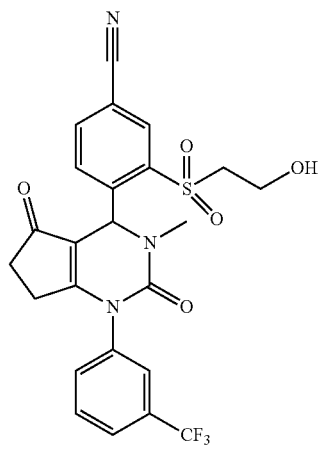

1.d

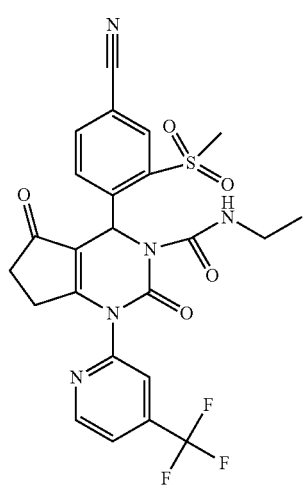

1.e

-continued
1.f
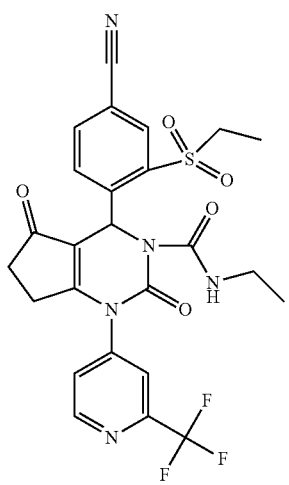
1.g
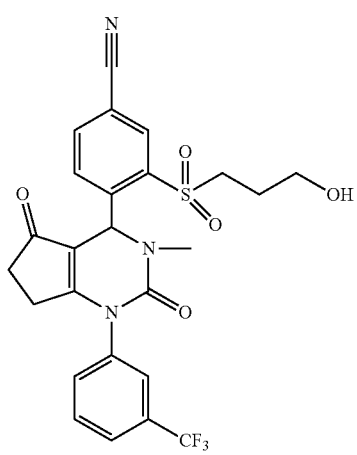
1.h
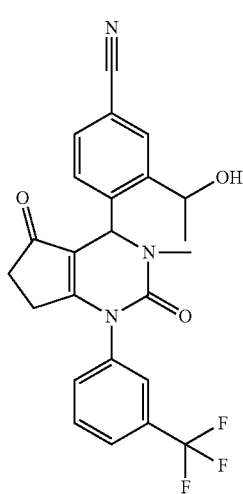
or a pharmaceutical acceptable salt thereof.
Embodied are the above compounds of formula 1, wherein the configuration of formula 1 is formula 1'
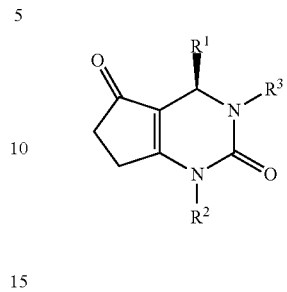
1'
or a pharmaceutical acceptable salt thereof.
Embodied are the above compounds of formula 1', selected from the group consisting of compounds 1.a' to 1.h'
1.a'
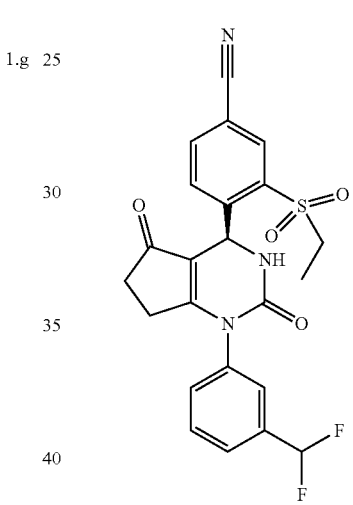
1.b'
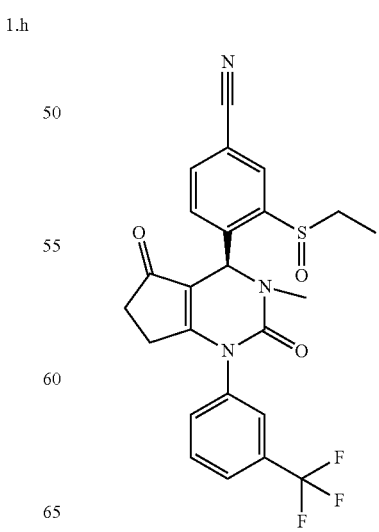

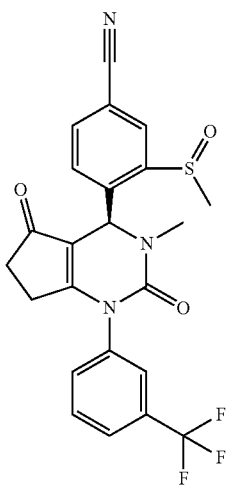
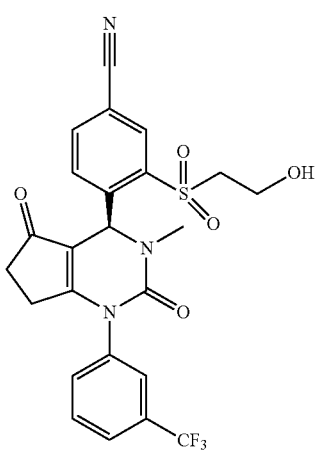
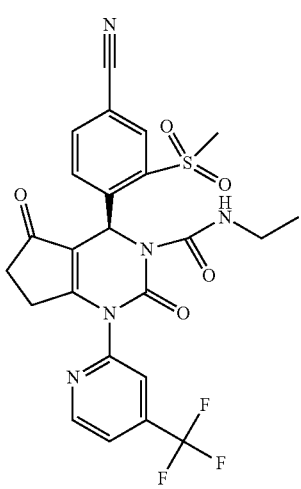
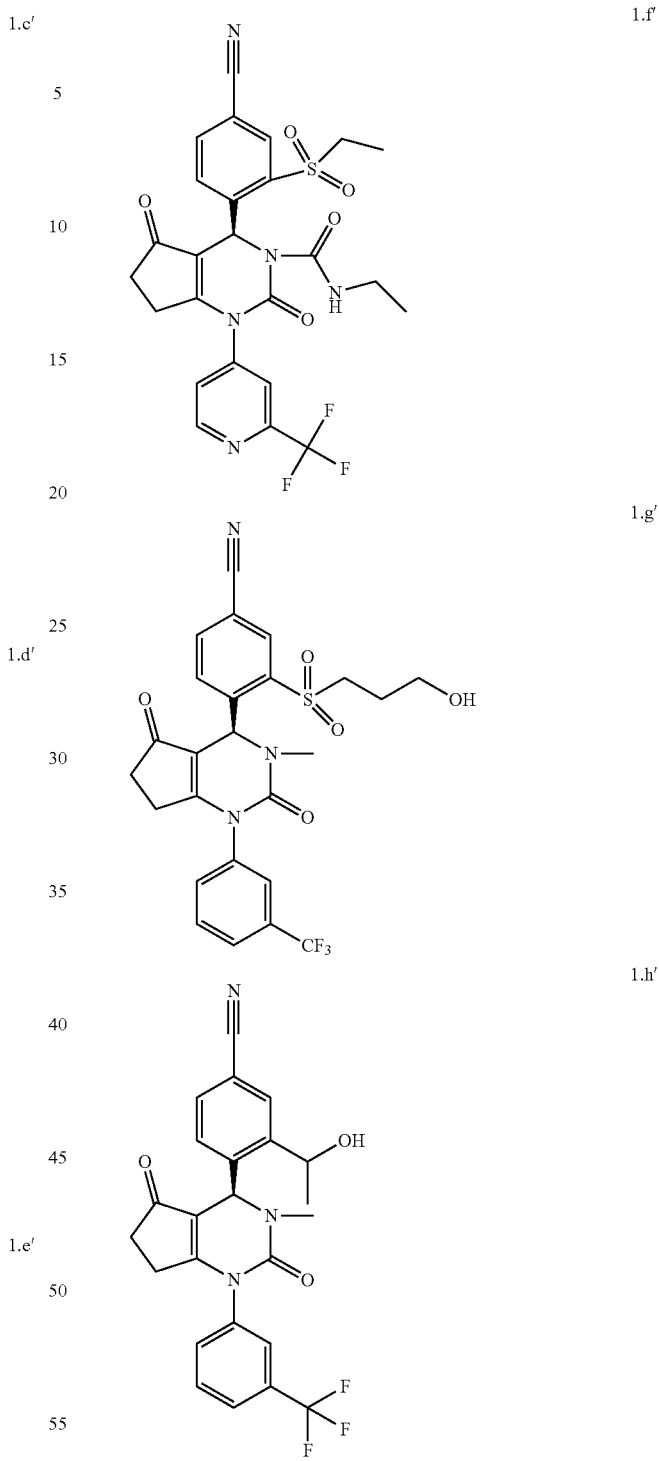
or a pharmaceutically acceptable salt thereof.
Embodied are the above compounds of formula 1, wherein $R^{1.1}$ is $R^{1.1.a}$, and $R^{1.1.a}$ is selected from the group consisting of
—CH$_2$OH, —CH(CH$_3$)OH, —C(CH$_3$)$_2$OH, —SO$_2$—CH$_2$CH$_3$, —SO$_2$—CH$_3$, —SO$_2$—CH$_2$CH$_2$—OCH$_3$, —SO$_2$—CH$_2$CH$_2$—OH, —SO$_2$—CH$_2$CH$_2$CH$_2$—OH, —SO—CH$_2$CH$_3$ and —SO—CH$_3$
or a pharmaceutical acceptable salt thereof.

Embodied are the above compounds of formula 1, wherein $R^{1.1}$ is $R^{1.1.b}$, and $R^{1.1.b}$ is selected from the group consisting of —$CH_2OH$,   —$CH(CH_3)OH$,   —$SO_2$—$CH_2CH_2CH_2$—$OH$,   —$SO_2$—$CH_2CH_2$—$OH$,   —$SO_2$—$CH_2CH_3$, —$SO_2$—$CH_3$,   —$SO_2$—$CH_2CH_2$—$OCH_3$,   —$SO$—$CH_2CH_3$ and —$SO$—$CH_3$ or a pharmaceutical acceptable salt thereof.

Embodied are the above compounds of formula 1, wherein $R^{1.1}$ is $R^{1.1.b}$, and $R^{1.1.b}$ is selected from the group consisting of —$CH_2OH$, —$CH(CH_3)OH$, —$SO_2$—$CH_2CH_2CH_2$—OH —$SO_2$—$CH_2CH_3$, —$SO_2$—$CH_3$, —$SO_2$—$CH_2CH_2$—$OCH_3$, —$SO$—$CH_2CH_3$ and —$SO$—$CH_3$ or a pharmaceutical acceptable salt thereof.

Embodied are the above compounds of formula 1, wherein $R^{1.1}$ is $R^{1.1.c}$, and $R^{1.1.c}$ is selected from the group consisting of

—$CH_2OH$,   —$SO_2$—$CH_2CH_2CH_2$—OH,   —$SO_2$—$CH_2CH_2$—OH,

—$SO_2$—$CH_2CH_3$, —$SO$—$CH_2CH_3$ and —$SO$—$CH_3$ or a pharmaceutical acceptable salt thereof.

Embodied are the above compounds of formula 1, wherein $R^{1.1}$ is $R^{1.1.c}$, and $R^{1.1.c}$ is selected from the group consisting of

—$CH_2OH$, —$SO_2$—$CH_2CH_2CH_2$—OH

—$SO_2$—$CH_2CH_3$, —$SO$—$CH_2CH_3$ and —$SO$—$CH_3$ or a pharmaceutical acceptable salt thereof.

Embodied are the above compounds of formula 1, wherein $R^2$ is $R^{2.a}$, and $R^{2.a}$ is phenyl or pyridyl, each ring substituted with $R^{2.1}$, $R^{2.1}$ is selected from the group consisting of $CF_3$, $CHF_2$, Br and Cl or a pharmaceutical acceptable salt thereof.

Embodied are the above compounds of formula 1, wherein $R^2$ is $R^{2.b}$, and $R^{2.b}$ is phenyl, substituted with $R^{2.1}$, $R^{2.1}$ is selected from the group consisting of $CF_3$ and $CHF_2$ or a pharmaceutical acceptable salt thereof.

Embodied are the above compounds of formula 1, wherein $R^2$ is $R^{2.c}$, and $R^{2.c}$ is pyridyl, substituted with $R^{2.1}$, $R^{2.1}$ is selected from the group consisting of $CF_3$ and $CHF_2$ or a pharmaceutical acceptable salt thereof.

Embodied are the above compounds of formula 1, wherein $R^{2.1}$ is $CF_3$ or a pharmaceutical acceptable salt thereof.

Embodied are the above compounds of formula 1, wherein $R^{2.1}$ is $CHF_2$ or a pharmaceutical acceptable salt thereof.

Embodied are the above compounds of formula 1, wherein $R^3$ is $R^{3.a}$ and $R^{3.a}$ is selected from the group consisting of H, $CH_3$, —CO—NH—$CH_3$, —CO—NH—$CH_2CH_3$, —$CH_2CH_2$—OH, and —$CH_2CH_2CH_2$—OH and —$CH_2$-oxetane or a pharmaceutical acceptable salt thereof.

Embodied are the above compounds of formula 1, wherein $R^3$ is $R^{3.b}$ and $R^{3.b}$ is selected from the group consisting of H, $CH_3$, CO—NH—$CH_3$, —CO—NH—$CH_2CH_3$, and —$CH_2CH_2CH_2$—OH or a pharmaceutical acceptable salt thereof.

Embodied are the above compounds of formula 1, wherein $R^3$ is $R^{3.c}$ and $R^{3.c}$ is selected from the group consisting of H and $CH_3$ or a pharmaceutical acceptable salt thereof.

Embodied are the above compounds of formula 1, wherein the compounds are selected from the group consisting of examples A.1A, A.2, A.3, B.1.2B, B.1.3A, C.1B, C.2A, C5.1, C.5.2, D.1A, D.3B, D.4.1A, D.4.4, D.4.5 and D.5A or a pharmaceutical acceptable salt thereof.

Embodied are the above compounds of formula 1, wherein the compounds are selected from the group consisting of examples A.2, A.3, B.1.2B, B.1.3A, C.1B, C.2A, C5.1, C.5.2, D.1A, D.3B, D.4.1A, D.4.4, D.4.5 and D.5A or a pharmaceutical acceptable salt thereof.

Embodied are the above compounds of formula 1, wherein the compounds are selected from the group consisting of examples A.1A, A.3, B.1.2B, B.1.3A, C.1B, C.2A, C5.1, C.5.2, D.4.1A, D.4.5 and D.5A or a pharmaceutical acceptable salt thereof.

Embodied are the above compounds of formula 1, wherein the compounds are selected from the group consisting of examples A.3, B.1.2B, B.1.3A, C.1B, C.2A, C5.1, C.5.2, D.4.1A, D.4.5 and D.5A or a pharmaceutical acceptable salt thereof.

Any and each other of the definitions of $R^1$, $R^{1.1}$, $R^{1.1.a}$, $R^{1.1.b}$, $R^{1.1.c}$, $R^2$, $R^{2.a}$, $R^{2.b}$, $R^{2.c}$, $R^{2.1}$, $R^3$, $R^{3.a}$, $R^{3.b}$ and $R^{3.c}$ may be combined with each other.

Another embodiment of the invention is an above compound of formula 1 for use as a medicament.

A further embodiment of the invention is an above compound of formula 1 for use as a medicament for the treatment of asthma and allergic diseases, gastrointestinal inflammatory diseases, glomerulonephritis, eosinophilic diseases, chronic obstructive pulmonary disease, infection by pathogenic microbes and rheumatoid arthritis.

A further embodiment of the invention is an above compound of formula 1 for use as a medicament for the treatment of neutrophilic diseases, cystic fibrosis (CF), non-cystic fibrosis, idiopathic pulmonary fibrosis, bronchiectasis, ANCA-associated vasculitis, lung cancer, non-cyctic fibrosis bronchiectasis, emphysema, chronic bronchitis, acute lung injury (ALI), acute respiratory distress syndrome (ARDS), pulmonary hypertension, pulmonary arterial hypertension (PAH) and Alpha-1-antitrypsin deficiency (AATD).

A further embodiment of the invention is an above compound of formula 1 for use as a medicament for the treatment of obesity and related inflammation, insulin resistance, diabetes, fatty liver and liver steatosis.

A further embodiment of the present invention is an above compound of formula 1, for use as a medicament for the treatment of traumatic brain injury, abdominal aortic aneurism and Graft vs. Host Disease (GvHD).

A further embodiment of the invention is a pharmaceutical composition, containing one or more of the above compounds of formula 1 or a pharmaceutically active salt thereof.

A further embodiment of the invention is a method of treatment or prevention of diseases in which neutrophil elastase inhibitors have a therapeutic benefit, which method comprises administration of a therapeutically or preventively effective amount of an above compound of formula 1 to a patient in need thereof.

A further embodiment of the invention is a pharmaceutical composition comprising additionally to an above compound of formula 1, a pharmaceutically active compound selected from the group consisting of betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, but also combinations of two or three active substances.

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes. Starting materials are commercially available or may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Compounds of the invention VI are accessible using the synthetic route illustrated in Scheme 1; $R^I$, $R^{E.1}$, $R^{E.2}$ have the meanings as defined hereinbefore and hereinafter.

in the presence of a strong Brønsted or a Lewis acid, for example sulfuric acid, hydrogen chloride, p-toluenesulfonic acid, Amberlyst 15, tetrafluoroboric acid, trifluoroacetic acid or boron trifluoride, either without solvent as a melt or in a suitable solvent, such as benzene, toluene, acetonitrile, diethyl ether, chloroform, acetic anhydride or mixtures thereof. The reaction takes place within 1 to 24 hours. Preferred reaction temperatures are between room temperature and 160° C., or the boiling point of the solvent, respectively. Preferably the reaction is done with molten ethyl carbamate as reactant and a catalytic amount of concentrated sulfuric acid at temperatures of 140-160° C. without any additional solvent.

The chlorination (Step B, intermediate II→intermediate III) can be done as described in Vovk et al. (*Synlett* 2006, 3, 375-378) and Sinitsa et al. (*J. Org. Chem. USSR* 1978, 14, 1107) by heating intermediate II together with a chlorinating agent, for example phosphorous pentachloride, phosphoryl chloride or sulfuryl chloride in an organic solvent, for example benzene or toluene. The reaction takes place within 1 to 24 hours. Preferred reaction temperatures are between 50° C. and 150° C.

Alternatively, intermediates III can be prepared as described in Jochims et al. (*Chem. Ber.* 1982, 115, 860-870) by α-halogenation of aliphatic isocyanates, for example benzyl isocyanate, using for example a bromination agent, for example N-bromosuccinimide. Isocyanates can be synthesized as described in U.S. Pat. No. 6,207,665 and in Charalambides et al. (*Synth. Commun.* 2007, 37, 1037-1044), by reacting an amine precursor with phosgene.

Intermediates V (Step C, intermediate IV→intermediates V) can be prepared as described in Chen et al. (*Synth. Commun.* 2010, 40, 2506-2510) and Tietcheu et al. (*J.*

SCHEME 1

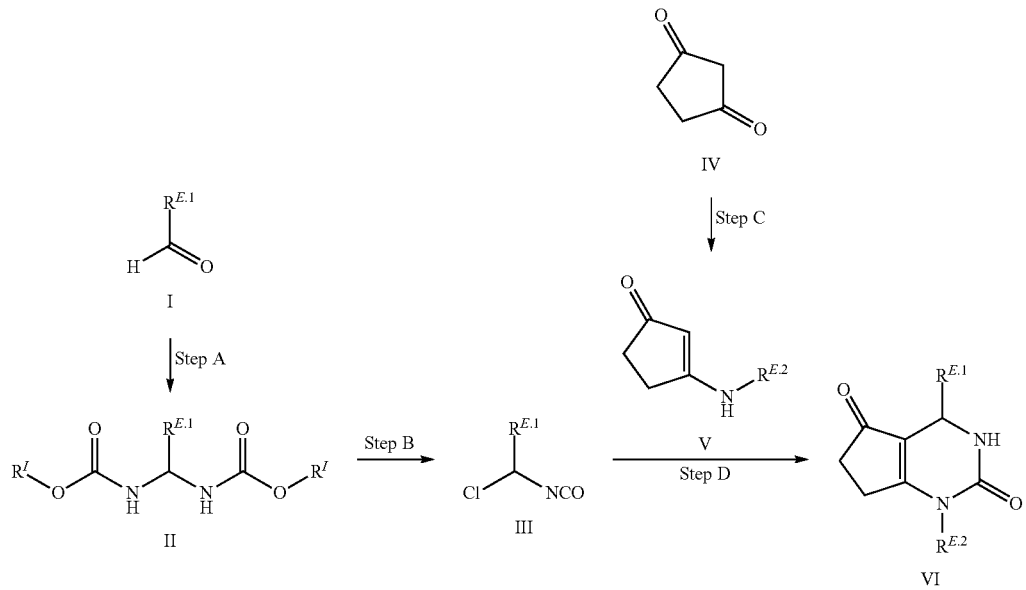

Intermediates II (Step A, intermediate I→intermediate II) can be prepared as described in Vovk et al. (*Synlett* 2006, 3, 375-378) or in PL2004/369318, by heating an aliphatic or aromatic aldehyde I with a carbamate, for example methyl carbamate, ethyl carbamate (urethane) or benzyl carbamate

*Heterocyclic Chem.* 2002, 39, 965-973) by reacting cyclopentane-1,3-dione (IV) and an aliphatic or aromatic amine in the presence of a catalyst, for example Ytterbium triflate [Yb(OTf)$_3$] or an acid, for example hydrogen chloride, acetic acid or p-toluenesulfonic acid, optionally in a solvent, for example water, acetic acid, acetonitrile, benzene, toluene. The reaction takes place within 1-24 hours. Preferred reaction temperatures are between room temperature and 120° C., most preferred room temperature.

Alternatively, intermediates V can be prepared as described in Scott et al. (*J. Med. Chem.* 1993, 36, 1947-1955) by direct condensation of the 1,3-dicarbonyl compound with an aliphatic or aromatic amine under reflux in a suitable solvent, for example benzene or toluene with azeotropic removal of water. Alternatively, intermediates V can be prepared as described in Mariano et al. (*J. Org. Chem.* 1984, 49, 220-228) by reacting an aliphatic or aromatic amine with 3-chloro-2-cyclopenten-1-one, which can be prepared from cyclopentane-1,3-dione.

Compounds according to the present invention (Step D, intermediates III→compounds of the invention VI) can be prepared as described in Vovk et al. (*Synlett* 2006, 3, 375-378), Vovk et al. (*Russ. J. Org. Chem.* 2010, 46, 709-715) and Kushnir et al. (*Russ. J. Org. Chem.* 2011, 47, 1727-1732) by reacting intermediates III with intermediates V in an organic solvent, for example dichloromethane, chloroform, benzene or toluene. The reaction takes place within 1-24 hours. Preferred reaction temperatures are between 0° C. is and 100° C.

Compounds according to the present invention VII are accessible via the synthetic route depicted in scheme 2; $R^{E.1}$, $R^{E.2}$, $R^{E.3}$ have the meanings as defined hereinbefore and hereinafter.

SCHEME 2

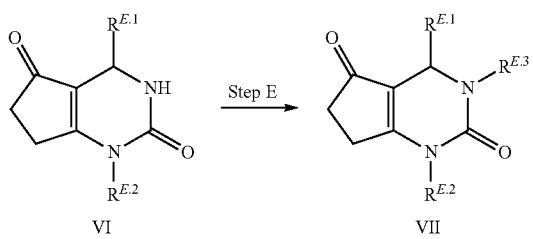

Compounds of the invention VII (Step E, compounds of the invention VI→compounds of the invention VII, $R^{E.3}$=alkyl or substituted alkyl) can be prepared as described in WO04024700 by reacting compounds of the invention VI with an alkylating agent, for example a dialkyl sulfate, for example dimethyl sulfate, an alkyl halide, for example methyl iodide or an alkyl sulfonylate, for example benzyl tosylate, in the presence of a suitable base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example tetrahydrofuran, N,N-dimethylformamide, acetonitrile, 1,4-dioxane, dichloromethane or toluene. The reaction takes place within 1-72 hours. Preferred reaction temperatures are between 0° C. and 100° C.

Compounds according to the present invention XIII are accessible via the synthetic routes depicted in scheme 3; $R^{III}$, $R^{IV}$, $R^{E.1}$, $R^{E.2}$ have the meanings as defined hereinbefore and hereinafter.

SCHEME 3

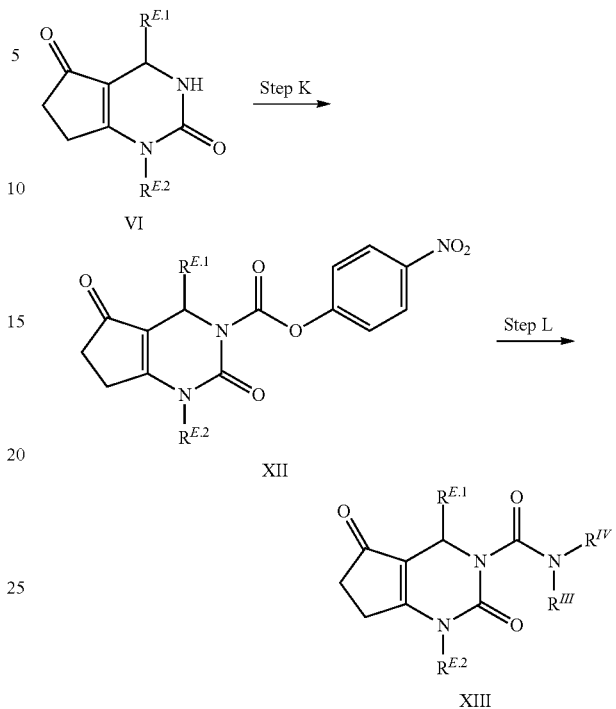

4-Nitrophenyl carbamate intermediates XII (Step K, compounds of the invention VI→intermediates XII) can be prepared as described in WO09080199, by reacting compounds of the invention VI with 4-nitrophenyl chloroformate in the presence of a base, for example triethylamine, N,N-diisopropylethylamine or N-methylmorpholine, optionally in the presence of a catalyst, for example 4-dimethylaminopyridine, in an organic solvent, for example dichloromethane, tetrahydrofuran, acetonitrile or N,N-dimethylformamide. The reaction takes place within 1-24 hours. Preferred reaction temperatures are between 0° C. and 50° C., most preferred room temperature.

Compounds of the invention XIII (Step L, 4-nitrophenyl carbamate intermediates XII→compounds of the invention XIII) can be prepared as described in WO09080199, by reacting intermediates XII with an amine $R^{III}NH_2$ or $R^{III}R^{IV}NH$ in an organic solvent, for example dichloromethane, acetonitrile, tetrahydrofuran, 1,4-dioxane, toluene or N,N-dimethylformamide. The reaction takes place within 1-72 hours. Preferred reaction temperatures are between 0° C. and 50° C., most preferred room temperature.

In addition to the synthetic route depicted in Scheme 1, compounds of the invention VI are also accessible using the synthetic route depicted in Scheme 4, $R^{E.1}$, $R^{E.2}$ have the meanings as defined hereinbefore and hereinafter.

SCHEME 4

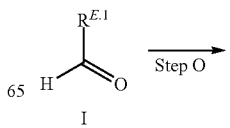

-continued

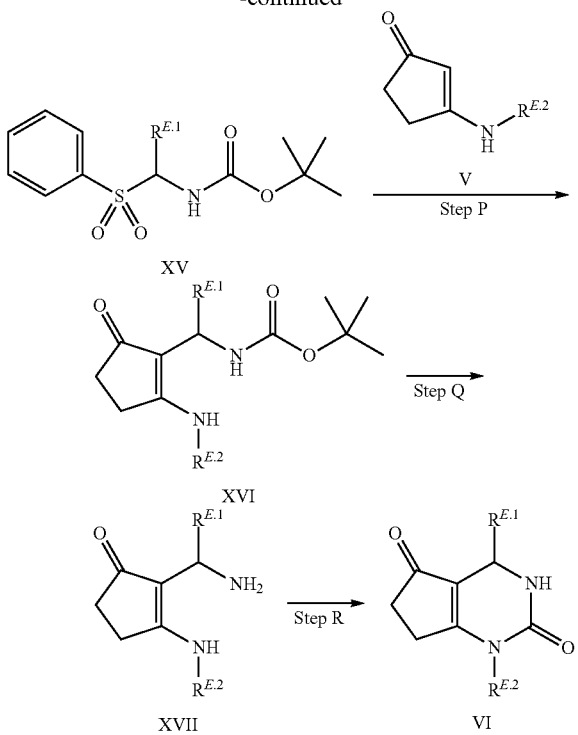

Intermediates XV (Step O, intermediate I→intermediate XV) can be prepared as is described in Best et al. (*J. Am. Chem. Soc.* 2012, 134, 18193-18196) or in Yang et al. (*Org. Synth.* 2009, 86, 11-17), by reacting an aromatic aldehyde I with a suitable sulfinate, for example sodium benzenesulfinic acid, and a suitable carbamate, for example methyl carbamate or tert-butyl carbamate, in the presence of a suitable acid, for example formic acid, in a suitable solvent, for example tetrahydrofuran, ethanol, methanol or a mixture of solvents, for example tetrahydrofuran and water. Alternatively, as described in Reingruber et al. (*Adv. Synth. Catal.* 2009, 351, 1019-1024) or in WO06136305, a suitable lewis acid, for example trimethylsilyl chloride, can be used as acid and acetonitrile or toluene can be used as solvent. The reaction takes place within 1-6 days. Preferred reaction temperatures are between 0° C. and 50° C., most preferred room temperature.

Intermediates XVI (Step P, intermediate XV→intermediate XVI) can be prepared in analogy to the method described for the preparation of compounds of the invention VI (Scheme 1, Step D, intermediate III→compound of the invention VI), by reacting intermediates XV with intermediates V in the presence of a suitable base, for example sodium hydride or sodium tert-butoxide, in a suitable organic solvent, for example tetrahydrofuran or 2-methyl-tetrahydrofuran. The reaction takes place within 1-24 h. Preferred reaction temperatures are between 0° C. and 50° C., most preferred room temperature.

Intermediates XVII (Step Q, intermediate XVI→intermediate XVII) can be prepared by reacting intermediates XVI with a suitable acid, for example hydrogen chloride, in a is suitable solvent, for example 1,4-dioxane. The reaction takes place between 1-72 hours. Preferred reaction temperatures are between 0° C. and room temperature, most preferred room temperature.

Compounds of the invention VI (Step R, intermediate XVII→compound of the invention VI) can be prepared as described in Csütörtöki et al. (*Tetrahedron Lett.* 2011, 67, 8564-8571) or in WO11042145, by reacting intermediates XVII with a suitable reagent, for example phosgene, triphosgene or carbonyl diimidazole, in the presence of a suitable base, for example triethylamine, N,N-diisopropylethylamine, pyridine or sodium carbonate, in a suitable solvent, for example acetonitrile, dichloromethane or toluene. The reaction takes place between 1-72 hours. Preferred reaction temperatures are between 0° C. and 50° C., most preferred room temperature.

Compounds of the invention XX are accessible via the synthetic routes depicted in scheme 5; $R^V$, $R^{E.2}$, $R^{E.3}$ have the meanings as defined hereinbefore and hereinafter.

SCHEME 5

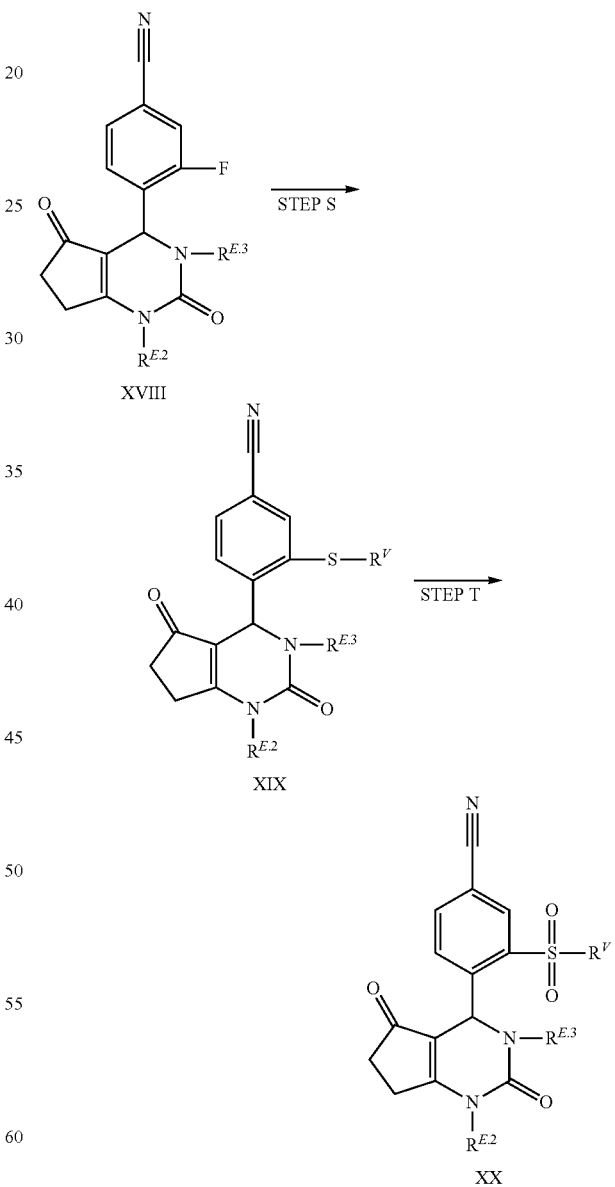

Intermediates XIX (Step S, compounds XVIII→compounds XIX, $R^{E.3}$=H or alkyl) can be prepared by reacting fluoro intermediates XVIII with a thiol $R^V$—SH in the presence of a suitable base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example N,N-dimethylformamide, tetrahydrofuran, acetonitrile, 1,4-dioxane, dichloromethane or toluene. The reaction takes place within 1-72 hours. Preferred reaction temperatures are between 0° C. and 100° C.

Compounds of the invention XX can be prepared by oxidation of sulfide intermediates XIX (Step T, intermediates XIX→compounds of the invention XX, $R^{E.3}$=H or alkyl) with an oxidating agent, for example hydrogen peroxide, 3-chloro-perbenzoic acid, periodic acid, sodium periodate, potassium permanganate, urea-hydrogen peroxide adduct, optionally in the presence of a metal catalyst, in a suitable solvent, for example dichloromethane, chloroform, methanol, ethanol, water or mixtures thereof. The reaction takes place within 1-72 h. Preferred reaction temperatures are between room temperature and the boiling point of the employed solvent.

Compounds of the invention bearing sulfoxide groups can be prepared by oxidation of the corresponding sulfide intermediates with an oxidating agent, for example hydrogen peroxide, 3-chloro-perbenzoic acid, periodic acid, sodium periodate, tert-butyl hydroperoxide, urea-hydrogen peroxide adduct, optionally in the presence of a metal catalyst, for example methyltrioxorhenium, $FeCl_3$, $Sc(OTf)_3$, titanium (IV) complexes, in a suitable solvent, for example dichloromethane, chloroform, methanol ethanol, water or mixtures thereof. The reaction takes place within 1-72 h. Preferred reaction temperatures are between room temperature and the boiling point of the employed solvent.

Preliminary Remarks

The term room temperature denotes a temperature of about 20° C. As a rule, $^1$H NMR spectra and/or mass spectra have been obtained of the compounds prepared. The retention times given are measured under the following conditions (TFA: trifluoroacetic acid, DEA: diethylamine, $scCO_2$: supercritical carbon dioxide):

Method Name: V011_S01
Column: XBridge C18, 4.6 × 30 mm, 3.5 μm
Column Supplier: Waters

| Gradient/Solvent Time [min] | % Solvent [$H_2O$, 0.1% $NH_3$] | % Solvent [acetonitrile] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method Name: V012_S01
Column: XBridge C18, 4.6 × 30 mm, 3.5 μm
Column Supplier: Waters

| Gradient/Solvent Time [min] | % Solvent [$H_2O$, 0.1% TFA] | % Solvent [acetonitrile] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method Name: X012_S01
Column: Xbridge BEH C18, 2.1 × 30 mm, 1.7 μm
Column Supplier: Waters

| Gradient/Solvent Time [min] | % Solvent [$H_2O$, 0.1% TFA] | % Solvent [acetonitrile] | Flow [ml/min] | Temperature [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method Name: X012_S02
Column: Xbridge BEH C18, 2.1 × 30 mm, 1.7 μm
Column Supplier: Waters

| Gradient/Solvent Time [min] | % Solvent [$H_2O$, 0.1% TFA] | % Solvent [acetonitrile] | Flow [ml/min] | Temperature [° C.] |
|---|---|---|---|---|
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method Name: Z011_S03
Column: XBridge C18, 3 × 30 mm, 2.5 μm
Column Supplier: Waters

| Gradient/Solvent Time [min] | % Solvent [$H_2O$, 0.1% $NH_3$] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z017_S04
Column: ZORBAX™ SB-$C_{18}$, 3 × 30 mm, 1.8 μm
Column Supplier: Agilent

| Gradient/Solvent Time [min] | % Solvent [$H_2O$, 0.1% TFA] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z018_S04
Column: Sunfire, 3 × 30 mm, 2.5 μm
Column Supplier: Waters

| Gradient/Solvent Time [min] | % Solvent [$H_2O$, 0.1% TFA] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |

-continued

Method Name: Z018_S04
Column: Sunfire, 3 × 30 mm, 2.5 μm
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 1.20 | 0 | 100 | 2.2 | 60 |
| 1.25 | 0 | 100 | 3 | 60 |
| 1.40 | 0 | 100 | 3 | 60 |

Method Name: 005_CA01
Column: SunFire C18, 3.0 × 30 mm, 2.5 μm
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 98 | 2 | 2.0 | 60.0 |
| 1.2 | 0 | 100 | 2.0 | 60.0 |
| 1.4 | 0 | 100 | 2.0 | 60.0 |

Method Name: 005_CA07
Column: SunFire C18, 3.0 × 30 mm, 2.5 μm
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 95 | 5 | 1.5 | 60.0 |
| 1.3 | 0 | 100 | 1.5 | 60.0 |
| 1.5 | 0 | 100 | 1.5 | 60.0 |
| 1.6 | 95 | 5 | 1.5 | 60.0 |

Method Name: I_IA_20_MeOH_NH3
Column: Chiralpak IA 4.6 × 250 mm, 5 μm
Column Supplier: Daicel

| Gradient/ Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 20 | 80 | 4 | 40 | 150 |

Method Name: I_IA_25_MeOH_NH3
Column: Chiralpak IA 4.6 × 250 mm, 5 μm
Column Supplier: Daicel

| Gradient/ Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 25 | 75 | 4 | 40 | 150 |

Method Name: I_IB_20_MeOH_DEA
Column: Chiralpak IB 4.6 × 250 mm, 5 μm
Column Supplier: Daicel

| Gradient/ Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 20 | 80 | 4 | 40 | 150 |

Method Name: I_IB_20_MeOH_NH3
Column: Chiralpak IB 4.6 × 250 mm, 5 μm
Column Supplier: Daicel

| Gradient/ Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 20 | 80 | 4 | 40 | 150 |

Method Name: I_IC_25_MeOH_NH3
Column: Chiralpak IC 4.6 × 250 mm, 5 μm
Column Supplier: Daicel

| Gradient/ Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 25 | 75 | 4 | 40 | 150 |

Method Name: I_IC_30_MeOH_NH3
Column: Chiralpak IC 4.6 × 250 mm, 5 μm
Column Supplier: Daicel

| Gradient/ Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 30 | 70 | 4 | 40 | 150 |

Method Name: I_IC_40_MeOH_NH3
Column: Chiralpak IC 4.6 × 250 mm, 5 μm
Column Supplier: Daicel

| Gradient/ Solvent Time [min] | % Solvent [MeOH, 20 mM NH$_3$] | % Solvent [scCO$_2$] | Flow [ml/min] | Temperature [° C.] | Back Pressure [bar] |
|---|---|---|---|---|---|
| 10 min | 40 | 60 | 4 | 40 | 150 |

SYNTHESES OF STARTING MATERIALS

The Following Starting Material is Prepared as Described in the Literature Cited:
3-(3-(Trifluoromethyl)phenylamino)cyclopent-2-enone: *Aust. J. Chem.* 2005, 58, 870-876.

SYNTHESES OF INTERMEDIATES

Intermediate A.1

{(2-Bromo-4-cyano-phenyl)-[5-oxo-2-(3-trifluoromethyl-phenylamino)-cyclopent-1-enyl]-methyl}-carbamic acid tert-butyl ester

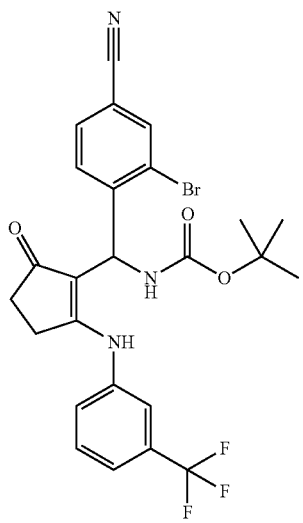 [SMILES: CC(C)(C)OC(=O)NC(C1=C(Nc2cccc(C(F)(F)F)c2)CCC1=O)c1ccc(C#N)cc1Br]

Step 1

[Benzenesulfonyl-(2-bromo-4-cyano-phenyl)-methyl]-carbamic acid tert-butyl ester Formic acid (3.9 mL, 104 mmol) is added to a mixture of tert-butyl carbamate (1.90 g, 16.2 mmol), 2-bromo-4-cyanobenzaldehyde (CAS #89891-69-0, 3.41 g, 16.2 mmol) and sodium benzenesulfinate (2.67 g, 16.2 mmol) in a mixture of THF (7.0 mL) and water (60 mL) and the mixture is stirred at room temperature for 6 days. Water (180 mL) is added and the precipitate is filtered and washed with water. The precipitate is treated with tert-butyl methyl ether (30 mL), and the mixture is stirred for 30 min. The precipitate is filtered off, washed with tert-butyl methyl ether and dried. Yield: 3.35 g. ESI mass spectrum: [M+H]$^+$=451 (bromine isotope pattern); Retention time HPLC: 0.66 min (X012_S01).

Step 2

{(2-Bromo-4-cyano-phenyl)-[5-oxo-2-(3-trifluoromethyl-phenylamino)-cyclopent-1-enyl]-methyl}-carbamic acid tert-butyl ester Sodium hydride (60% in mineral oil, 360 mg, 9.00 mmol) is added in small portions to a mixture of 3-(3-(trifluoromethyl)phenylamino)cyclopent-2-enone (2.16 g, 8.96 mmol) and 2-methyltetrahydrofuran (30 mL). After 30 min [benzenesulfonyl-(2-bromo-4-cyano-phenyl)-methyl]-carbamic acid tert-butyl ester (Step 1, 3.35 g, 7.43 mmol) is added and the mixture is stirred at room temperature for 2 h. Water is added and the phases are separated. The aqueous phase is extracted with ethyl acetate and the combined organic phases are washed with water, dried over MgSO$_4$ and concentrated under reduced pressure. The residue is treated with tert-butyl methyl ether and the mixture is stirred for 15 min. The precipitate is filtered off, washed with tert-butyl methyl ether and dried. Yield: 3.18 g. ESI mass spectrum: [M+H]$^+$=550 (bromine isotope pattern); Retention time HPLC: 0.73 min (X012_S01).

Intermediate A.2

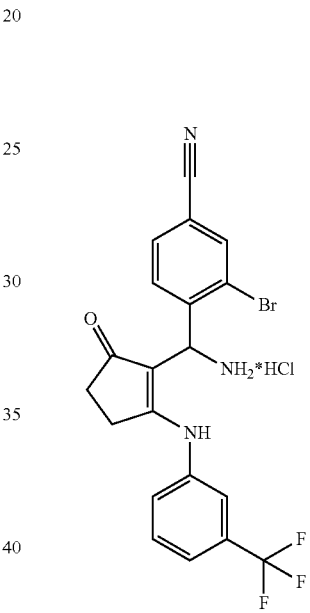

4-{Amino-[5-oxo-2-(3-trifluoromethyl-phenylamino)-cyclopent-1-enyl]-methyl}-3-bromo-benzonitrile hydrochloride A solution of hydrogen chloride in 1,4-dioxane (4 M, 15.2 mL, 61 mmol) is added to a mixture of {(2-bromo-4-cyanophenyl)-[5-oxo-2-(3-trifluoromethyl-phenylamino)-cyclopent-1-enyl]-methyl}-carbamic acid tert-butyl ester (INTERMEDIATE A.1, 6.71 g, 12.2 mmol) in 1,4-dioxane (30 mL). The mixture is stirred at room temperature for 2 h and then cooled in an ice bath. The precipitate is filtered off, washed with cold acetonitrile and diethyl ether and dried. Yield: 5.90 g. ESI mass spectrum: [M+H]$^+$=450 (bromine isotope pattern); Retention time HPLC: 1.17 min (V011_S01).

Intermediate A.3

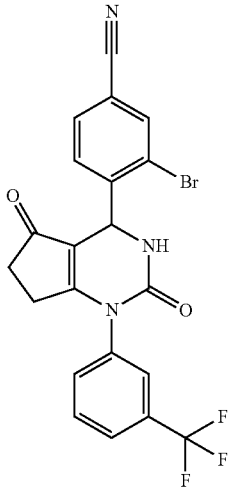 [SMILES: N#Cc1ccc(C2NC(=O)N(c3cccc(C(F)(F)F)c3)C3=C2C(=O)CC3)c(Br)c1]

3-Bromo-4-[2,5-dioxo-1-(3-trifluoromethyl-phenyl)-2,3,4,5,6,7-hexahydro-1H-cyclopentapyrimidin-4-yl]-benzonitrile Triethylamine (4.11 mL, 29.3 mmol) is added to a mixture of 4-{amino-[5-oxo-2-(3-trifluoromethyl-phenylamino)-cyclopent-1-enyl]-methyl}-3-bromo-benzonitrile hydrochloride (INTERMEDIATE A.2, 28.5 g, 58.6 mmol) and 1,1'-carbonyldiimidazole (11.9 g, 73.2 mmol) in acetonitrile (290 mL) and the mixture is stirred at room temperature overnight. Water (1.5 L) is added and the precipitate is filtered off, washed with water and dried. Yield: 24.5 g. ESI mass spectrum: [M+H]$^+$=476 (bromine isotope pattern); Retention time HPLC: 1.11 min (V011_S01).

Intermediate A.4

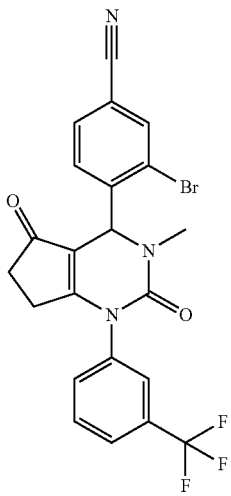 [SMILES: CN1C(=O)N(c2cccc(C(F)(F)F)c2)C2=C(C(=O)CC2)C1c1ccc(C#N)cc1Br]

3-Bromo-4-[3-methyl-2,5-dioxo-1-(3-trifluoromethyl-phenyl)-2,3,4,5,6,7-hexahydro-1H-cyclopentapyrimidin-4-yl]-benzonitrile Methyliodide (3.61 mL, 58.0 mmol) is added to a mixture of 3-bromo-4-(2,5-dioxo-1-(3-(trifluoromethyl)phenyl)-2,3,4,5,6,7-hexahydro-1H-cyclopentapyrimidin-4-yl)benzonitrile (INTERMEDIATE A.3, 23.0 g, 48.3 mmol) and cesium carbonate (20.5 g, 62.8 mmol) in DMF (230 mL) and the reaction mixture is stirred at room temperature overnight. Water and ethyl acetate are added and the phases are separated. The organic phase is washed with water, dried over MgSO$_4$ and concentrated. Yield: 24.0 g. ESI mass spectrum: [M+H]$^+$=490 (bromine isotope pattern); Retention time HPLC: 1.18 min (V011_S01).

Intermediate A.5

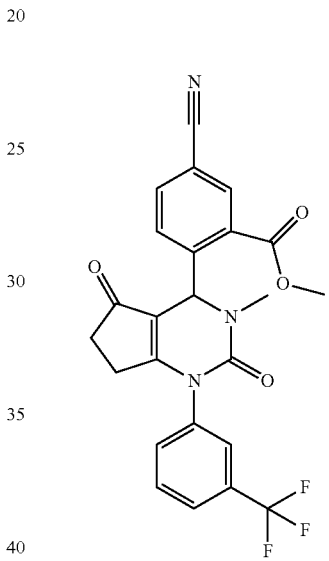

5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid methyl ester A solution of 3-bromo-4-[3-methyl-2,5-dioxo-1-(3-trifluoromethyl-phenyl)-2,3,4,5,6,7-hexahydro-1H-cyclopentapyrimidin-4-yl]-benzonitrile (INTERMEDIATE A.4, 11.85 g, 24.2 mmol), 1,1-bis(diphenylphosphino)-ferrocen (1.34 g, 2.42 mmol), palladium acetate (0.27 g, 1.21 mmol) and sodium acetate (5.95 g, 72.5 mmol) is treated with carbon monoxide at 5 bar and 100° C. for 40 h. After evaporation of volatiles under reduced pressure, water and ethyl acetate are added and the phases are separated. The organic phase is dried over MgSO$_4$ and concentrated under reduced pressure. The residue is purified by flash chromatography on silica (cyclohexane/ethyl acetate 1:1). Yield: 8.0. g. ESI mass spectrum: [M+H]$^+$=470; Retention time HPLC: 1.15 min (V011_S01).

Intermediate A.6

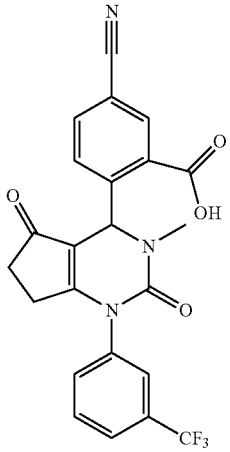 [SMILES: CN1C(=O)N(c2cccc(C(F)(F)F)c2)C2=C(C(=O)CC2)C1c1ccc(C#N)cc1C(=O)O]

5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid A mixture of 5-cyano-2-[3-methyl-2,5-dioxo-1-(3-trifluoromethyl-phenyl)-2,3,4,5,6,7-hexahydro-1H-cyclopentapyrimidin-4-yl]-benzoic acid methyl ester (INTERMEDIATE A.5, 6.70 g, 14.3 mmol) and lithium hydroxide (1.03 g, 42.8 mmol) in 1,4-dioxane (135 ml) and water (67.0 mL) is stirred at room temperature for 90 min. Water (250 mL) and hydrochloric acid (1.0 M, 44 mL) are added and the reaction mixture is extracted with ethyl acetate. The organic phase is washed with water, dried over MgSO$_4$ and concentrated under reduced pressure. Yield: 6.2. g. ESI mass spectrum: [M+H]$^+$=456; Retention time HPLC: 0.63 min (X012_S01).

Intermediate A.7

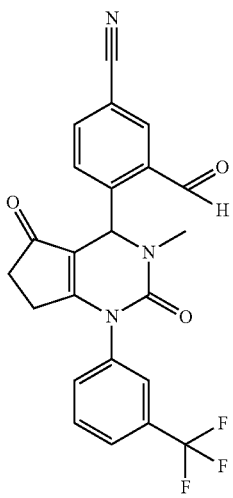 [SMILES: CN1C(=O)N(c2cccc(C(F)(F)F)c2)C2=C(C(=O)CC2)C1c1ccc(C#N)cc1C=O]

3-Formyl-4-[3-methyl-2,5-dioxo-1-(3-trifluoromethyl-phenyl)-2,3,4,5,6,7-hexahydro-1H-cyclopentapyrimidin-4-yl]-benzonitrile Dess-Martin periodinane (2.36 g; 5.57 mmol) is added to a solution of 3-hydroxymethyl-4-[3-methyl-2,5-dioxo-1-(3-trifluoromethyl-phenyl)-2,3,4,5,6,7-hexahydro-1H-cyclopentapyrimidin-4-yl]-benzonitrile (EXAMPLE A.1; 2.05 g; 4.644 mmol) in dichloromethane (100 mL) and the mixture is stirred at room temperature for 90 min. The reaction mixture is quenched with a mixture of 10% sodium thiosulfate solution (50 mL) and saturated NaHCO$_3$ solution (50 mL) and the phases are separated. The aqueous layer is extracted with dichloromethane. The combined organic layers are washed with water, dried over MgSO$_4$ and concentrated under reduced pressure. The residue is purified by flash chromatography on silica (dichloromethane/methanol 98:2). Yield: 510 mg; ESI mass spectrum: [M+H]+=440; Retention time HPLC: 0.63 min (X012_S02).

Intermediate B.1

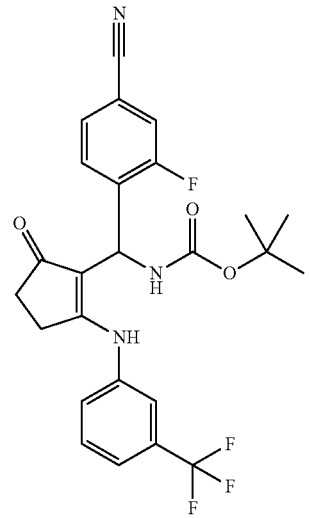 [SMILES: CC(C)(C)OC(=O)NC(C1=C(Nc2cccc(C(F)(F)F)c2)CCC1=O)c1ccc(C#N)cc1F]

{(4-Cyano-2-fluoro-phenyl)-[5-oxo-2-(3-trifluoromethyl-phenylamin)-cyclopent-1-enyl]-methyl}-carbamic acid tert-butyl ester INTERMEDIATE B.1 is prepared in analogous fashion as described for INTERMEDIATE A.1, replacing 2-bromo-4-cyanobenzaldehyde with 3-fluoro-4-formyl-benzonitrile (CAS #105942-10-7) as starting material. Purification of crude material is done by reversed phase HPLC (Waters SunFire™-C$_{18}$, gradient of acetonitrile in water, 0.1% formic acid). ESI mass spectrum: [M+H]$^+$=490; Retention time HPLC: 1.13 min (Z018_S04).

Intermediate B.2

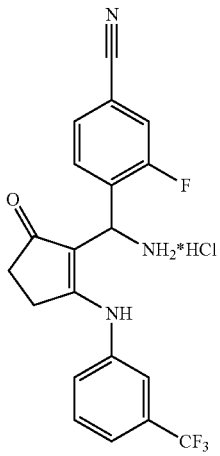

4-{Amino-[5-oxo-2-(3-trifluoromethyl-phenylamino)-cyclopent-1-enyl]-methyl}-3-fluoro-benzonitrile hydrochloride INTERMEDIATE B.2 is prepared in analogous fashion as described for INTERMEDIATE A.2, replacing INTERMEDIATE A.1 with INTERMEDIATE B.1 as starting material. ESI mass spectrum: [M+H—NH$_3$]+=373; Retention time HPLC: 0.81 min (Z018_S04).

Intermediate B.3

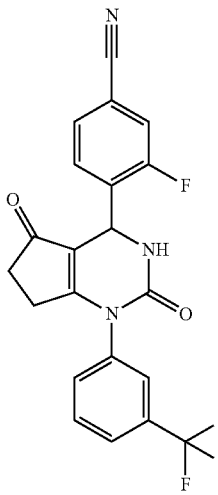

4-[2,5-Dioxo-1-(3-trifluoromethyl-phenyl)-2,3,4,5,6,7-hexahydro-1H-cyclopentapyrimidin-4-yl]-3-fluoro-benzonitrile INTERMEDIATE B.3 is prepared in analogous fashion as described for INTERMEDIATE A.3, replacing INTERMEDIATE A.2 with INTERMEDIATE B.2 as starting material. ESI mass spectrum: [M+H]+=416; Retention time HPLC: 0.97 min (Z018_S04).

Intermediate B.4

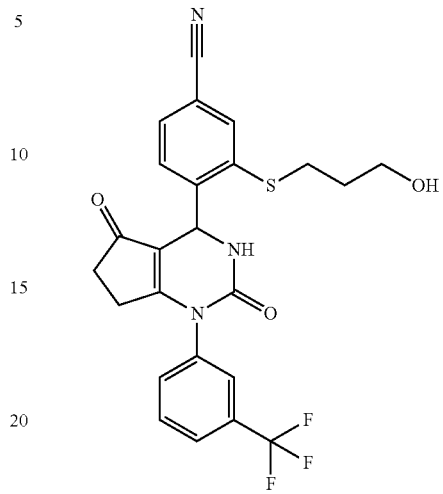

4-[2,5-Dioxo-1-(3-trifluoromethyl-phenyl)-2,3,4,5,6,7-hexahydro-1H-cyclopentapyrimidin-4-yl]-3-(3-hydroxy-propylsulfanyl)-benzonitrile To a mixture of sodium hydride (55% in mineral oil, 32 mg, 0.73 mmol) in DMF (0.30 mL) is added at 0° C. 3-mercapto-1-propanol (55 µL, 0.64 mmol) and the mixture is stirred at 0° C. for 25 min. A solution of 4-[2,5-dioxo-1-(3-trifluoromethyl-phenyl)-2,3,4,5,6,7-hexahydro-1H-cyclopentapyrimidin-4-yl]-3-fluoro-benzonitrile (INTERMEDIATE B.3, 110 mg, 0.21 mmol) in DMF (0.30 mL) is added and the mixture is stirred at room temperature for 2.5 h. The reaction mixture is quenched with water, acidified with dilute acetic acid and purified by reversed phase HPLC (Waters SunFire™-C$_{18}$, gradient of acetonitrile in water, 0.1% TFA). Yield: 13 mg. ESI mass spectrum: [M+H]+ =488; Retention time HPLC: 0.93 min (Z018_S04).

The following INTERMEDIATE B.4.1 is prepared in analogous fashion as described for INTERMEDIATE B.4, replacing 3-mercapto-1-propanol with 2-methoxy-ethanethiol as starting material.

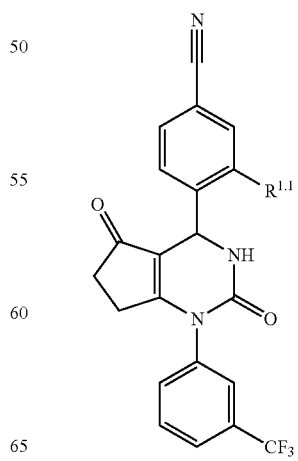

| INTER-MEDIATE | $R^{1.1}$ | MS $[M + H]^+$ | Retention time [min] | HPLC-Method |
|---|---|---|---|---|
| B.4.1 | ----S~~~O~ | 488 | 1.00 | Z018_S04 |

Intermediate B.5

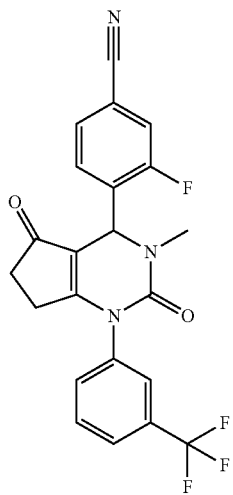 [SMILES: CN1C(=O)N(c2cccc(C(F)(F)F)c2)C2=C(C(=O)CC2)C1c1ccc(C#N)cc1F]

3-Fluoro-4-[3-methyl-2,5-dioxo-1-(3-trifluoromethyl-phenyl)-2,3,4,5,6,7-hexahydro-1H-cyclopentapyrimidin-4-yl]-benzonitrile INTERMEDIATE B.5 is prepared in analogous fashion as described for INTERMEDIATE A.4, replacing INTERMEDIATE A.3 with INTERMEDIATE B.3. The reaction mixture is purified by reversed phase HPLC (Agilent ZORBAX™ SB-C$_{18}$, gradient of acetonitrile in water, 0.1% TFA). ESI mass spectrum [M+H]$^+$=430; Retention time HPLC: 1.02 min (Z018_S04).

Intermediate B.6

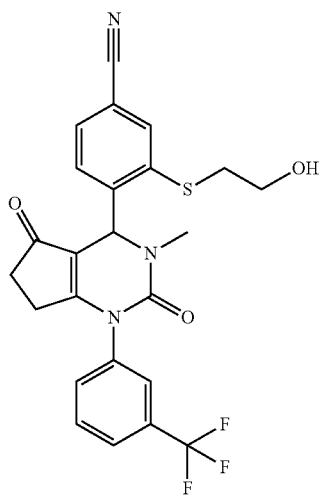 [SMILES: CN1C(=O)N(c2cccc(C(F)(F)F)c2)C2=C(C(=O)CC2)C1c1ccc(C#N)cc1SCCO]

3-(2-Hydroxy-ethylsulfanyl)-4-[3-methyl-2,5-dioxo-1-(3-trifluoromethyl-phenyl)-2,3,4,5,6,7-hexahydro-1H-cyclopentapyrimidin-4-yl]-benzonitrile INTERMEDIATE B.6 is prepared in analogous fashion as described for INTERMEDIATE B.4, replacing INTERMEDIATE B.3 with INTERMEDIATE B.5 and 3-mercapto-1-propanol with 2-mercaptoethanol as starting materials, respectively. ESI mass spectrum: [M+H]$^+$=488; Retention time HPLC: 0.97 min (Z018_S04).

The following INTERMEDIATES B.6.1 and B.6.2 are prepared in analogous fashion as described for INTERMEDIATE B.6, employing the appropriate thiol as starting material, respectively.

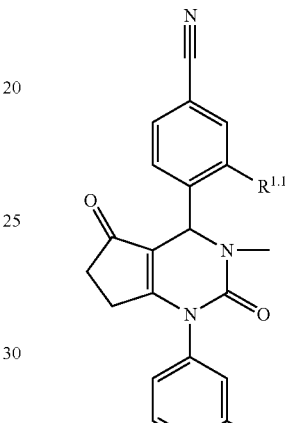

| INTER-MEDIATE | $R^{1.1}$ | MS $[M + H]^+$ | Retention time [min] | HPLC-Method |
|---|---|---|---|---|
| B.6.1 | ----S~~~OH | 502 | 0.98 | Z018_S04 |
| B.6.2 | ----S~~O~ | 502 | 1.07 | Z018_S04 |

Intermediate C.1

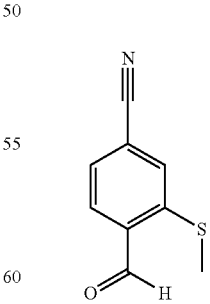

4-Formyl-3-methylsulfanyl-benzonitrile

Potassium carbonate (3.8 g; 27.2 mmol) is added to a mixture of 3-fluoro-4-formyl-benzonitrile (2.0 g; 13.4 mmol) and sodium thiomethanolate (1.175 g; 16.77 mmol) in DMF (10 mL) and the mixture is stirred at 120° C. for 2 h. The reaction mixture is cooled with an ice bath. Water is added and the precipitate is filtered off, washed with water and dried. Yield: 1.98 g. ESI mass spectrum: [M+H]$^+$=178; Retention time HPLC: 0.73 min (Z011_S03).

Intermediate C.2

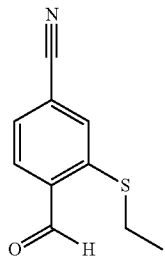

3-Ethylsulfanyl-4-formyl-benzonitrile

INTERMEDIATE C.2 is prepared in analogous fashion as described for INTERMEDIATE C.1, replacing sodium thiomethanolate with sodium thioethanolate (reaction temperature 50° C.). ESI mass spectrum: [M+H]$^+$=192; Retention time HPLC: 0.81 min (Z011_S03).

Intermediate C.3

{(4-Cyano-2-methylsulfanyl-phenyl)-[5-oxo-2-(3-trifluoromethyl-phenylamino)-cyclopent-1-enyl]-methyl}-carbamic acid tert-butyl ester

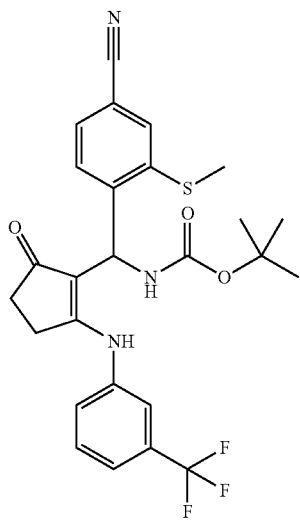 [SMILES: CSc1cc(C#N)ccc1C(NC(=O)OC(C)(C)C)C1=C(Nc2cccc(C(F)(F)F)c2)CCC1=O]

INTERMEDIATE C.3 is prepared in analogous fashion as described for INTERMEDIATE A.1, replacing 2-bromo-4-cyanobenzaldehyde with 4-formyl-3-methylsulfanyl-benzonitrile (INTERMEDIATE C.1). ESI mass spectrum: [M+H]$^+$=518; Retention time HPLC: 1.14 min (Z017_S04).

Intermediate C.4

{(4-Cyano-2-ethylsulfanyl-phenyl)-[5-oxo-2-(3-trifluoromethyl-phenylamino)-cyclopent-1-enyl]-methyl}-carbamic acid tert-butyl ester

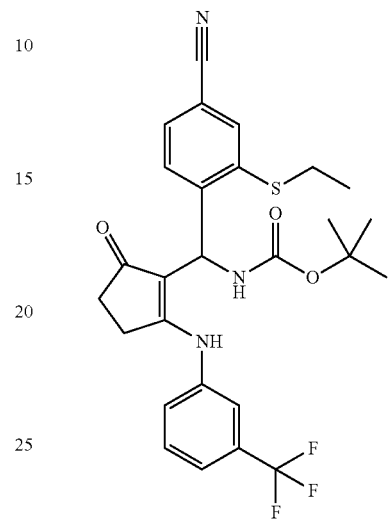

INTERMEDIATE C.4 is prepared in analogous fashion as described for INTERMEDIATE A.1, replacing 2-bromo-4-cyanobenzaldehyde with 3-ethylsulfanyl-4-formyl-benzonitrile (INTERMEDIATE C.2). ESI mass spectrum: [M+H]$^+$=532; Retention time HPLC: 1.19 min (Z018_S04).

Intermediate C.5

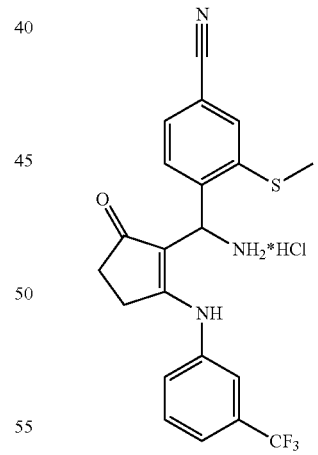

4-{Amino-[5-oxo-2-(3-trifluoromethyl-phenylamino)-cyclopent-1-enyl]-methyl}-3-methylsulfanyl-benzonitrile hydrochloride A solution of hydrogen chloride in 1,4-dioxane (4 M, 5 mL, 20 mmol) is added to a mixture of {(4-cyano-2-methylsulfanyl-phenyl)-[5-oxo-2-(3-trifluoromethyl-phenylamino)-cyclopent-1-enyl]-methyl}-carbamic acid tert-butyl ester (INTERMEDIATE C.3, 4.3 g, purity 80%, 6.7 mmol) in acetonitrile (10 mL) and the mixture is stirred at room temperature for 2 h. The precipitate is filtered off, washed with cold acetonitrile and dried.

Yield: 4.14 g. ESI mass spectrum: [M+H]⁺=418; Retention time HPLC: 0.90 min is (Z011_S03).

Intermediate C.6

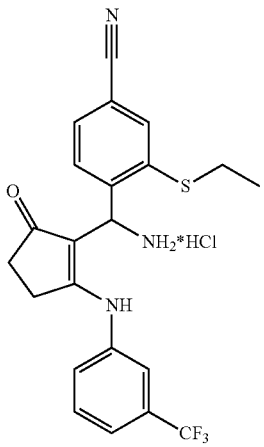

4-{Amino-[5-oxo-2-(3-trifluoromethyl-phenylamino)-cyclopent-1-enyl]-methyl}-3-ethylsulfanyl-benzonitrile hydrochloride INTERMEDIATE C.6 is prepared in analogous fashion as described for INTERMEDIATE C.5, replacing INTERMEDIATE C.3 with INTERMEDIATE C.4. ESI mass spectrum: [M+H]⁺=432; Retention time HPLC: 0.94 min (Z011_S03).

Intermediate C.7

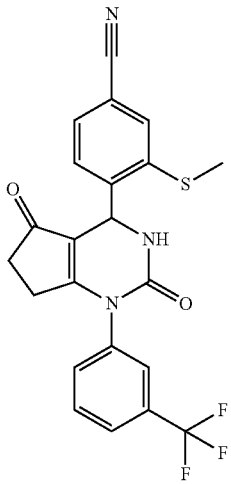 [SMILES: CSc1cc(C#N)ccc1C1NC(=O)N(c2cccc(C(F)(F)F)c2)C2=C1C(=O)CC2]

4-[2,5-Dioxo-1-(3-trifluoromethyl-phenyl)-2,3,4,5,6, 7-hexahydro-1H-cyclopentapyrimidin-4-yl]-3-methylsulfanyl-benzonitrile Triethylamine (95 μL, 0.68 mmol) is added to a mixture of 4-{amino-[5-oxo-2-(3-trifluoromethyl-phenylamino)-cyclopent-1-enyl]-methyl}-3-methylsulfanyl-benzonitrile hydrochloride (INTERMEDIATE C.5, 570 mg, 1.13 mmol based on 90% purity) and 1,1'-carbonyldiimidazole (220 mg, 1.36 mmol) in acetonitrile (3 mL) and the mixture is stirred at room temperature overnight. The reaction mixture is concentrated under reduced pressure, and the residue is treated with water. The precipitate is filtered off, washed with water and dried. Yield: 460 mg; ESI mass spectrum: [M+H]⁺=444; Retention time HPLC: 0.98 min (Z017_S04).

Intermediate C.8

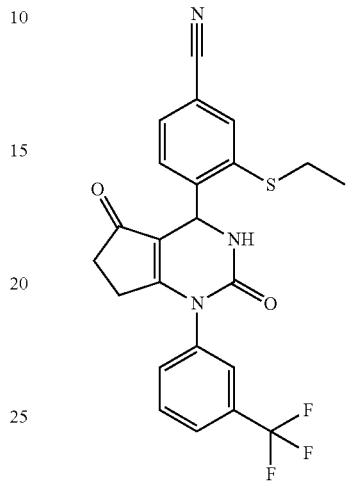

4-[2,5-Dioxo-1-(3-trifluoromethyl-phenyl)-2,3,4,5,6, 7-hexahydro-1H-cyclopentapyrimidin-4-yl]-3-ethylsulfanyl-benzonitrile INTERMEDIATE C.8 is prepared in analogous fashion as described for INTERMEDIATE C.7, replacing INTERMEDIATE C.5 with INTERMEDIATE C.6. ESI mass spectrum: [M+H]⁺=458; Retention time HPLC: 1.03 min (Z018_S04).

Intermediate C.9

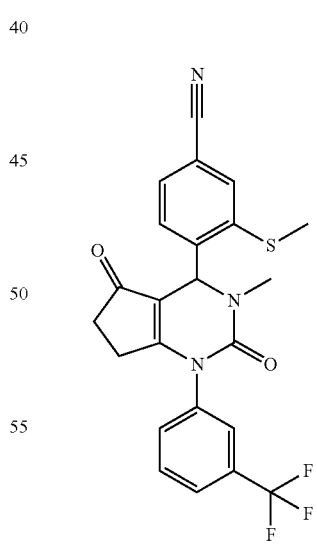

4-[3-Methyl-2,5-dioxo-1-(3-trifluoromethyl-phenyl)-2,3,4,5,6,7-hexahydro-1H-cyclopentapyrimidin-4-yl]-3-methylsulfanyl-benzonitrile Methyliodide (834 μL, 13.4 mmol) is added to a mixture of 4-[2,5-dioxo-1-(3-trifluoromethyl-phenyl)-2,3,4,5,6,7- hexahydro-1H-cyclopentapyrimidin-4-yl]-3-methylsulfanyl-benzonitrile (INTERMEDIATE C.7; 1.981 g; 4.467 mmol) and cesium carbonate (2.911 g, 8.935 mmol) in DMF (5 mL) and the reaction mixture is stirred at room temperature for 2 h. The mixture is purified by reversed phase HPLC (Stablebond, gradient of acetonitrile in water, 0.1% TFA). Yield: 1.145 g. ESI mass spectrum: [M+H]$^+$=458; Retention time HPLC: 1.03 min (Z017_S04).

Intermediate C.10

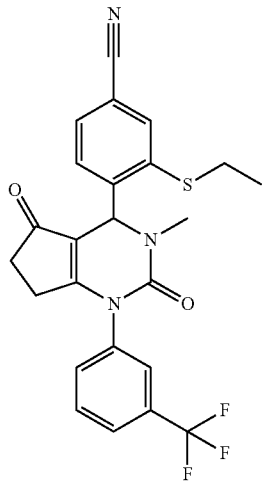 [SMILES: CCSc1cc(C#N)ccc1C1C2=C(CCC2=O)N(c2cccc(C(F)(F)F)c2)C(=O)N1C]

4-[3-Methyl-2,5-dioxo-1-(3-trifluoromethyl-phenyl)-2,3,4,5,6,7-hexahydro-1H-cyclopentapyrimidin-4-yl]-3-ethylsulfanyl-benzonitrile INTERMEDIATE C.10 is prepared in analogous fashion as described for INTERMEDIATE C.9, replacing INTERMEDIATE C.7 with INTERMEDIATE C.8. ESI is mass spectrum: [M+H]$^+$=472; Retention time HPLC: 1.09 min (Z018_S04).

Intermediate C.11.1 and Intermediate C.11.2

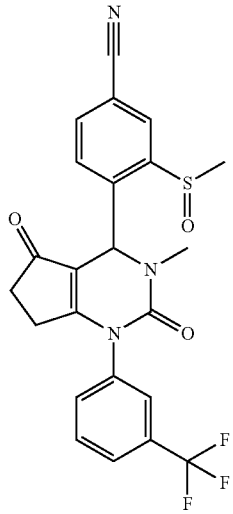 [SMILES: CN1C(=O)N(c2cccc(C(F)(F)F)c2)C2=C(C(=O)CC2)C1c1ccc(C#N)cc1S(C)=O]

3-Methanesulfinyl-4-[3-methyl-2,5-dioxo-1-(3-trifluoromethyl-phenyl)-2,3,4,5,6,7-hexahydro-1H-cyclopentapyrimidin-4-yl]-benzonitrile 3-Chloroperoxybenzoic acid (77%, 46 mg, 0.203 mmol) is added at room temperature to a solution of 4-[3-methyl-2,5-dioxo-1-(3-trifluoromethyl-phenyl)-2,3,4,5,6,7-hexahydro-1H-cyclopentapyrimidin-4-yl]-3-methylsulfanyl-benzonitrile (INTERMEDIATE C.9, 93 mg, 0.203 mmol) in dichloromethane (5 mL), and the mixture is stirred for 20 min. The reaction mixture is concentrated under reduced pressure and purified by reversed phase HPLC (Sunfire, gradient of acetonitrile in water, 0.1% TFA) yielding the two diastereomers.

Intermediate C.11.1

Yield: 46 mg; ESI mass spectrum [M+H]$^+$=474; Retention time HPLC: 0.94 min (early eluting diastereomer) (Z018_S04).

Intermediate C.11.2

Yield: 46 mg; ESI mass spectrum [M+H]$^+$=474; Retention time HPLC: 0.96 min (late is eluting diastereomer) (Z018_S04).

Intermediate C.12.1 and Intermediate C.12.2

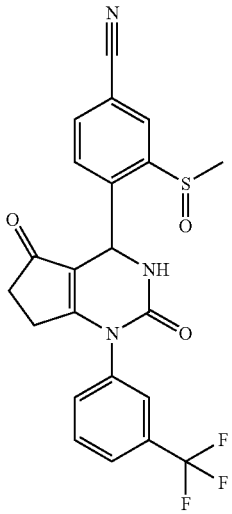 [SMILES: CS(=O)c1cc(C#N)ccc1C1NC(=O)N(c2cccc(C(F)(F)F)c2)C2=C1C(=O)CC2]

4-[2,5-Dioxo-1-(3-trifluoromethyl-phenyl)-2,3,4,5,6,7-hexahydro-1H-cyclopentapyrimidin-4-yl]-3-methanesulfinyl-benzonitrile 3-Chloroperoxybenzoic acid (77%, 51 mg, 0.226 mmol) is added at room temperature to a solution of 4-[2,5-dioxo-1-(3-trifluoromethyl-phenyl)-2,3,4,5,6,7-hexahydro-1H-cyclopentapyrimidin-4-yl]-3-methylsulfanyl-benzonitrile (INTERMEDIATE C.7, 100 mg, 0.226 mmol) in dichloromethane (3 mL) and the mixture is stirred for 20 min. The reaction mixture is concentrated under reduced pressure and purified by reversed phase HPLC (Sunfire, gradient of acetonitrile in water, 0.1% TFA) yielding the two diastereomers.

Intermediate C.12.1

Yield: 35 mg; ESI mass spectrum [M+H]+=460; Retention time HPLC: 0.90 min (early eluting diastereomer) (Z018_S04).

Intermediate C.12.2

Yield: 26 mg; ESI mass spectrum [M+H]+=460; Retention time HPLC: 0.92 min (late is eluting diastereomer) (Z018_S04).

Intermediate C.13

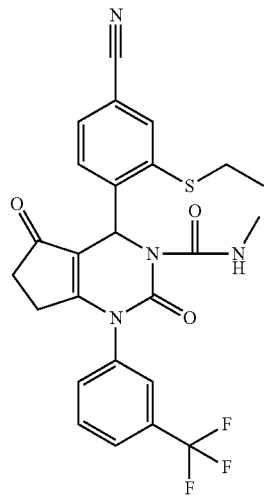 [SMILES: CCSc1cc(C#N)ccc1C1C2=C(CCC2=O)N(c2cccc(C(F)(F)F)c2)C(=O)N1C(=O)NC]

4-(4-Cyano-2-ethylsulfanyl-phenyl)-2,5-dioxo-1-(3-trifluoromethyl-phenyl)-1,2,4,5,6,7-hexahydro-cyclopentapyrimidine-3-carboxylic acid methylamide To a mixture of 4-[2,5-dioxo-1-(3-trifluoromethyl-phenyl)-2,3,4,5,6,7-hexahydro-1H-cyclopentapyrimidin-4-yl]-3-ethylsulfanyl-benzonitrile (INTERMEDIATE C.8; 100 mg; purity 90%; 0.20 mmol) and diisopropylethylamine (130 µL; 0.76 mmol) in acetonitrile (1 mL) is added at room temperature in small portions over a period of 5 h 4-nitrophenylchloroformate (160 mg; 0.79 mmol) and 4-dimethylaminopyridine (140 mg; 1.15 mmol). Methylamine (1M in THF; 1 mL; 1.00 mmol) is added to the mixture containing the 4-nitrophenyl carbamate intermediate and the reaction is stirred at room temperature for 1 h. The reaction mixture is purified by reversed phase HPLC (Sunfire, gradient of acetonitrile in water, 0.1% TFA). Yield: 58 mg. ESI mass spectrum: [M+H]+=515; Retention time HPLC: 1.08 min (Z018_S04).

Intermediate D.1

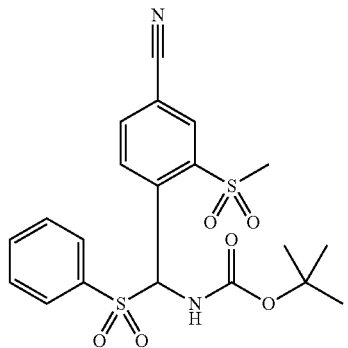 [SMILES: CC(C)(C)OC(=O)NC(c1ccc(C#N)cc1S(C)(=O)=O)S(=O)(=O)c1ccccc1]

[Benzenesulfonyl-(4-cyano-2-methanesulfonyl-phenyl)-methyl]-carbamic acid tert-butyl ester Formic acid (6.2 mL, 164 mmol) is added to a mixture of tert-butyl carbamate (3.05 g, 26.0 mmol), 4-formyl-3-(methylsulfonyl)benzonitrile (preparation according to US 2011/34433, 5.44 g, 26.0 mmol) and sodium benzenesulfinate (4.27 g, 26.0 mmol) in THF (10.0 mL) and water (25.0 mL) and the reaction mixture is stirred at room temperature for 4 days. Water is added and the precipitate is filtered off, washed with water and acetonitrile and dried. Yield: 5.10 g. ESI mass spectrum: [M+H]+=451; Retention time HPLC: 0.59 min (X012_S01).

Intermediate D.2

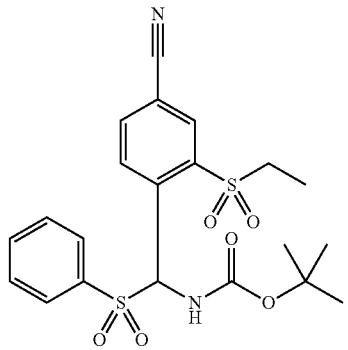 [SMILES: CCS(=O)(=O)c1cc(C#N)ccc1C(NC(=O)OC(C)(C)C)S(=O)(=O)c1ccccc1]

[Benzenesulfonyl-(4-cyano-2-ethanesulfonyl-phenyl)-methyl]-carbamic acid tert-butyl is ester INTERMEDIATE D.2 is prepared in analogous fashion as described for INTERMEDIATE D.1, replacing 4-formyl-3-(methylsulfonyl)benzonitrile with 3-ethanesulfonyl-4-formyl-benzonitrile (preparation according to US 2011/34433). ESI mass spectrum: [M+H]+=465; Retention time HPLC: 1.03 min (Z017_S04).

Intermediate D.3

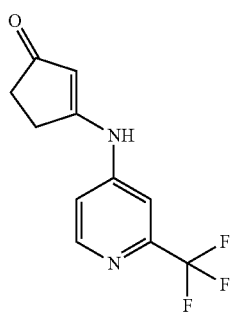 [SMILES: O=C1C=C(Nc2ccnc(C(F)(F)F)c2)CC1]

3-(2-Trifluoromethyl-pyridin-4-ylamino)-cyclopent-2-enone

A solution of 1.3-cyclopentanedione (3.03 g, 30.8 mmol) and 4-amino-2-trifluoromethylpyridine (5.00 g, 30.8 mmol) in acetic acid (15.0 mL) is stirred at 130° C. in a microwave oven for 5 h. The reaction mixture is diluted with methanol and water and purified by reversed phase HPLC (Waters SunFire™-$C_{18}$, gradient of acetonitrile in water, 0.1% formic acid). Yield: 4.52 g; ESI mass spectrum $[M+H]^+$=243; Retention time HPLC: 0.77 min (Z018_S04).

INTERMEDIATES D.3.1-D.3.4 are prepared in analogous fashion as described for INTERMEDIATE D.3, employing the appropriate amine as starting material, respectively.

TABLE 1

| INTER-MEDI-ATE | R | MS $[M + H]^+$ | Retention time [min] | HPLC-Method |
| --- | --- | --- | --- | --- |
| D.3.1 | (structure) | 243 | 0.77 | Z018_S04 |
| D.3.2 | (structure) | 243 | 0.86 | Z018_S04 |
| D.3.3 | (structure) | 253 (bromine isotope pattern) | 0.72 | Z018_S04 |
| D.3.4 | (structure) | 209 (chlorine isotope pattern) | 0.68 | Z017_S04 |

Intermediate D.4

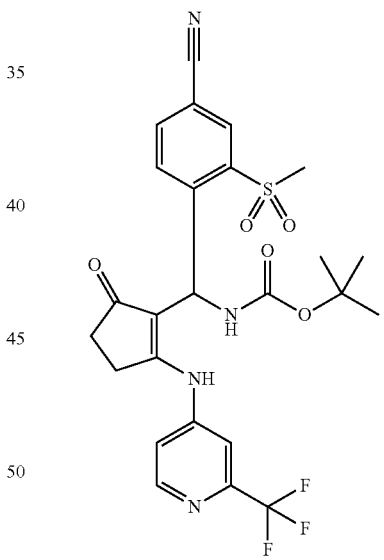

{(4-Cyano-2-methanesulfonyl-phenyl)-[5-oxo-2-(2-trifluoromethyl-pyridin-4-ylamino)-cyclopent-1-enyl]-methyl}-carbamic acid tert-butyl ester Sodium hydride (60% in mineral oil, 515 mg, 12.9 mmol) is added in small portions to a mixture of 3-(2-(trifluoromethyl)pyridin-4-ylamino)cyclopent-2-enone (INTERMEDIATE D.3, 2.60 g, 10.7 mmol) in 2-methyltetrahydrofuran (40.0 mL). After 10 min [benzenesulfonyl-(4-cyano-2-methanesulfonyl-phenyl)-methyl]-carbamic acid tert-butyl ester (INTERMEDIATE D.1, 4.83 g, 10.7 mmol) is added and the reaction mixture is stirred at room temperature for 30 min. Water and ethyl acetate are added and the phases are separated. The organic phase is washed with water and concentrated under reduced pressure. Yield: 6.20 g; ESI mass spectrum [M+H]$^+$=551; Retention time HPLC: 1.12 min (Z018_S04).

INTERMEDIATES D.4.1-D.4.5 are prepared in analogous fashion as described for INTERMEDIATE D.4, employing the starting materials indicated in the following table.

TABLE 2

| INTER-MEDIATE | Starting Materials | Structure | MS [M + H]$^+$ | Retention time [min] | HPLC-Method |
|---|---|---|---|---|---|
| D.4.1 | Intermediates D.2 and D.3 | 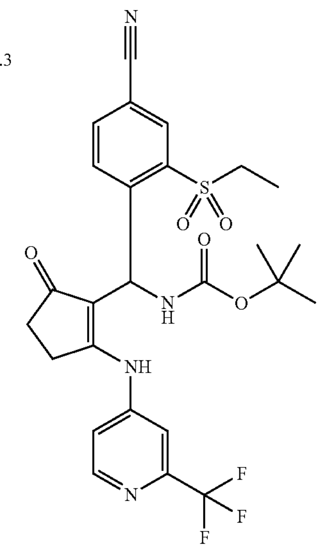 | 565 | 1.15 | Z018_S04 |
| D.4.2 | Intermediates D.1 and D.3.1 | 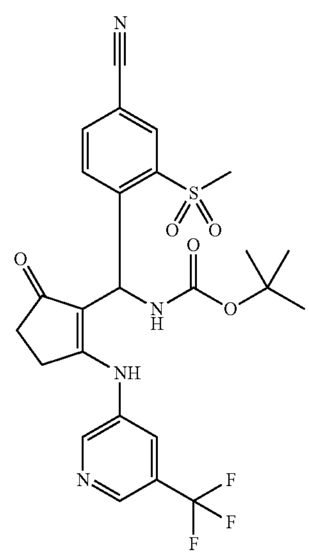 [SMILES: CC(C)(C)OC(=O)NC(C1=C(Nc2cncc(C(F)(F)F)c2)CCC1=O)c1ccc(C#N)cc1S(C)(=O)=O] | 551 | 1.12 | Z018_S04 |

TABLE 2-continued

| INTER-MEDIATE | Starting Materials | Structure | MS [M + H]+ | Retention time [min] | HPLC-Method |
|---|---|---|---|---|---|
| D.4.3 | Intermediates D.1 and D.3.2 | 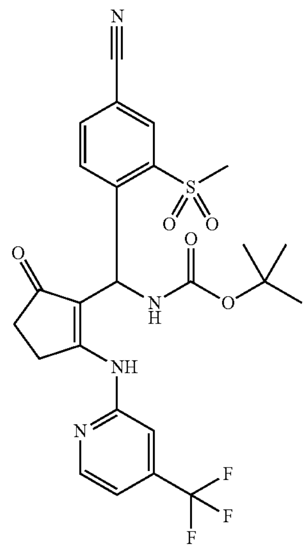 [SMILES: CC(C)(C)OC(=O)NC(C1=C(Nc2cc(C(F)(F)F)ccn2)CCC1=O)c1ccc(C#N)cc1S(C)(=O)=O] | 551 | 1.23 | Z018_S04 |
| D.4.4 | Intermediates D.1 and D.3.3 | 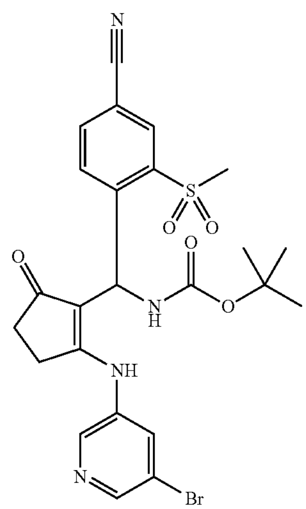 [SMILES: CC(C)(C)OC(=O)NC(C1=C(Nc2cncc(Br)c2)CCC1=O)c1ccc(C#N)cc1S(C)(=O)=O] | 561 (bromine isotope pattern) | 1.08 | Z018_S04 |
| D.4.5 | Intermediates D.1 and D.3.4 | 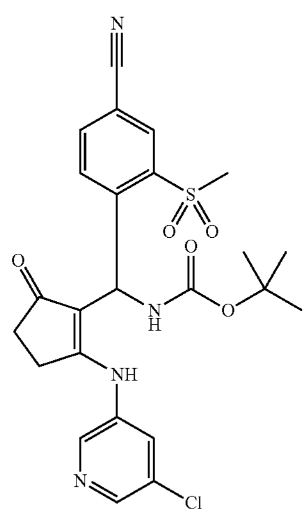 [SMILES: CC(C)(C)OC(=O)NC(C1=C(Nc2cncc(Cl)c2)CCC1=O)c1ccc(C#N)cc1S(C)(=O)=O] | 517 (chlorine isotope pattern) | 1.06 | Z017_S04 |

Intermediate D.5

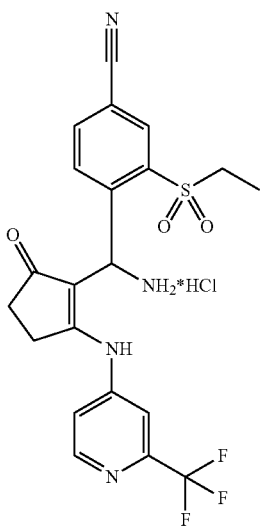

4-{Amino-[5-oxo-2-(2-trifluoromethyl-pyridin-4-ylamino)-cyclopent-1-enyl]-methyl}-3-methanesulfonyl-benzonitrile hydrochloride To a solution of {(4-cyano-2-methanesulfonyl-phenyl)-[5-oxo-2-(2-trifluoromethyl-pyridin-4-ylamino)-cyclopent-1-enyl]-methyl}-carbamic acid tert-butyl ester (INTERMEDIATE D.4, 5.20 g, 9.45 mmol) in 1,4-dioxane (100 mL) is added hydrogen chloride in 1,4-dioxane (4 M, 50.0 mL, 200 mmol) and the mixture is stirred at room temperature overnight. The reaction mixture is diluted with methyl-tert-butylether and the precipitate is filtered off, washed with methyl-tert-butylether and dried. Yield: 4.40 g. ESI mass spectrum: [M+H]$^+$=451; Retention time HPLC: 0.78 min (Z018_S04).

INTERMEDIATES D.5.1-D.5.5 are prepared in analogous fashion as described for INTERMEDIATE D.5, employing the starting materials indicated in the following table.

TABLE 3

| INTER-MEDIATE | Starting Material | Structure | MS [M + H]$^+$ | Retention time [min] | HPLC-Method |
|---|---|---|---|---|---|
| D.5.1 | Intermediate D.4.1 | 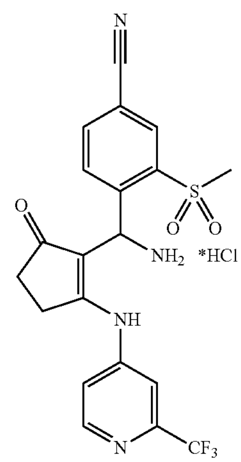 [SMILES: CS(=O)(=O)c1cc(C#N)ccc1C(N)C1=C(Nc2ccnc(C(F)(F)F)c2)CCC1=O] | 465 | 1.82 | Z018_S04 |
| D.5.2 | Intermediate D.4.2 | 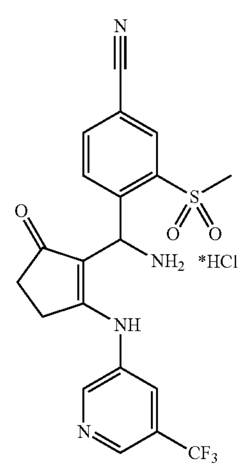 [SMILES: CS(=O)(=O)c1cc(C#N)ccc1C(N)C1=C(Nc2cncc(C(F)(F)F)c2)CCC1=O] | 451 | 0.78 | Z018_S04 |

TABLE 3-continued

| INTER-MEDIATE | Starting Material | Structure | MS [M + H]+ | Retention time [min] | HPLC-Method |
|---|---|---|---|---|---|
| D.5.3 | Intermediate D.4.3 | 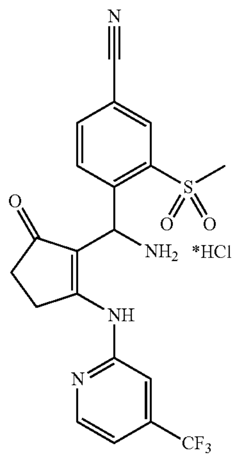 [SMILES: CS(=O)(=O)c1cc(C#N)ccc1C(N)C1=C(Nc2cc(C(F)(F)F)ccn2)CCC1=O] | 451 | 0.84 | Z018_S04 |
| D.5.4 | Intermediate D.4.4 | 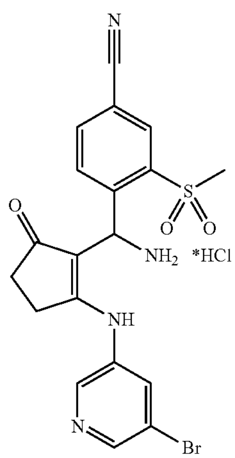 [SMILES: CS(=O)(=O)c1cc(C#N)ccc1C(N)C1=C(Nc2cncc(Br)c2)CCC1=O] | 461 (bromine isotope pattern) | 0.74 | Z018_S04 |
| D.5.5 | Intermediate D.4.5 | 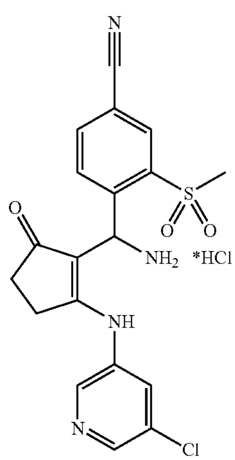 [SMILES: CS(=O)(=O)c1cc(C#N)ccc1C(N)C1=C(Nc2cncc(Cl)c2)CCC1=O] | 417 (chlorine isotope pattern) | 0.74 | Z011_S03 |

Intermediate D.6

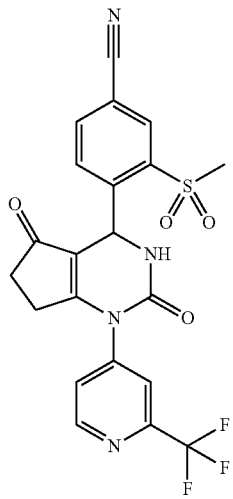 [SMILES: CS(=O)(=O)c1cc(C#N)ccc1C1NC(=O)N(c2ccnc(C(F)(F)F)c2)C2=C1C(=O)CC2]

4-[2,5-Dioxo-1-(2-trifluoromethyl-pyridin-4-yl)-2,3,4,5,6,7-hexahydro-1H-cyclopentapyrimidin-4-yl]-3-methanesulfonyl-benzonitrile To a solution of 4-{amino-[5-oxo-2-(2-trifluoromethyl-pyridin-4-ylamino)-cyclopent-1-enyl]-methyl}-3-methanesulfonyl-benzonitrile hydrochloride (INTERMEDIATE D.5, 4.78 g, 9.81 mmol) in acetonitrile (100 mL) is added 1,1'-carbonyldiimidazole (1.99 g, 12.3 mmol) and triethylamine (0.34 mL, 2.45 mmol) and the mixture is stirred at room temperature for 1 h. The reaction mixture is concentrated under reduced pressure. The residue is treated with water, the precipitate is filtered off, washed with water and dried.

Yield: 3.73 g. ESI mass spectrum: [M+H]$^+$=477; Retention time HPLC: 0.90 min (Z018_S04).

Intermediate D.6A and Intermediate D.6B

Enantiomers of Racemic Intermediate D.6

The enantiomers of racemic INTERMEDIATE D.6 (300 mg, 0.63 mmol) are separated by preparative supercritical fluid chromatography on a chiral phase (Daicel Chiralpak IC, 20×250 mm, 5 μm, 20% MeOH+20 mM ammonia in supercritical CO$_2$, 40° C., 120 bar back pressure).

Intermediate D.6A

Yield: 92 mg; ESI mass spectrum [M+H]$^+$=477; Retention time: 2.67 min (early eluting enantiomer) (I_IB_20_MeOH_NH$_3$).

Intermediate D.6B

Yield: 96 mg; ESI mass spectrum [M+H]$^+$=477; Retention time: 3.03 min (late eluting enantiomer) (I_IB_20_MeOH_NH$_3$).

Intermediate D.7

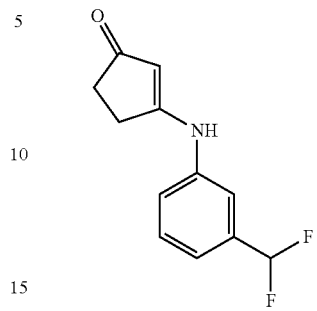

3-(3-(Difluoromethyl)phenylamino)cyclopent-2-enone

A mixture of cyclopentane-1,3-dione (2.00 g, 20.4 mmol), 3-(difluoromethyl)aniline (2.92 g, 20.4 mmol) and ytterbium (III) trifluormethanesulfonate (63 mg, 0.10 mmol) is stirred at room temperature for 2 h. Methanol and water are added and the resulting precipitate is filtered off and dried. Yield: 2.75 g; ESI mass spectrum: [M+H]$^+$=224; Retention time HPLC: 0.82 min (V012_S01).

Intermediate D.8

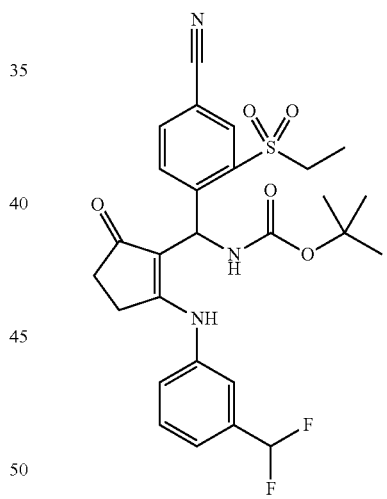

{(4-Cyano-2-ethanesulfonyl-phenyl)-[2-(3-difluoromethyl-phenylamino)-5-oxo-cyclopent-1-enyl]-methyl}-carbamic acid tert-butyl ester Sodium hydride (60% in mineral oil, 155 mg, 3.88 mmol) is added in small portions to a mixture of 3-(3-(difluoromethyl)phenylamino)cyclopent-2-enone (INTERMEDIATE D.7; 936 mg, 4.20 mmol) in 2-methyltetrahydrofuran (10 mL). After 30 min [benzenesulfonyl-(4-cyano-2-ethanesulfonyl-phenyl)-methyl]-carbamic acid tert-butyl ester (INTERMEDIATE D.2, 1.50 g, 3.23 mmol) is added and the mixture is stirred at room temperature overnight. Ethyl acetate and water are added and the phases are separated. The organic phase is washed with water, dried over MgSO$_4$ and concentrated under reduced pressure. Yield: 2.35 g. ESI mass spectrum: $[M+H]^+=546$; Retention time HPLC: 1.14 min (Z017_S04).

Intermediate D.9

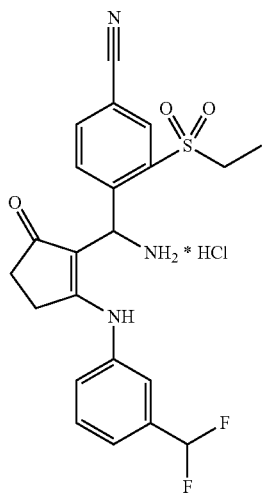

4-{Amino-[2-(3-difluoromethyl-phenylamino)-5-oxo-cyclopent-1-enyl]-methyl}-3-ethanesulfonyl-benzonitrile hydrochloride A solution of hydrogen chloride in 1,4-dioxane (4 M, 3.0 mL, 12.0 mmol) is added to a solution of {(4-cyano-2-ethanesulfonyl-phenyl)-[2-(3-difluoromethyl-phenylamino)-5-oxo-cyclopent-1-enyl]-methyl}-carbamic acid tert-butyl ester (INTERMEDIATE D.8, 2.35 g, purity 75%, 3.23 mmol) in acetonitrile (6 mL) and the mixture is stirred at room temperature for 2 h and then cooled in an ice bath. The precipitate is filtered off, washed with cold acetonitrile and dried. Yield: 1.52 g. ESI mass spectrum: $[M+H]^+=446$; Retention time HPLC: 0.86 min (Z017_S04).

Intermediate E.1

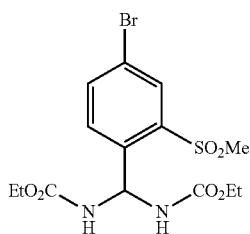 [SMILES: CCOC(=O)NC(NC(=O)OCC)c1ccc(Br)cc1S(C)(=O)=O]

Diethyl(4-bromo-2-methylsulfonyl)phenyl)methyl-enedicarbamate

In a three-necked round bottom flask equipped with a drying tube filled with calcium chloride and an inlet for nitrogen, 4-bromo-2-methanesulfonyl-benzaldehyde (4.50 g, 17.10 mmol) and ethyl carbamate (3.35 g, 37.63 mmol) are heated at 145° C. for 5 h. The flask is being purged with a flow of nitrogen, and concentrated sulfuric acid (ca. 200 μL, ca. 3 mmol) is added slowly drop by drop. After 7 h the solidified reaction mixture is cooled to room temperature, crushed, mixed thoroughly with water and dried. The residue is purified by flash chromatography on silica (gradient dichloromethane to dichloromethane/methanol 95:5). Yield: 5.05 g; ESI mass spectrum: $[M+H]^+=423$ (bromine isotope pattern); Retention time HPLC: 0.77 min (Z011_S03).

Intermediate E.2

4-(4-Bromo-2-methanesulfonyl-phenyl)-1-(3-trifluoromethyl-phenyl)-3,4,6,7-tetrahydro-1H-cyclopentapyrimidine-2,5-dione

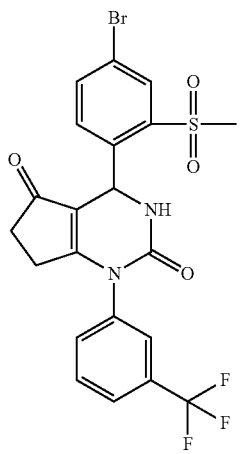 [SMILES: CS(=O)(=O)c1cc(Br)ccc1C1NC(=O)N(c2cccc(C(F)(F)F)c2)C2=C1C(=O)CC2]

Step 1

4-Bromo-1-(chloro(isocyanato)methyl)-2-(methylsulfonyl)benzene

Phosphorous pentachloride (5.47 g, 26.2 mmol) is added to a suspension of diethyl(4-bromo-2-methylsulfonyl)phenyl)methylenedicarbamate (INTERMEDIATE E.1, 5.05 g, 11.9 mmol) in toluene (30 mL) and the mixture is heated at reflux for 3 h. The toluene is evaporated under reduced pressure and the mixture is then purified by distillation under to reduced pressure (ca. 160° C., 0.1 mbar). Yield: 945 mg.

Step 2

4-(4-Bromo-2-methanesulfonyl-phenyl)-1-(3-trifluoromethyl-phenyl)-3,4,6,7-tetrahydro-1H-cyclopentapyrimidine-2,5-dione 3-(3-(Trifluoromethyl)phenylamino)cyclopent-2-enone (234 mg, 0.97 mmol) is added to a solution of 4-bromo-1-(chloro(isocyanato)methyl)-2-(methylsulfonyl)benzene (Step 1, 945 mg, 2.91 mmol) in dichloromethane (10 mL). The mixture is heated at reflux overnight and then concentrated under reduced pressure. The residue is purified by reversed phase HPLC (Agilent ZORBAX™ SB-$C_{18}$, gradient of acetonitrile in water, 0.1% formic acid).

Yield: 110 mg; ESI mass spectrum: $[M+H]^+=529$ (bromine isotope pattern); Retention time HPLC: 1.21 min (Z017_S04).

Intermediate E.3

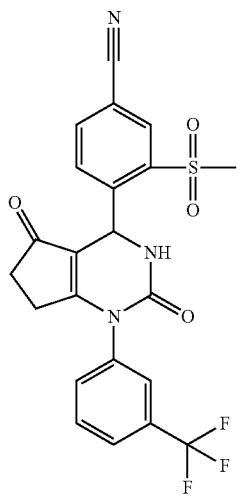 [SMILES: CS(=O)(=O)c1cc(C#N)ccc1C1NC(=O)N(c2cccc(C(F)(F)F)c2)C2=C1C(=O)CC2]

4-(2,5-Dioxo-1-(3-(trifluoromethyl)phenyl)-2,3,4,5,
6,7-hexahydro-1H-cyclopentapyrimidin-4-yl)-3-
(methylsulfonyl)benzonitrile Under an atmosphere of argon, a mixture of 4-(4-bromo-2-(methylsulfonyl)phenyl)-1-(3-(trifluoromethyl)phenyl)-3,4,6,7-tetrahydro-1H-cyclopentapyrimidine-2,5-dione (INTERMEDIATE E.2, 110 mg, 0.21 mmol), zinc cyanide (32 mg, 0.27 mmol) and tetrakis (triphenylphosphine)palladium (0) (24 mg, 21 μmol) in DMF (2 mL) is heated at 110° C. overnight and then cooled to room temperature. Water is added and the mixture is filtered. The precipitate is purified by flash chromatography on silica (gradient cyclohexane/ethyl acetate 8:2 to 3:7). Yield: 40 mg; ESI mass spectrum: $[M+H]^+=476$; Retention time HPLC: 0.94 min (Z017_S04).

Intermediate E.3A and Intermediate E.3B

Enantiomers of Intermediate E.3

The enantiomers of racemic 4-(2,5-dioxo-1-(3-(trifluoromethyl)phenyl)-2,3,4,5,6,7-hexahydro-1H-cyclopentapyrimidin-4-yl)-3-(methylsulfonyl)benzonitrile (INTERMEDIATE E.3, 1.82 g, 3.83 mmol) are separated by preparative supercritical fluid chromatography on a chiral phase (Daicel Chiralpak IB, 20×250 mm, 5 μm, 15% MeOH+0.2% diethylamine in supercritical $CO_2$, 40° C., 120 bar back pressure).

Intermediate E.3A

Yield 620 mg; ESI mass spectrum $[M+H]^+=476$; Retention time: 2.52 min (early eluting enantiomer) (I_IB_20_MeOH_DEA).

Intermediate E.3B

Yield 554 mg; ESI mass spectrum $[M+H]^+=476$; Retention time: 2.78 min (late eluting enantiomer) (I_IB_20_MeOH_DEA).

Intermediate E.4

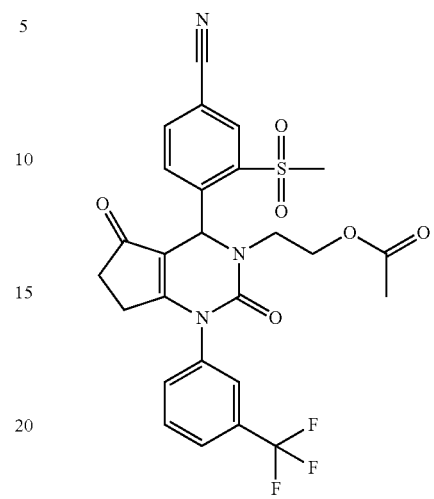

Acetic acid 2-[4-(4-cyano-2-methanesulfonyl-phenyl)-2,5-dioxo-1-(3-trifluoromethyl-phenyl)-1,2,4,5,
6,7-hexahydro-cyclopentapyrimidin-3-yl]-ethyl ester To a mixture of 4-(2,5-dioxo-1-(3-(trifluoromethyl)phenyl)-2,3,4,5,6,7-hexahydro-1H-cyclopentapyrimidin-4-yl)-3-(methylsulfonyl)benzonitrile (INTERMEDIATE E.3, 300 mg, 0.57 mmol) and cesium carbonate (463 mg, 1.42 mmol) in DMF (5.0 mL) is added 2-bromoethylacetate (0.20 mL, 1.82 mmol) and the mixture is stirred at 50° C. for 3 days. The reaction mixture is diluted with acetonitrile and water and purified by reversed phase HPLC (Waters SunFire™-$C_{18}$, gradient of acetonitrile in water, 0.1% TFA). Yield: 104 mg; ESI mass spectrum $[M+H]^+=562$; Retention time HPLC: 1.03 min (Z018_S04).

SYNTHESES OF EXAMPLES

Example A.1

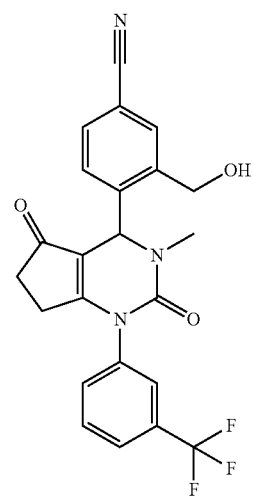 [SMILES: CN1C(=O)N(c2cccc(C(F)(F)F)c2)C2=C(C(=O)CC2)C1c1ccc(C#N)cc1CO]

3-Hydroxymethyl-4-[3-methyl-2,5-dioxo-1-(3-trifluoromethyl-phenyl)-2,3,4,5,6,7-hexahydro-1H-cyclopentapyrimidin-4-yl]-benzonitrile To a solution of 5-cyano-2-[3-methyl-2,5-dioxo-1-(3-trifluoromethyl-phenyl)-2,3,4,5,6,7-hexahydro-1H-cyclopentapyrimidin-4-yl]-benzoic acid (INTERMEDIATE A.6; 700 mg; 1.537 mmol) in THF (10.5 ml) is added 1,1'-carbonyldiimidazole (274 mg; 1.691 mmol). The reaction mixture is stirred at room temperature for 2 h and cooled to 5° C. Sodium borohydride (87 mg; 2.31 mmol) in water (1.4 mL) is added dropwise, keeping the temperature between 5° C. and 10° C. The reaction mixture is stirred for 45 min and quenched with 1M aqueous HCl. Ethyl acetate and water are added and the phases are is separated. The organic layer is washed with water, dried over MgSO$_4$ and concentrated under reduced pressure. The residue is purified by flash chromatography on silica (dichloromethane/methanol 95:5→75:25). Yield: 390 mg; ESI mass spectrum: [M+H]$^+$=442; Retention time HPLC: 0.61 min (X012_S02).

Examples A.1A and A.1B

Enantiomers of Example A.1

The enantiomers of EXAMPLE A.1 (1220 mg) are separated by preparative supercritical fluid chromatography on a chiral phase (Daicel Chiralpak IC, 20×250 mm, 5 µm, 30% MeOH+20 mM ammonia in supercritical CO2, flow 10 mL/min; 150 bar back pressure).

Example A.1A

Yield 330 mg; ESI mass spectrum [M+H]+=442; Retention time: 2.93 min (early eluting enantiomer) (I_IC_40_MEOH_NH3).

Example A.1B

Yield 314 mg; ESI mass spectrum [M+H]+=442; Retention time: 4.54 min (late eluting enantiomer) (I_IC_40_MEOH_NH3).

Example A.2

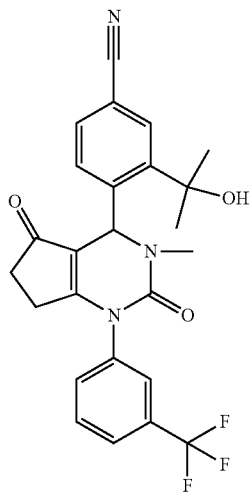 [SMILES: CN1C(=O)N(c2cccc(C(F)(F)F)c2)C2=C(C(=O)CC2)C1c1ccc(C#N)cc1C(C)(C)O]

3-(1-Hydroxy-1-methyl-ethyl)-4-[3-methyl-2,5-dioxo-1-(3-trifluoromethyl-phenyl)-2,3,4,5,6,7-hexahydro-1H-cyclopentapyrimidin-4-yl]-benzonitrile To a solution of 5-cyano-2-[3-methyl-2,5-dioxo-1-(3-trifluoromethyl-phenyl)-2,3,4,5,6,7-hexahydro-1H-cyclopentapyrimidin-4-yl]-benzoic acid methyl ester (INTERMEDIATE A.5; 400 mg; 0.852 mmol) in THF (5 ml) is added a solution of methylmagnesiumchloride is in THF (3M, 625 µL; 1.875 mmol) drop wise at 0° C. The reaction mixture is stirred at room temperature overnight and quenched with 1M HCl. Ethyl acetate and water are added and the phases are separated. The organic layer is washed with water, dried over MgSO$_4$ and concentrated under reduced pressure. The residue is purified by reversed phase HPLC (Waters Xbridge™-C$_{18}$, gradient of acetonitrile in water, 0.1% TFA). Yield: 90 mg; ESI mass spectrum [M+H]+=470; Retention time HPLC: 0.69 min (X012_S02).

Example A.3

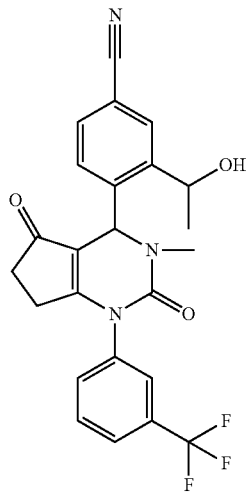 [SMILES: CC(O)c1cc(C#N)ccc1C1C2=C(CCC2=O)N(c2cccc(C(F)(F)F)c2)C(=O)N1C]

3-(1-Hydroxy-ethyl)-4-[3-methyl-2,5-dioxo-1-(3-trifluoromethyl-phenyl)-2,3,4,5,6,7-hexahydro-1H-cyclopentapyrimidin-4-yl]-benzonitrile A solution of methylmagesiumchloride in THF (3M, 0.239 mL; 0.717 mmol) is added at 5° C. to a solution of 3-formyl-4-[3-methyl-2,5-dioxo-1-(3-trifluoromethyl-phenyl)-2,3,4,5,6,7-hexahydro-1H-cyclopentapyrimidin-4-yl]-benzonitrile (INTERMEDIATE A.7, 300 mg; 0.683 mmol) in diethylether (3 mL) and THF (2.5 mL). The reaction mixture is stirred at 0° C. for 15 min and 1 h at room temperature. Water and 1M aqueous HCl are added until the pH is acidic. Ethyl acetate is added and the phases are separated. The organic layer is dried over MgSO$_4$ and concentrated under reduced pressure. The residue is purified by flash chromatography on silica (first run: dichloromethane/methanol 98:2, second run: cyclohexane/ethyl acetate 2:8). Yield: 112 mg; ESI mass spectrum: [M+H]$^+$=456; Retention time HPLC: 0.62 min (X012_S02).

Example B.1

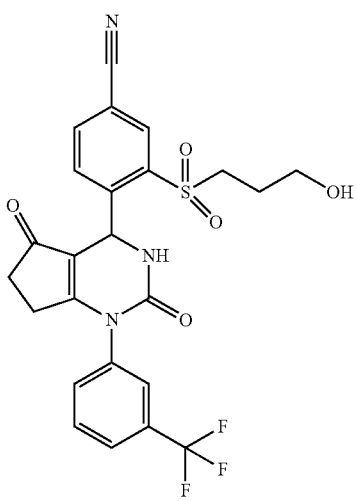 [SMILES: N#Cc1ccc(C2NC(=O)N(c3cccc(C(F)(F)F)c3)C3=C2C(=O)CC3)c(S(=O)(=O)CCCO)c1]

4-[2,5-Dioxo-1-(3-trifluoromethyl-phenyl)-2,3,4,5,6,7-hexahydro-1H-cyclopentapyrimidin-4-yl]-3-(3-hydroxy-propane-1-sulfonyl)-benzonitrile To a solution of 4-[2,5-dioxo-1-(3-trifluoromethyl-phenyl)-2,3,4,5,6,7-hexahydro-1H-cyclopentapyrimidin-4-yl]-3-(3-hydroxy-propylsulfanyl)-benzonitrile (INTERMEDIATE B.4, 13 mg, 0.027 mmol) in dichloromethane (2.0 mL) is added 3-chloroperoxybenzoic acid (40 mg, 0.18 mmol) and the mixture is stirred at room temperature for 20 min. The reaction mixture is concentrated under reduced pressure and purified by reversed phase HPLC (Agilent ZORBAX™ SB-$C_{18}$, gradient of acetonitrile in water, 0.1% TFA). Yield: 5 mg. ESI mass spectrum: [M+H]+=520; Retention time HPLC: 0.93 min (Z018_S04).

The following EXAMPLES B.1.1-B.1.4 are prepared in analogous fashion as described for EXAMPLE B.1, employing the starting materials indicated in the following table.

TABLE 4

| EXAMPLE | Starting Material | Structure | MS [M + H]+ | Retention time [min] | HPLC-Method |
|---|---|---|---|---|---|
| B.1.1 | Intermediate B.4.1 | 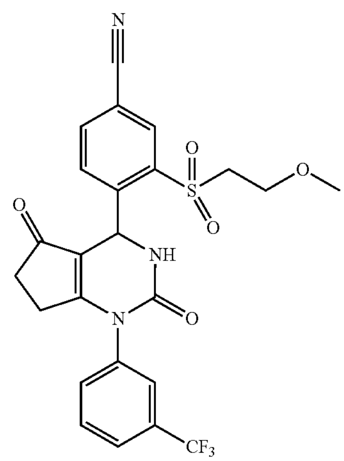 [SMILES: COCCS(=O)(=O)c1cc(C#N)ccc1C1NC(=O)N(c2cccc(C(F)(F)F)c2)C2=C1C(=O)CC2] | 520 | 0.99 | Z018_S04 |
| B.1.2 | Intermediate B.6 | 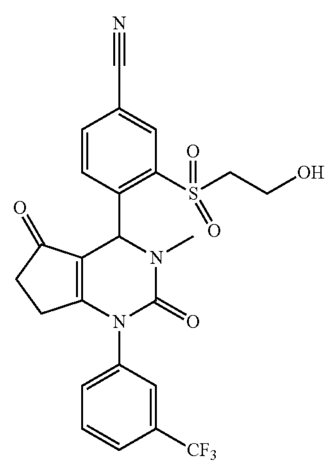 [SMILES: CN1C(=O)N(c2cccc(C(F)(F)F)c2)C2=C(C(=O)CC2)C1c1ccc(C#N)cc1S(=O)(=O)CCO] | 520 | 0.96 | Z018_S04 |

TABLE 4-continued

| EXAMPLE | Starting Material | Structure | MS [M + H]+ | Retention time [min] | HPLC-Method |
|---|---|---|---|---|---|
| B.1.3 | Intermediate B.6.1 | 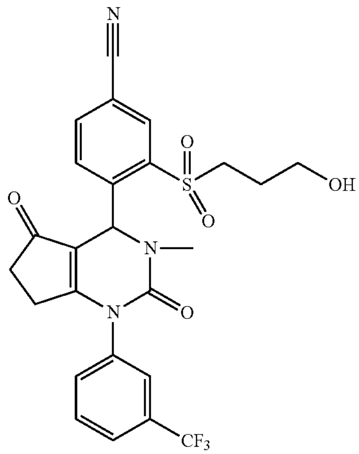 [SMILES: CN1C(=O)N(c2cccc(C(F)(F)F)c2)C2=C(C(=O)CC2)C1c1ccc(C#N)cc1S(=O)(=O)CCCO] | 534 | 0.99 | Z018_S04 |
| B.1.4 | Intermediate B.6.2 | 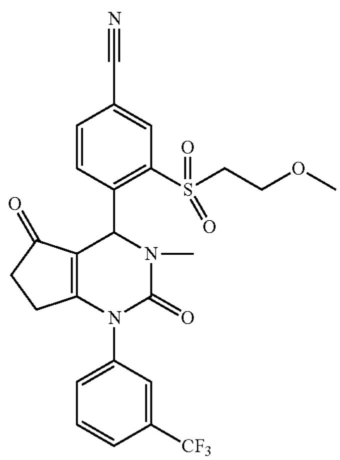 [SMILES: COCCS(=O)(=O)c1cc(C#N)ccc1C1C2=C(CCC2=O)N(c2cccc(C(F)(F)F)c2)C(=O)N1C] | 534 | 1.04 | Z018_S04 |

Example B.1.2A and Example B.1.2B

Enantiomers of Example B.1.2

The enantiomers of EXAMPLE B.1.2 (142 mg) are separated by preparative supercritical fluid chromatography on a chiral phase (Daicel Chiralpak IB, 10×250 mm, 5 μm, 20% MeOH+20 mM NH₃ in supercritical CO₂, flow 10 mL/min, 120 bar back pressure, 40° C.).

Example B.1.2A

Yield 65 mg; ESI mass spectrum [M+H]⁺=520; Retention time: 2.15 min (early eluting enantiomer) (I_IB_20_MEOH_NH3).

Example B.1.2B

Yield 63 mg; ESI mass spectrum [M+H]⁺=520; Retention time: 2.77 min (late eluting enantiomer) (I_IB_20_MEOH_NH3).

An x-ray structure of EXAMPLE B.1.2B bound to neutrophil elastase revealed the following structure and configuration at the carbon marked with an asterisk:

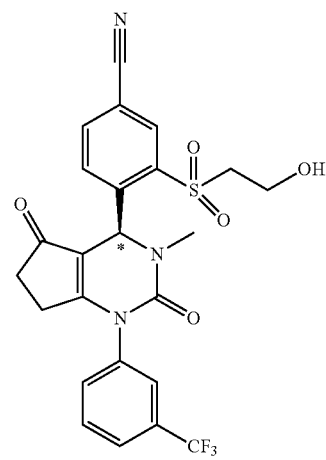 [SMILES: CN1C(=O)N(c2cccc(C(F)(F)F)c2)C2=C(C(=O)CC2)[C@H]1c1ccc(C#N)cc1S(=O)(=O)CCO]

Example B.1.3A and Example B.1.3B

Enantiomers of Example B.1.3

The enantiomers of EXAMPLE B.1.3 (120 mg) are separated by preparative supercritical fluid chromatography on a chiral phase (Daicel Chiralpak IB, 20×250 mm, 5 μm, 15% MeOH+20 mM $NH_3$ in supercritical $CO_2$, flow 60 mL/min, 150 bar back pressure, 40° C.).

Example B.1.3A

Yield 60 mg; ESI mass spectrum $[M+H]^+$=534; Retention time: 2.03 min (early eluting enantiomer) (I_IB_20_MEOH_NH3).

Example B.1.3B

Yield 54 mg; ESI mass spectrum $[M+H]^+$=534; Retention time: 2.27 min (late eluting enantiomer) (I_IB_20_MEOH_NH3).

Example C.1A and Example C.1B

Enantiomers of Intermediate C.11.1

The enantiomers of INTERMEDIATE C.11.1 (early eluting diastereomer, 490 mg, 1.035 mmol) are separated by preparative supercritical fluid chromatography on a chiral phase (Daicel Chiralpak IB, 10×250 mm, 5 μm, 20% MeOH+20 mM $NH_3$ in supercritical $CO_2$, flow 10 mL/min, 120 bar back pressure).

Example C.1A

Yield 167 mg; ESI mass spectrum $[M+H]^+$=474; Retention time: 2.83 min (early eluting enantiomer) (I_IB_20_MEOH_NH3).

Example C.1B

Yield 170 mg; ESI mass spectrum $[M+H]^+$=474; Retention time: 3.25 min (late eluting enantiomer) (I_IB_20_MEOH_NH3).

An x-ray structure of EXAMPLE C.1B bound to neutrophil elastase revealed the following structure and configuration at the carbon marked with an asterisk:

Example C.1B

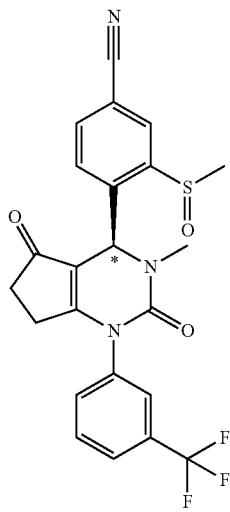 [SMILES: CN1C(=O)N(c2cccc(C(F)(F)F)c2)C2=C(C(=O)CC2)[C@H]1c1ccc(C#N)cc1S(C)=O]

Example C.2A and Example C.2B

Enantiomers of Intermediate C.11.2

The enantiomers of INTERMEDIATE C.11.2 (late eluting diastereomer, 317 mg, 0.670 is mmol) are separated by preparative supercritical fluid chromatography on a chiral phase (Daicel Chiralpak IA, 20% MeOH+20 mM $NH_3$ in supercritical $CO_2$, flow 60 mL/min, 150 bar back pressure).

Example C.2A

Yield 126 mg; ESI mass spectrum $[M+H]^+$=474; Retention time: 1.58 min (early eluting enantiomer) (I_IA_20_MEOH_NH3).

Example C.2B

Yield 126 mg; ESI mass spectrum $[M+H]^+$=474; Retention time: 2.33 min (late eluting enantiomer) (I_IA_20_MEOH_NH3).

An x-ray structure of EXAMPLE C.2A bound to neutrophil elastase revealed the following structure and configuration at the carbon marked with an asterisk:

Example C.2A

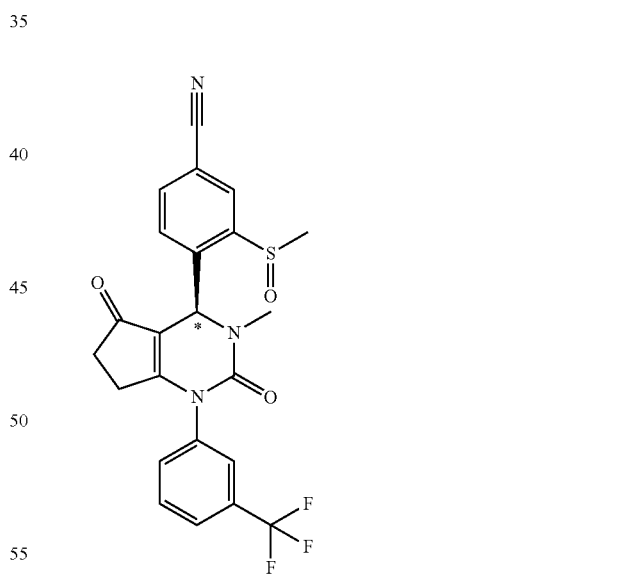

Thus, EXAMPLE C.1B and EXAMPLE C.2A have the same configuration at the carbon marked with an asterisk and differ with respect to the configuration of the sulfur atom. Therefore, EXAMPLE C.1B and EXAMPLE C.2A are diastereomers.

Example C.3

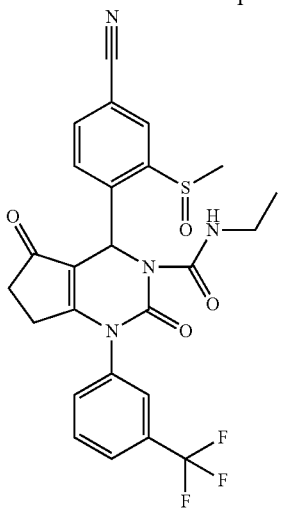

4-(4-Cyano-2-methanesulfinyl-phenyl)-2,5-dioxo-1-(3-trifluoromethyl-phenyl)-1,2,4,5,6,7-hexahydro-cyclopentapyrimidine-3-carboxylic acid ethylamide To a mixture of 4-[2,5-dioxo-1-(3-trifluoromethyl-phenyl)-2,3,4,5,6,7-hexahydro-1H-cyclopentapyrimidin-4-yl]-3-methanesulfinyl-benzonitrile (INTERMEDIATE C.12.2, late eluting diastereomer, 26 mg; 0.057 mmol), diisopropylethylamine (38 µL; 0.23 mmol) and 4-dimethylaminopyridine (8 mg; 0.06 mmol) in acetonitrile (3 mL) is added 4-nitrophenylchloroformate (12.6 mg; 0.062 mmol) at room temperature and the reaction mixture is stirred for 5 h. Ethylamine (2M in THF; 114 µL; 0.228 mmol) is added to the reaction mixture containing the 4-nitrophenyl carbamate intermediate and the mixture is stirred at room temperature for 1 h. The reaction mixture is purified by reversed phase HPLC (Sunfire, gradient of acetonitrile in water, 0.1% TFA). Yield: 4 mg. ESI mass spectrum: [M+H]$^+$=531; Retention time HPLC: 1.02 min (Z018_S04).

Example C.4.1 and Example C.4.2

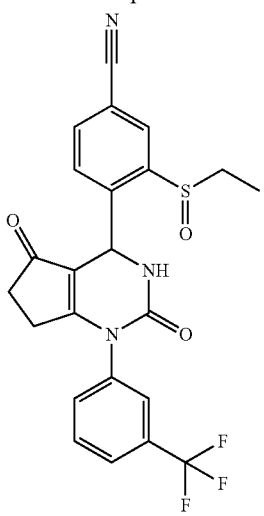

4-[2,5-Dioxo-1-(3-trifluoromethyl-phenyl)-2,3,4,5,6,7-hexahydro-1H-cyclopentapyrimidin-4-yl]-3-ethanesulfinyl-benzonitrile 3-Chloroperoxybenzoic acid (77%, 45 mg, 0.201 mmol) is added at room temperature to a solution of 4-[2,5-dioxo-1-(3-trifluoromethyl-phenyl)-2,3,4,5,6,7-hexahydro-1H-cyclopentapyrimidin-4-yl]-3-ethylsulfanyl-benzonitrile (INTERMEDIATE C.8, 106 mg, is 0.210 mmol) in dichloromethane (2 mL), and the mixture is stirred for 20 min. The reaction mixture is concentrated under reduced pressure and purified by reversed phase HPLC (Sunfire, gradient of acetonitrile in water, 0.1% TFA) yielding the two diastereomers.

Example C.4.1

Yield: 15 mg; ESI mass spectrum [M+H]$^+$=474; Retention time HPLC: 0.91 min (early eluting diastereomer) (Z018_S04).

Example C.4.2

Yield: 32 mg; ESI mass spectrum [M+H]$^+$=474; Retention time HPLC: 0.93 min (late eluting diastereomer) (Z018_S04).

Example C.5.1 and Example C.5.2

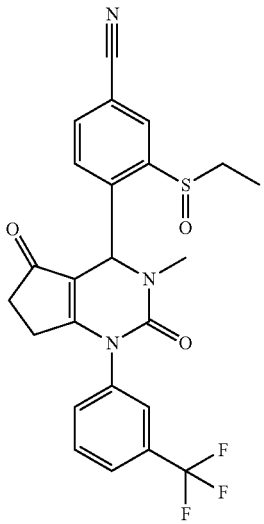 [SMILES: CCS(=O)c1cc(C#N)ccc1C1C2=C(CCC2=O)N(c2cccc(C(F)(F)F)c2)C(=O)N1C]

3-Ethanesulfinyl-4-[3-methyl-2,5-dioxo-1-(3-trifluoromethyl-phenyl)-2,3,4,5,6,7-hexahydro-1H-cyclopentapyrimidin-4-yl]-benzonitrile 3-Chloroperoxybenzoic acid (77%, 24 mg, 0.107 mmol) is added at room temperature to a solution of 4-[3-methyl-2,5-dioxo-1-(3-trifluoromethyl-phenyl)-2,3,4,5,6,7-hexahydro-1H-cyclopentapyrimidin-4-yl]-3-ethylsulfanyl-benzonitrile (INTERMEDIATE C.10, 53 mg, 0.112 mmol) in dichloromethane (1 mL) and the mixture is stirred for 20 min. The reaction to mixture is concentrated under reduced pressure, and the residue is purified by reversed phase HPLC (Sunfire, gradient of acetonitrile in water, 0.1% TFA) yielding the two diastereomers.

Example C.5.1

Yield: 26 mg; ESI mass spectrum [M+H]+=488; Retention time HPLC: 0.96 min (early is eluting diastereomer) (Z018_S04).

Example C.5.2

Yield: 17 mg; ESI mass spectrum [M+H]$^+$=488; Retention time HPLC: 0.97 min (late eluting diastereomer) (Z018_S04).

Example C.6.1 and Example C.6.2

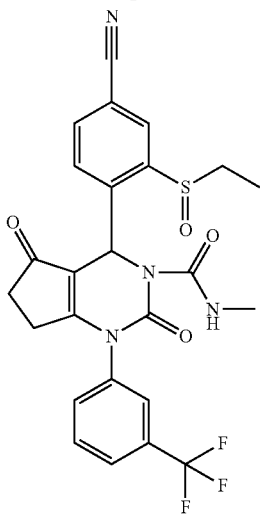 [SMILES: CCS(=O)c1cc(C#N)ccc1C1C2=C(CCC2=O)N(c2cccc(C(F)(F)F)c2)C(=O)N1C(=O)NC]

4-(4-Cyano-2-ethanesulfinyl-phenyl)-2,5-dioxo-1-(3-trifluoromethyl-phenyl)-1,2,4,5,6,7-hexahydro-cyclopentapyrimidine-3-carboxylic acid methylamide 3-Chloroperoxybenzoic acid (77%, 24 mg, 0.107 mmol) is added at room temperature to a solution of 4-(4-cyano-2-ethylsulfanyl-phenyl)-2,5-dioxo-1-(3-trifluoromethyl-phenyl)-1,2,4,5,6,7-hexahydro-cyclopentapyrimidine-3-carboxylic acid methylamide (INTERMEDIATE C.13, 58 mg, 0.113 mmol) in dichloromethane (2 mL), and the mixture is stirred for 20 min. The reaction mixture is concentrated under reduced pressure, and the residue is purified by reversed phase HPLC (Sunfire, gradient of acetonitrile in water, 0.1% TFA) yielding the two diastereomers.

Example C.6.1

Yield: 7 mg; ESI mass spectrum $[M+H]^+=531$; Retention time HPLC: 0.98 min (early eluting diastereomer) (Z018_S04).

Example C.6.2

Yield: 15 mg; ESI mass spectrum $[M+H]^+=531$; Retention time HPLC: 1.00 min (late eluting diastereomer) (Z018_S04).

Example D.1A (Enantiomer 1)

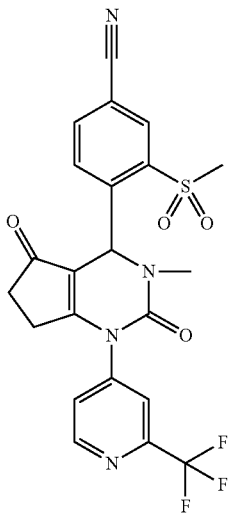

3-Methanesulfonyl-4-[3-methyl-2,5-dioxo-1-(2-trifluoromethyl-pyridin-4-yl)-2,3,4,5,6,7-hexahydro-1H-cyclopentapyrimidin-4-yl]-benzonitrile To a mixture of 4-[2,5-dioxo-1-(2-trifluoromethyl-pyridin-4-yl)-2,3,4,5,6,7-hexahydro-1H-cyclopentapyrimidin-4-yl]-3-methanesulfonyl-benzonitrile (INTERMEDIATE D.6A, early eluting enantiomer, 92 mg, 0.19 mmol) and cesium carbonate (126 mg, 0.39 mmol) in DMF (3.0 mL) is added a solution of methyl iodide in methyl-tert-butylether (c=2 mol/L, 116 µL, 0.23 mmol) and the mixture is stirred at room temperature for 5 h. Ice is added to the reaction mixture, the mixture is acidified with trifluoroacetic acid and purified by to reversed phase HPLC (Waters SunFire™-$C_{18}$, gradient of acetonitrile in water, 0.1% TFA).

Yield: 54 mg; ESI mass spectrum $[M+H]^+=491$; Retention time HPLC: 0.98 min (Z018_S04). As the starting material is enantiopure, it is assumed that EXAMPLE D.1A is enantiopure and has the same configuration as the starting material.

Example D.1B (Enantiomer 2)

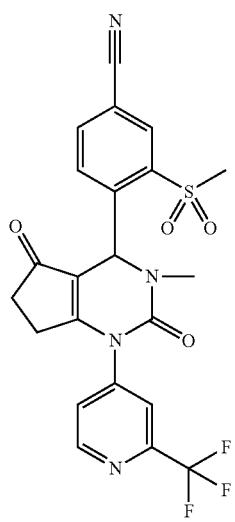

3-Methanesulfonyl-4-[3-methyl-2,5-dioxo-1-(2-trifluoromethyl-pyridin-4-yl)-2,3,4,5,6,7-hexahydro-1H-cyclopentapyrimidin-4-yl]-benzonitrile EXAMPLE D.1B is prepared in analogous fashion as described for EXAMPLE D.1A, replacing INTERMEDIATE D.6A (early eluting enantiomer) with INTERMEDIATE D.6B (late eluting enantiomer) as starting material. ESI mass spectrum $[M+H]^+=491$; Retention time HPLC: 0.98 min (Z018_S04). EXAMPLE D.1B is the enantiomer of EXAMPLE D.1A. As the starting material is enantiopure, it is assumed that EXAMPLE D.1B is enantiopure and has the same configuration as the starting material.

Example D.2

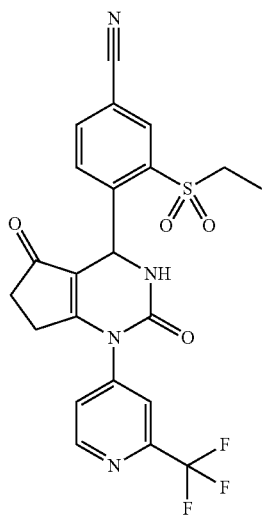 [SMILES: CCS(=O)(=O)c1cc(C#N)ccc1C1NC(=O)N(c2ccnc(C(F)(F)F)c2)C2=C1C(=O)CC2]

4-[2,5-Dioxo-1-(2-trifluoromethyl-pyridin-4-yl)-2,3,4,5,6,7-hexahydro-1H-cyclopentapyrimidin-4-yl]-3-ethanesulfonyl-benzonitrile To a solution of 4-{amino-[5-oxo-2-(2-trifluoromethyl-pyridin-4-ylamino)-cyclopent-1-en yl]-methyl}-3-ethanesulfonyl-benzonitrile hydrochloride (INTERMEDIATE D.5.1, 706 mg, 1.41 mmol) and triethylamine (50 μL, 0.36 mmol) in acetonitrile (3.0 mL) is added 1,1'-carbonyldiimidazole (260 mg, 1.60 mmol) and the mixture is stirred at room temperature for 15 min. The reaction mixture is concentrated under reduced pressure and purified by reversed phase HPLC (Waters SunFire™-$C_{18}$, gradient of acetonitrile in water, 0.1% formic acid). Yield: 562 mg; ESI mass spectrum [M+H]+=491; Retention time HPLC: 0.94 min (Z018_S04).

EXAMPLES D.2.1-D.2.4 are prepared in analogous fashion as described for EXAMPLE D.2, employing the starting materials indicated in the following table, respectively.

TABLE 5

| Example | Starting Material | Structure | MS [M + H]+ | Retention time [min] | HPLC-Method |
|---|---|---|---|---|---|
| D.2.1 | Intermediate D.5.2 | 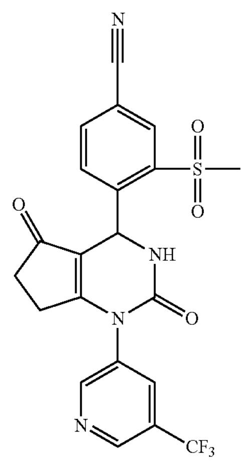 [SMILES: CS(=O)(=O)c1cc(C#N)ccc1C1NC(=O)N(c2cncc(C(F)(F)F)c2)C2=C1C(=O)CC2] | 477 | 0.89 | Z018_S04 |
| D.2.2 | Intermediate D.5.3 | 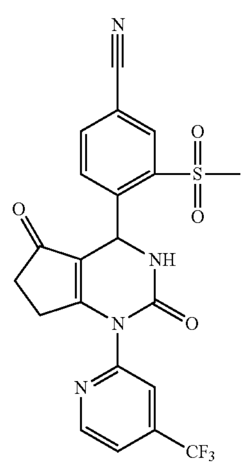 [SMILES: CS(=O)(=O)c1cc(C#N)ccc1C1NC(=O)N(c2cc(C(F)(F)F)ccn2)C2=C1C(=O)CC2] | 477 | 0.91 | Z018_S04 |

TABLE 5-continued

| Example | Starting Material | Structure | MS [M + H]+ | Retention time [min] | HPLC-Method |
|---|---|---|---|---|---|
| D.2.3 | Intermediate D.5.4 | 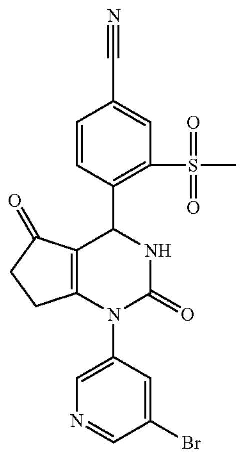 [SMILES: CS(=O)(=O)c1cc(C#N)ccc1C1NC(=O)N(c2cncc(Br)c2)C2=C1C(=O)CC2] | 487 (bromine isotope pattern) | 0.85 | Z018_S04 |
| D.2.4 | Intermediate D.5.5 | 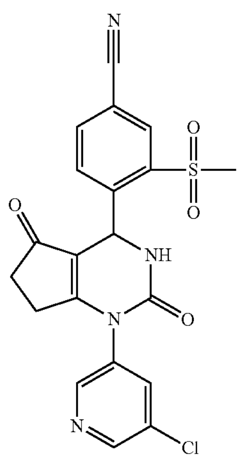 [SMILES: CS(=O)(=O)c1cc(C#N)ccc1C1NC(=O)N(c2cncc(Cl)c2)C2=C1C(=O)CC2] | 443 (chlorine isotope pattern) | 0.62 | 005_CA07 |

Example D.3

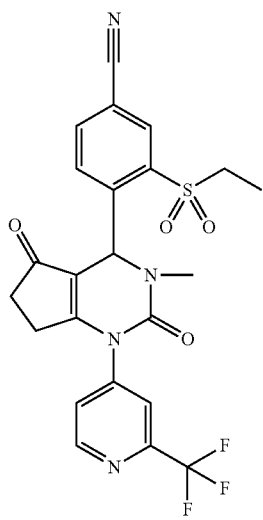 [SMILES: CCS(=O)(=O)c1cc(C#N)ccc1C1C2=C(CCC2=O)N(c2ccnc(C(F)(F)F)c2)C(=O)N1C]

3-Ethanesulfonyl-4-[3-methyl-2,5-dioxo-1-(2-trifluoromethyl-pyridin-4-yl)-2,3,4,5,6,7-hexahydro-1H-cyclopentapyrimidin-4-yl]-benzonitrile A solution of methyliodide in methyl-tert-butylether (c=2 mol/L, 97 µL, 0.19 mmol) is added to a mixture of 4-[2,5-dioxo-1-(2-trifluoromethyl-pyridin-4-yl)-2,3,4,5,6,7-hexahydro-1H-cyclopentapyrimidin-4-yl]-3-ethanesulfonyl-benzonitrile (EXAMPLE D.2, 80 mg, 0.16 mmol) and cesium carbonate (97 mg, 0.30 mmol) in DMF (1.0 mL) and the mixture is stirred at room temperature overnight. The reaction mixture is acidified with acetic acid and purified by reversed phase HPLC (Waters SunFire™-C$_{18}$, gradient of acetonitrile in water, 0.1% TFA). Yield: 63 mg. ESI mass spectrum: [M+H]+=505; Retention time HPLC: 1.02 min (Z018_S04).

Example D.3A and Example D.3B

Enantiomers of Example D.3

The enantiomers of racemic 3-ethanesulfonyl-4-[3-methyl-2,5-dioxo-1-(2-trifluoromethyl-pyridin-4-yl)-2,3,4,5,6,7-hexahydro-1H- cyclopentapyrimidin-4-yl]-benzonitrile (EXAMPLE D.3, 104 mg, 0.206 mmol) are separated by preparative supercritical fluid chromatography on a chiral phase (Daicel Chiralpak IC, 10×250 mm, 5 μm, 30% MeOH+20 mM $NH_3$ in supercritical $CO_2$, 40° C., 120 bar back pressure).

Example D.3A

Yield 45 mg; ESI mass spectrum $[M+H]^+$=505; Retention time: 1.94 min (early eluting enantiomer) (I_IC_30_MeOH_$NH_3$).

Example D.3B

Yield 47 mg; ESI mass spectrum $[M+H]^+$=505; Retention time: 2.36 min (late eluting enantiomer) (I_IC_30_MeOH_$NH_3$).

EXAMPLES D.3.1-D.3.4 are prepared in analogous fashion as described for EXAMPLE D.3, employing the starting materials indicated in the following table, respectively.

TABLE 6

| Example | Starting Material | Structure | MS $[M + H]^+$ | Retention time [min] | HPLC-Method |
|---|---|---|---|---|---|
| D.3.1 | EXAMPLE D.2.1 | 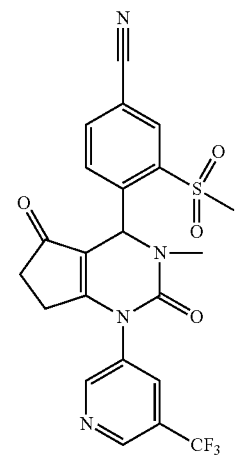 [SMILES: CN1C(=O)N(c2cncc(C(F)(F)F)c2)C2=C(C(=O)CC2)C1c1ccc(C#N)cc1S(C)(=O)=O] | 491 | 0.97 | Z018_S04 |
| D.3.2 | EXAMPLE D.2.2 | 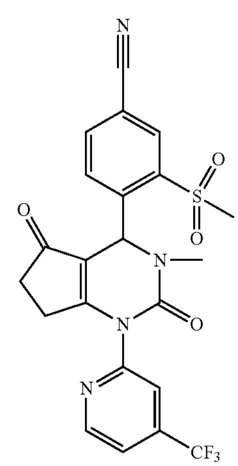 [SMILES: CN1C(=O)N(c2cc(C(F)(F)F)ccn2)C2=C(C(=O)CC2)C1c1ccc(C#N)cc1S(C)(=O)=O] | 491 | 0.99 | Z018_S04 |

TABLE 6-continued

| Example | Starting Material | Structure | MS [M + H]+ | Retention time [min] | HPLC-Method |
|---|---|---|---|---|---|
| D.3.3 | EXAMPLE D.2.3 | 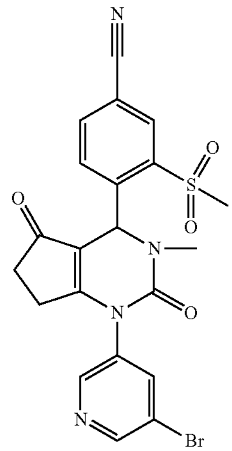 [SMILES: CN1C(=O)N(c2cncc(Br)c2)C2=C(C(=O)CC2)C1c1ccc(C#N)cc1S(C)(=O)=O] | 501 (bromine isotope pattern) | 0.94 | Z018_S04 |
| D.3.4 | EXAMPLE D.2.4 | 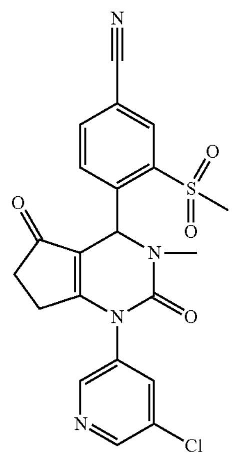 [SMILES: CN1C(=O)N(c2cncc(Cl)c2)C2=C(C(=O)CC2)C1c1ccc(C#N)cc1S(C)(=O)=O] | 457 (chlorine isotope pattern) | 0.91 | Z017_S04 |

Example D.4

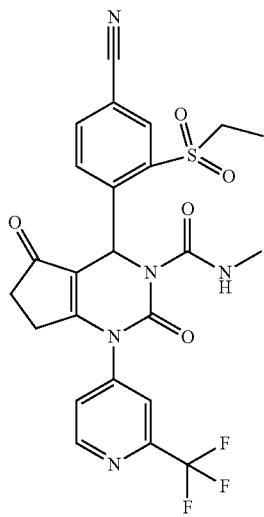 [SMILES: CCS(=O)(=O)c1cc(C#N)ccc1C1C2=C(CCC2=O)N(c2ccnc(C(F)(F)F)c2)C(=O)N1C(=O)NC]

4-(4-Cyano-2-ethanesulfonyl-phenyl)-2,5-dioxo-1-(2-trifluoromethyl-pyridin-4-yl)-1,2,4,5,6,7-hexahydro-cyclopentapyrimidine-3-carboxylic acid methylamide A mixture of 4-[2,5-dioxo-1-(2-trifluoromethyl-pyridin-4-yl)-2,3,4,5,6,7-hexahydro-1H-cyclopentapyrimidin-4-yl]-3-ethanesulfonyl-benzonitrile (EXAMPLE D.2, 80 mg, 0.16 mmol), 4-nitrophenyl chloroformate (100 mg, 0.50 mmol), 4-dimethylaminopyridine (70 mg, 0.57 mmol) and diisopropylethylamine (0.12 mL, 0.71 mmol) in acetonitrile (1.0 mL) is stirred at room temperature overnight. Methylamine (c=2 mol/L, 1.0 mL; 2.00 mmol) is added to the mixture containing the 4-nitrophenyl carbamate intermediate and the mixture is stirred at room temperature for 2 h. The reaction mixture is acidified with acetic acid and purified by reversed phase HPLC (Waters SunFire™-$C_{18}$, gradient of acetonitrile in water, 0.1% TFA). Yield: 43 mg. ESI mass spectrum: [M+H]+=548; Retention time HPLC: 0.99 min (Z018_S04).

EXAMPLES D.4.1-D.4.10 are prepared in analogous fashion as described for EXAMPLE D.4, employing the starting materials indicated in the following table, respectively.

TABLE 7
| EXAMPLE | Starting Material | Structure | MS [M + H]+ | Retention time [min] | HPLC-Method |
|---|---|---|---|---|---|
| D.4.1 | EXAMPLE D.2 (ethyl amine instead of methyl amine) | 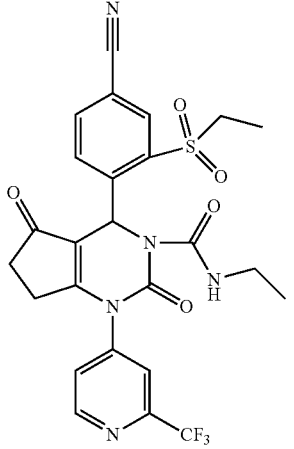 [SMILES: CCNC(=O)N1C(=O)N(c2ccnc(C(F)(F)F)c2)C2=C(C(=O)CC2)C1c1ccc(C#N)cc1S(=O)(=O)CC] | 562 | 1.03 | Z018_S04 |
| D.4.2 | EXAMPLE D.2.1 | 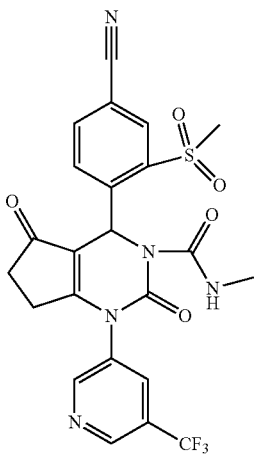 [SMILES: CNC(=O)N1C(=O)N(c2cncc(C(F)(F)F)c2)C2=C(C(=O)CC2)C1c1ccc(C#N)cc1S(C)(=O)=O] | 534 | 0.95 | Z018_S04 |
| D.4.3 | EXAMPLE D.2.1 (ethyl amine instead of methyl amine) | 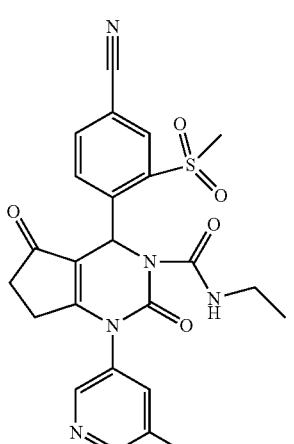 | 548 | 1.05 | Z018_S04 |

TABLE 7-continued
| EXAMPLE | Starting Material | Structure | MS [M + H]+ | Retention time [min] | HPLC-Method |
|---|---|---|---|---|---|
| D.4.4 | EXAMPLE D.2.2 | 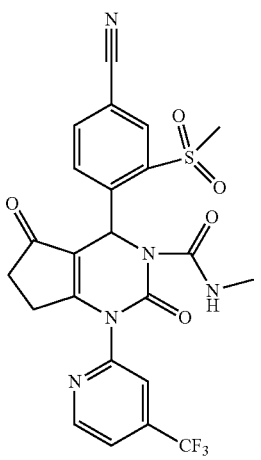 [SMILES: CNC(=O)N1C(=O)N(c2cc(C(F)(F)F)ccn2)C2=C(C(=O)CC2)C1c1ccc(C#N)cc1S(C)(=O)=O] | 534 | 0.97 | Z018_S04 |
| D.4.5 | EXAMPLE D.2.2 (ethyl amine instead of methyl amine) | 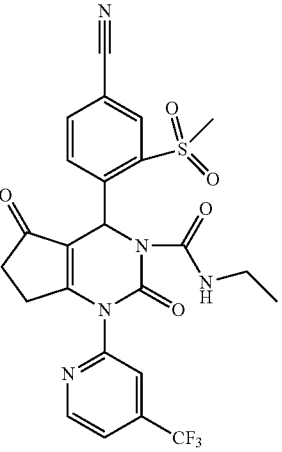 [SMILES: CCNC(=O)N1C(=O)N(c2cc(C(F)(F)F)ccn2)C2=C(C(=O)CC2)C1c1ccc(C#N)cc1S(C)(=O)=O] | 548 | 1.01 | Z018_S04 |
| D.4.6 | EXAMPLE D.2.3 | 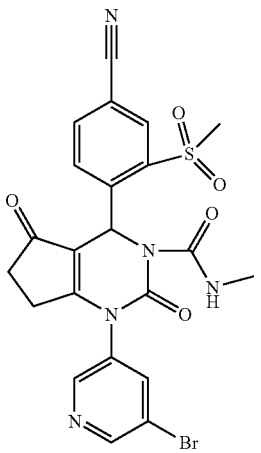 [SMILES: CNC(=O)N1C(=O)N(c2cncc(Br)c2)C2=C(C(=O)CC2)C1c1ccc(C#N)cc1S(C)(=O)=O] | 544 (bromine isotope pattern) | 0.92 | Z018_S04 |

TABLE 7-continued
| EXAMPLE | Starting Material | Structure | MS [M + H]+ | Retention time [min] | HPLC-Method |
|---|---|---|---|---|---|
| D.4.7 | EXAMPLE D.2.3 (ethyl amine instead of methyl amine) | 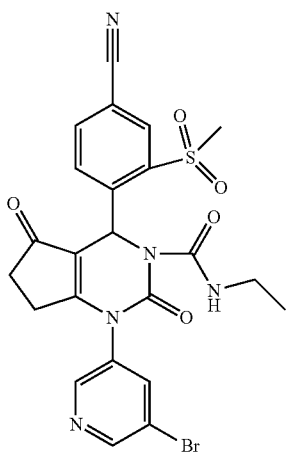 | 558 (bromine isotope pattern) | 0.96 | Z018_S04 |
| D.4.8 | EXAMPLE D.2.4 | 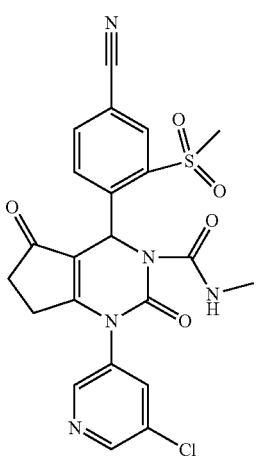 [SMILES: CNC(=O)N1C(=O)N(c2cncc(Cl)c2)C2=C(C(=O)CC2)C1c1ccc(C#N)cc1S(C)(=O)=O] | 500 (chlorine isotope pattern) | 0.88 | Z017_S04 |
| D.4.9 | EXAMPLE D.2.4 (ethyl amine instead of methyl amine) | 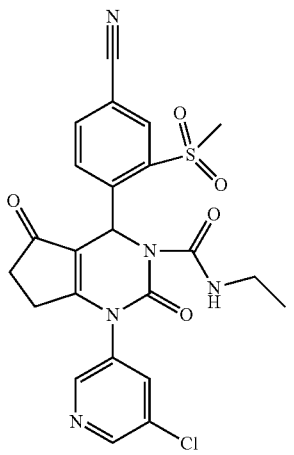 [SMILES: CCNC(=O)N1C(=O)N(c2cncc(Cl)c2)C2=C(C(=O)CC2)C1c1ccc(C#N)cc1S(C)(=O)=O] | 514 (chlorine isotope pattern) | 0.93 | Z017_S04 |

TABLE 7-continued

| EXAMPLE | Starting Material | Structure | MS [M + H]+ | Retention time [min] | HPLC-Method |
|---|---|---|---|---|---|
| D.4.10* | INTER-MEDIATE D.6.A | (Enantiomer) | 548 | 1.00 | Z018_S04 |

*As the starting material INTERMEDIATE D.6.A is enantiopure, it is assumed that EXAMPLE D.4.10 is enantiopure and has the same configuration as the starting material.

Example D.4.1A and Example D.4.1B

Enantiomers of Example D.4.1

The enantiomers of racemic 4-(4-cyano-2-ethanesulfonyl-phenyl)-2,5-dioxo-1-(2-trifluoromethyl-pyridin-4-yl)-1,2,4,5,6,7-hexahydro-cyclopentapyrimidine-3-carboxylic acid ethylamide (EXAMPLE D.4.1, 127 mg, 0.226 mmol) are separated by preparative supercritical fluid chromatography on a chiral phase (Daicel Chiralpak IA, 10×250 mm, 5 μm, 25% MeOH in supercritical $CO_2$, 40° C., 120 bar back pressure).

Example D.4.1A

Yield 56 mg; ESI mass spectrum [M+H]+=562; Retention time: 1.51 min (early eluting enantiomer) (I_IA_25_MeOH_NH₃).

Example D.4.1B

Yield 54 mg; ESI mass spectrum [M+H]+=562; Retention time: 2.59 min (late eluting enantiomer) (I_IC_25_MeOH_NH₃).

Example D.5

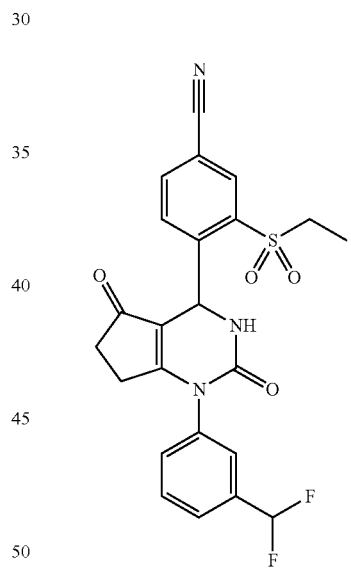

4-[1-(3-Difluoromethyl-phenyl)-2,5-dioxo-2,3,4,5,6,7-hexahydro-1H-cyclopentapyrimidin-4-yl]-3-ethanesulfonyl-benzonitrile Triethylamine (238 μL, 1.699 mmol) is added to a mixture of 4-{amino-[2-(3-difluoromethyl-phenylamino)-5-oxo-cyclopent-1-enyl]-methyl}-3-ethanesulfonyl-benzonitrile hydrochloride (INTERMEDIATE D.9, 1.516 g, purity 90%, 2.831 mmol) and 1,1'-carbonyldiimidazole (551 mg, 3.40 mmol) in acetonitrile (10 mL) and the mixture is stirred at room temperature overnight. The mixture is concentrated under reduced pressure and the residue is treated with water.

The precipitate is filtered and dried. Yield: 1.24 g. ESI mass spectrum: [M+H]$^+$=472; Retention time HPLC: 0.92 min (Z017_S04).

Example D.5A and Example D.5B

Enantiomers of Example D.5

The enantiomers of racemic 4-[1-(3-difluoromethyl-phenyl)-2,5-dioxo-2,3,4,5,6,7-hexahydro-1H-cyclopentapyrimidin-4-yl]-3-ethanesulfonyl-benzonitrile (EXAMPLE D.5, 490 mg, 1.04 mmol) are separated by preparative supercritical fluid chromatography on a chiral phase (Lux C1, 20×250 mm, 5 μm, MeOH, 21 mL/min flow rate).

Example D.5A

Yield 262 mg; ESI mass spectrum [M+H]$^+$=472; Retention time: 2.95 min (early eluting enantiomer) (I_IB_20_MeOH_NH$_3$).

Example D.5B

Yield 223 mg; ESI mass spectrum [M+H]$^+$=472; Retention time: 3.66 min (late eluting enantiomer) (I_IB_20_MeOH_NH$_3$).

Example D.6

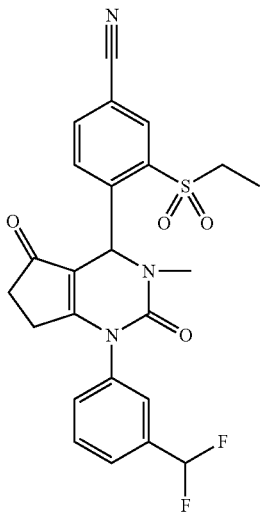 [SMILES: CCS(=O)(=O)c1cc(C#N)ccc1C1C2=C(CCC2=O)N(c2cccc(C(F)F)c2)C(=O)N1C]

4-[1-(3-Difluoromethyl-phenyl)-3-methyl-2,5-dioxo-2,3,4,5,6,7-hexahydro-1H-cyclopentapyrimidin-4-yl]-3-ethanesulfonyl-benzonitrile Methyliodide (20 μL, 0.32 mmol) is added to a mixture of 4-[1-(3-difluoromethyl-phenyl)-2,5-dioxo-2,3,4,5,6,7-hexahydro-1H-cyclopentapyrimidin-4-yl]-3-ethanesulfonyl-benzonitrile (EXAMPLE D.5, 50 mg, 0.106 mmol) and cesium carbonate (69 mg, 0.212 mmol) in DMF (1 mL), and the mixture is stirred at room temperature overnight. The reaction mixture is purified by reversed phase HPLC (Waters SunFire™-C$_{18}$, gradient of is acetonitrile in water, 0.1% TFA). Yield: 36 mg; ESI mass spectrum [M+H]$^+$=486; Retention time HPLC: 0.79 min (005_CA01).

Example D.7

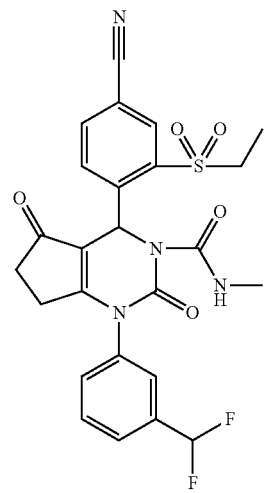 [SMILES: CCS(=O)(=O)c1cc(C#N)ccc1C1C2=C(CCC2=O)N(c2cccc(C(F)F)c2)C(=O)N1C(=O)NC]

4-(4-Cyano-2-ethanesulfonyl-phenyl)-1-(3-difluoromethyl-phenyl)-2,5-dioxo-1,2,4,5,6,7-hexahydrocyclopentapyrimidine-3-carboxylic acid methylamide 4-Nitrophenylchloroformate (23 mg; 0.12 mmol) is added to a mixture of 4-[1-(3-difluoromethyl-phenyl)-2,5-dioxo-2,3,4,5,6,7-hexahydro-1H-cyclopentapyrimidin-4-yl]-3-ethanesulfonyl-benzonitrile (EXAMPLE D.5; 50 mg; 0.106 mmol), DIPEA (72 μL; 0.42 mmol) and 4-dimethylaminopyridine (14 mg; 0.12 mmol) in acetonitrile (1 mL) and the mixture is stirred at room temperature for 2 h. 4-Nitrophenylchloroformate (23 mg; 0.12 mmol) is added and the reaction is stirred 1 h. Methylamine (2M in THF, 159 μL; 0.318 mmol) is added to the mixture containing the 4-nitrophenyl carbamate intermediate and the mixture stirred at room temperature for 1 h. The reaction mixture is purified by reversed phase HPLC (Stablebond, gradient of acetonitrile in water, 0.1% TFA). Yield: 32 mg; ESI mass spectrum [M+H]+=529; Retention time HPLC 0.98 min (Z017_S04).

Example E.1

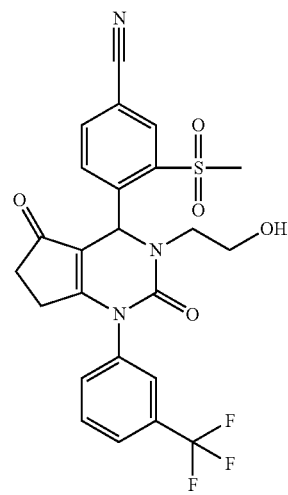 [SMILES: CS(=O)(=O)c1cc(C#N)ccc1C1C2=C(CCC2=O)N(c2cccc(C(F)(F)F)c2)C(=O)N1CCO]

4-[3-(2-Hydroxy-ethyl)-2,5-dioxo-1-(3-trifluorom-
ethyl-phenyl)-2,3,4,5,6,7-hexahydro-1H-cyclopen-
tapyrimidin-4-yl]-3-methanesulfonyl-benzonitrile Acetic acid 2-[4-(4-cyano-2-methanesulfonyl-phenyl)-2,5-dioxo-1-(3-trifluoromethyl-phenyl)-1,2,4,5,6,7-hexahydro-cyclopentapyrimidin-3-yl]-ethyl ester (INTERMEDIATE E.4, 40 mg, 0.071 mmol) is stirred with trifluoroacetic acid (2.0 mL, 26 mmol) at 60° C. overnight and the mixture is concentrated under reduced pressure. The residue is stirred with acetonitrile and water for 2 h (→hydrolysis of trifluoroacetic acid ester) and then to purified by reversed phase HPLC (Waters SunFire™-C$_{18}$, gradient of acetonitrile in water, 0.1% TFA). Yield: 17 mg; ESI mass spectrum [M+H]$^+$=520; Retention time HPLC: 0.96 min (Z018_S04).

Example E.2

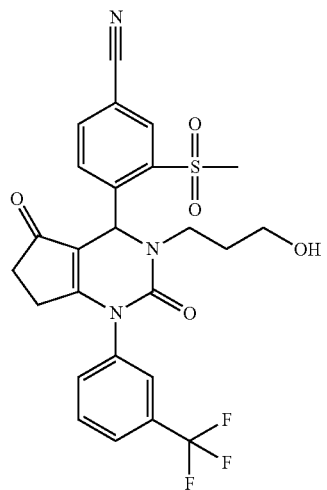

(Enantiomer)

4-[3-(3-Hydroxy-propyl)-2,5-dioxo-1-(3-trifluorom-
ethyl-phenyl)-2,3,4,5,6,7-hexahydro-1H-cyclopen-
tapyrimidin-4-yl]-3-methanesulfonyl-benzonitrile To a mixture of 4-(2,5-dioxo-1-(3-(trifluoromethyl)phenyl)-2,3,4,5,6,7-hexahydro-1H-cyclopentapyrimidin-4-yl)-3-(methylsulfonyl)benzonitrile (INTERMEDIATE E.3A, early eluting enantiomer, 150 mg, 0.32 mmol) and cesium carbonate (206 mg, 0.63 mmol) in DMF (2.0 mL) is added 3-bromo-1-propanol (55 µL, 0.63 mmol) and the mixture is stirred at 50° C. overnight. The reaction mixture is treated with ice water, acidified with trifluoroacetic acid and purified by reversed phase HPLC (Waters SunFire™-C$_{18}$, gradient of acetonitrile in water, 0.1% TFA). Yield: 40 mg; ESI mass spectrum [M+H]$^+$=534; Retention time HPLC: 0.97 min (Z018_S04). As the starting material is enantiopure, it is assumed that EXAMPLE E.2 is enantiopure and has the same configuration as the starting material.

Example E.3

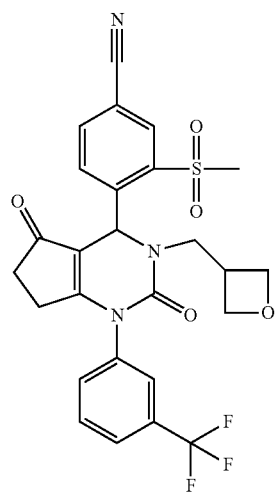 [SMILES: CS(=O)(=O)c1cc(C#N)ccc1C1C2=C(CCC2=O)N(c2cccc(C(F)(F)F)c2)C(=O)N1CC1COC1]

3-Methanesulfonyl-4-[3-oxetan-3-ylmethyl-2,5-di-
oxo-1-(3-trifluoromethyl-phenyl)-2,3,4,5,6,7-hexa-
hydro-1H-cyclopentapyrimidin-4-yl]-benzonitrile To a mixture of 4-(2,5-dioxo-1-(3-(trifluoromethyl)phenyl)-2,3,4,5,6,7-hexahydro-1H-cyclopentapyrimidin-4-yl)-3-(methylsulfonyl)benzonitrile (INTERMEDIATE E.3, 150 mg, 0.32 mmol) and cesium carbonate (206 mg, 0.63 mmol) in DMF (2.0 mL) is added 3-bromomethyl-oxetane (95 mg, 0.63 mmol) and the mixture is stirred at 50° C. overnight. The reaction mixture is treated with ice water, acidified with trifluoroacetic acid and purified by to reversed phase HPLC (Waters SunFire™-C$_{18}$, gradient of acetonitrile in water, 0.1% TFA).
Yield: 55 mg; ESI mass spectrum [M+H]$^+$=546; Retention time HPLC: 1.01 min (Z018_S04).

Example E.3A and Example E.3B

Enantiomers of Example E.3

The enantiomers of racemic 3-methanesulfonyl-4-[3-oxetan-3-ylmethyl-2,5-dioxo-1-(3-trifluoromethyl-phenyl)-2,3,4,5,6,7-hexahydro-1H-cyclopentapyrimidin-4-yl]-benzonitrile (EXAMPLE E.3, 55 mg, 0.065 mmol) are separated by preparative supercritical fluid chromatography on a chiral phase (Daicel Chiralpak IC, 10×250 mm, 5 µm, 30% MeOH+20 mM NH$_3$ in supercritical CO$_2$, 40° C., 120 bar back pressure).

Example E.3A

Yield 11 mg; ESI mass spectrum [M+H]$^+$=546; Retention time: 4.12 min (early eluting enantiomer) (I_IC_30_MeOH_NH$_3$).

Example E.3B

Yield 11 mg; ESI mass spectrum [M+H]$^+$=546; Retention time: 4.66 min (late eluting enantiomer) (I_IC_30_MeOH_NH$_3$).

Pharmacological Data

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: I-1270). All other materials were of the highest grade commercially available.

The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 µL of these compound dilutions were mixed with 10 µl Neutrophil elastase (9 ng/ml in assay buffer) in a black 384 well OptiPlate (Perkin Elmer, Cat No.: 6007270) and incubated for 15 min at room temperature. Subsequently 10 µL substrate solution in assay buffer were added (250 µM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). $IC_{50}$ values were estimated using a sigmoidal concentration response curve with variable slope. Means of low values were taken as 0%, means of high values as 100%. The $IC_{50}$ values of selected compounds in the Neutrophil Elastase assay are listed in Table 8.

TABLE 8

| Example | $IC_{50}$ [nM] |
|---|---|
| A.1 | 1.6 |
| A.1A | <1 |
| A.1B | 2780 |
| A.2 | <1 |
| A.3 | <1 |
| B.1 | 2.1 |
| B.1.1 | 5.7 |
| B.1.2A | 224 |
| B.1.2B | <1 |
| B.1.3A | <1 |
| B.1.3B | 11 |
| B.1.4 | <1 |
| C.1A | 1825 |
| C.1B | <1 |
| C.2A | <1 |
| C.2B | 13 |
| C.3 | <1 |
| C.4.1 | 5.2 |
| C.4.2 | 8.9 |
| C.5.1 | 1.9 |
| C.5.2 | 1.9 |
| C.6.1 | <1 |
| C.6.2 | <1 |
| D.1A | 2.6 |
| D.1B | 19 |
| D.2 | 24 |
| D.2.1 | 60 |
| D.2.2 | 65 |
| D.2.3 | 101 |
| D.2.4 | 103 |
| D.3 | 4.0 |
| D.3A | 2810 |
| D.3B | 1.4 |
| D.3.1 | 8.8 |
| D.3.2 | 9.5 |
| D.3.3 | 13 |
| D.3.4 | 8.1 |
| D.4 | <1 |
| D.4.1 | <1 |
| D.4.1A | <1 |
| D.4.1B | 338 |
| D.4.2 | <1 |
| D.4.3 | <1 |
| D.4.4 | <1 |
| D.4.5 | <1 |
| D.4.6 | 1.2 |
| D.4.7 | <1 |
| D.4.8 | <1 |
| D.4.9 | <1 |
| D.4.10 | <1 |
| D.5 | 5.5 |
| D.5A | 2.2 |
| D.5B | 892 |
| D.6 | <1 |
| D.7 | <1 |
| E.1 | <1 |
| E.2 | <1 |
| E.3A | <1 |
| E.3B | 106 |

Assay for the Determination of Neutrophil Elastase Inhibitory Activity in Human Plasma Citrated blood from human healthy donors is mixed with zymosan suspension and incubated at room temperature. This leads to the stimulation of neutrophils and the release of neutrophil elastase into the plasma. The stimulated blood is centrifuged to generate the neutrophil elastase enriched plasma.

Preparation of Zymosan Working Solution:

Zymosan (100 mg) is mixed with saline (0.9%, 10 mL) and stored at 4° C. for up to one week (note: zymosan does not dissolve in the saline and is used as a suspension).

Whole Blood Stimulation:

A single 45 ml blood sample is taken into a 50 ml tube containing citrate (3.13%, 5 mL) and the tube is gently inverted 4 times.

Immediately after blood sampling, zymosan working solution (5 mL) is added.

After the addition of zymosan working solution, the tubes are capped, mixed gently and incubated at 22° C. for 15 min on a shaker at 20 rpm.

Make 10 ml aliquots after the incubation time.

Centrifuge the 15 ml tubes at 800 g for 15 min at 4° C. in a Jouan centrifuge.

Harvest the plasma and make 1-5 ml aliquots.

Store the plasma at −80° C.

Various concentrations of the neutrophil elastase inhibitor are incubated with plasma. Subsequently, the enzyme activity is measured using the fluorogenic substrate MeOSuc-Ala-Ala-Pro-Val-AMC (Bachem Cat. No. I-1270, substrate concentration: 250 µM, pH 7.5, 25 mM TRIS buffer, 250 mM NaCl) in analogous fashion as described for the human neutrophil assay. A dose response curve is generated to calculate the $EC_{50}$ of the inhibitor. The analysis of the data is performed by the calculation of the percentage of fluorescence in the presence of the test compound compared to the fluorescence of the vehicle control after subtracting the background fluorescence: An inhibitor of the neutrophil elastase enzyme will give values between 100% control (no inhibition) and 0% control (complete inhibition).

The $EC_{50}$ values of selected compounds in the human plasma assay described above are listed in Table 9.

TABLE 9

| Example | $EC_{50}$ [μM] |
|---|---|
| A.1A | 0.002 |
| A.2 | 0.001 |
| A.3 | 0.001 |
| B.1.2B | 0.001 |
| B.1.3A | 0.001 |
| C.1B | 0.001 |
| C.2A | 0.002 |
| C.5.1 | 0.002 |
| C.5.2 | 0.001 |
| D.1A | 0.001 |
| D.3B | 0.001 |
| D.4.1A | <0.001 |
| D.4.4 | 0.002 |
| D.4.5 | 0.001 |
| D.5A | 0.001 |

Assay for the Determination of Metabolic Stability with Human Liver Microsomes

The metabolic degradation of the test compound is assayed at 37° C. with pooled human liver microsomes. The final incubation volume of 100 μl per time point contains TRIS buffer pH 7.6 (0.1 M), magnesium chloride (5 mM), microsomal protein (1 mg/ml) and the test compound at a final concentration of 1 μM. Following a short preincubation period at 37° C., the reactions are initiated by addition of beta-nicotinamide adenine dinucleotide phosphate, reduced form (NADPH, 1 mM) and terminated by transferring an aliquot into acetonitrile after different time points. Additionally, the NADPH-independent degradation is monitored in incubations without NADPH, terminated at the last time point. The [%] remaining test compound after NADPH independent incubation is reflected by the parameter c(control) (metabolic stability). The quenched incubations are pelleted by centrifugation (10'000 g, 5 min). An aliquot of the supernatant is assayed by LC-MS/MS for the amount of parent compound.

The half-life ($t_{1/2}$ INVITRO) is determined by the slope of the semilogarithmic plot of the concentration-time profile. The intrinsic clearance (CL_INTRINSIC) is calculated by considering the amount of protein in the incubation:

CL_INTRINSIC [μl/min/mg protein]=(ln 2/(half-life [min]*protein content [mg/ml]))*1'000.

The half-life ($t_{1/2}$ INVITRO) values of selected compounds in the metabolic stability assay described above are listed in Table 10.

TABLE 10

| Example | $t_{1/2}$ INVITRO [min] |
|---|---|
| A.2 | >130 |
| A.3 | >130 |
| B.1.2B | >130 |
| B.1.3A | 91 |
| C.1B | 93 |
| C.2A | >130 |
| C.5.1 | 110 |
| C.5.2 | >130 |
| D.1A | >130 |
| D.3B | 120 |

TABLE 10-continued

| Example | $t_{1/2}$ INVITRO [min] |
|---|---|
| D.4.1A | >130 |
| D.4.4 | >130 |
| D.4.5 | >130 |
| D.5A | >130 |

Assay for the Determination of Metabolic Stability with Human Hepatocytes

The metabolic degradation of the test compound is assayed in a human hepatocyte suspension. Human hepatocytes (typically cryopreserved) are incubated in an appropriate buffer system (e.g. Dulbecco's modified eagle medium plus 3.5 g glucagon/500 mL, 2.5 mg insulin/500 mL and 3.75 mg/500 mL hydrocortison) containing 5% species serum. Following a (typically) 30 min preincubation in an incubator (37° C., 10% $CO_2$), 5 μl of test compound solution (80 μM; from 2 mM stock solution in DMSO diluted 1:25 with medium) are added into 395 μl hepatocyte suspension (cell density in the range 0.25-5*$10^6$ cells/mL, typically 1*$10^6$ cells/mL; final concentration of test compound 1 μM, final DMSO concentration 0.05%). The cells are incubated for six hours (incubator, orbital shaker) and samples (25 μl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended. The decline of parent compound is analyzed by LC-MS/MS.

The intrinsic clearance CL_INTRINSIC is calculated as follows:

CL_INTRINSIC=Dose/AUC=($C_0$/CD)/
(AUD+$c_{last}$/k)*1'000/60

($C_0$: initial concentration in the incubation [M], CD: cell density of vital cells [$10^6$ cells/mL], AUD: area under the data [μM*h], $c_{last}$: concentration of last data point [μM], k: slope of the regression line for parent decline [$h^{-1}$])

The calculated in vitro hepatic intrinsic clearance can be scaled up to the intrinsic in vivo hepatic clearance and used to predict hepatic in vivo blood clearance (CL) by the use of a liver model (well stirred model):

CL_INTRINSIC_INVIVO [ml/min/kg]=(CL_INTRINSIC [μL/min/$10^6$ cells]*hepatocellularity [$10^6$ cells/g liver]*liver factor [g/kg bodyweight])/1'000

CL [ml/min/kg]=CL_INTRINSIC_INVIVO [ml/min/kg]*hepatic blood flow [ml/min/kg]/(CL_INTRINSIC_INVIVO [ml/min/kg]+hepatic blood flow [ml/min/kg])

$Q_h$ [%]=CL [ml/min/kg]/hepatic blood flow [ml/min/kg])

(Hepatocellularity, human: 120*$10^6$ cells/g liver; liver factor, human: 25.7 g/kg bodyweight; blood flow, human: 21 ml/(min*kg))

Based on this assay, Example C.2A exhibits a predicted hepatic in vivo blood clearance of 3% human hepatic blood flow.

Assay for Determination of Drug Transport Across Human Caco-2 Cells

The assay provides information on the potential of a compound to pass the cell membrane, on the extent of oral absorption as well as on whether the compound is actively transported by uptake and/or efflux transporters. For the measurement of permeability across polarized, confluent human cancer colon carcinoma cells 2 (Caco-2) cell monolayers grown on permeable filter supports are used as the in vitro absorption model.

Apparent permeability coefficients (PE) of the compounds across the Caco-2 monolayers are measured (pH 7.2, 37° C.) in apical-to-basal (AB) (absorptive) and basal-to-apical (BA) (secretory) transport direction. AB permeability (PEAB) represents drug absorption from the intestine into the blood and BA permeability (PEBA) drug secretion from the blood back into the intestine via both passive permeability as well as active transport mechanisms mediated by efflux and uptake transporters that are expressed on the Caco-2 cells. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB suggests the involvement of an apical efflux transporter (like P-gp) and/or basolateral uptake transporter; higher PEAB than PEBA permeability suggests involvement of an apical uptake transporter (like PepT1) and/or basolateral efflux transporter (like MRP3). Active transport is concentration-dependently saturable.

Caco-2 cells ($1$-$2*10^5$ cells/cm$^2$ area) are seeded on filter inserts (Costar transwell polycarbonate or PET filters, 0.4 µm pore size) and cultured (DMEM) for 10 to 25 days. Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$x7H$_2$O, 0.41 mM NaH$_2$PO$_4$xH$_2$O, 15 mM HEPES, 20 mM glucose, pH 7.2) to prepare the transport solutions (typically 10 µM compound, final DMSO <=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by LC-MS/MS or scintillation counting. Sampled receiver volumes are replaced with fresh receiver solution.

The apparent permeability coefficients (PEAB and PEBA) of selected compounds in the Caco-2 drug transport assay described above are listed in Table 11.

TABLE 11

| Example | PEAB [cm/s] | PEBA [cm/s] |
| --- | --- | --- |
| A.1A | 0.000053 | 0.000098 |
| A.2 | 0.000092 | 0.000080 |
| A.3 | 0.000067 | 0.000087 |
| B.1.2B | 0.000012 | 0.000120 |
| B.1.3A | 0.0000099 | 0.000130 |
| C.1B | 0.0000037 | 0.000041 |
| C.2A | 0.000013 | 0.000073 |
| C.5.1 | 0.0000071 | 0.000057 |
| C.5.2 | 0.000016 | 0.000082 |
| D.1A | 0.000019 | 0.000081 |
| D.3B | 0.000021 | 0.000085 |
| D.4.1A | 0.0000036 | 0.000061 |
| D.4.4 | 0.0000031 | 0.000060 |
| D.4.5 | 0.0000073 | 0.000067 |
| D.5A | 0.0000075 | 0.000078 |

Assay for Determination of Aqueous Solubility ("High Throughput Method")

The aqueous solubility of a compound is determined by comparing the amount dissolved in aqueous buffer (containing 2.5% DMSO) to the amount dissolved in an acetonitrile/water (1/1) solution. Starting from a 10 mM DMSO stock solution, aliquots are diluted with acetonitrile/water (1/1) and McIlvaine buffer pH 6.8, respectively. After 24 h of shaking, the solutions or suspensions are filtered and analyzed by LC-UV. The amount dissolved in buffer is compared to the amount dissolved in the acetonitrile/water (1/1) solution. Solubility is measured from 0.001 to 0.125 mg/ml at a DMSO concentration of 2.5%. If more than 90% of the compound is dissolved in buffer, the value is marked with ">".

The aqueous solubility of selected compounds in the solubility assay described above is listed in Table 12.

TABLE 12

| Example | Aqueous solubility [mg/mL] |
| --- | --- |
| A.1A | 0.058 |
| A.3 | 0.065 |
| B.1.2B | 0.073 |
| B.1.3A | 0.093 |
| C.1B | 0.061 |
| C.2A | 0.058 |
| C.5.1 | 0.086 |
| C.5.2 | 0.069 |
| D.4.1A | 0.081 |
| D.4.5 | 0.078 |
| D.5A | 0.067 |

Assay for Determination of Aqueous Solubility ("Shaked Flask Method")

Saturated solutions are prepared in well plates by adding an appropriate volume of selected aqueous media (typically in the range of 0.25-1.5 ml) into each well which contains a known quantity of solid drug substance (typically in the range 0.5-5.0 mg). The wells are shaken or stirred for a predefined time period (typically in a range of 2-24 h) and then filtered using appropriate filter membranes (typically PTFE-filters with 0.45 µm pore size). Filter absorption is avoided by discarding the first few drops of filtrate. The amount of dissolved drug substance is determined by UV spectroscopy or by HPLC with UV-detection. In addition, the pH of the aqueous saturated solution is measured using a glass-electrode pH meter. The examples in Table 12 exhibit a solubility of >0.01 mg/mL at pH 6.8 (McIlvaine buffer) in this solubility assay.

Assay for Determination of Cytochrome P450 2C9 Inhibition

The inhibition of cytochrome P450 2C9-isoenzyme catalysed hydroxylation of Diclofenac by the test compound is assayed at 37° C. with human liver microsomes. All assays are carried out on a robotic system in 96 well plates. The final incubation volume contains TRIS buffer (0.1 M), MgCl$_2$ (5 mM), human liver microsomes (0.1 mg/ml), Diclofenac (10 M) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC$_{50}$ of a positive control inhibitor (sulfaphenazole) is determined. Experimental IC$_{50}$ values are calculated by least square regression according to the following equation:

% control activity=(100% control activity/(1+(I/IC$_{50}$)*S))–B (I=inhibitor concentration, S=slope factor, B=background activity)

If the inhibition of the reaction is already >50% at the lowest concentration of the test compound, the IC$_{50}$ is assigned "<lowest concentration tested" (usually <0.4 μM). If the inhibition of the reaction is still <50% at the highest concentration of the test compound, the IC$_{50}$ is assigned "> highest concentration tested" (usually >50 μM). Example A.1A, Example B.1.2B and Example C.2A exhibit IC$_{50}$ values >50 μM in this assay.

Assay for Determination of Cytochrome P450 2C19 Inhibition

The inhibition of cytochrome P450 2C19-isoenzyme catalysed hydroxylation of Mephenytoin by the test compound is assayed at 37° C. with human liver microsomes. All assays are carried out on a robotic system in 96 well plates. The final incubation volume contains TRIS buffer (0.1 M), MgCl$_2$ (5 mM), human liver microsomes (0.5 mg/ml), (S)-Mephenytoin (70 μM) and the test compound at five different concentrations or no compound (high control) in duplicate (e.g. highest concentration 10-50 μM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC$_{50}$ of a positive control inhibitor (tranylcypromine) is determined. Experimental IC$_{50}$ values are calculated by least square regression according to the following equation:

% control activity=(100% control activity/(1+(I/IC$_{50}$)*S))–B (I=inhibitor concentration, S=slope factor, B=background activity)

If the inhibition of the reaction is already >50% at the lowest concentration of the test compound, the IC$_{50}$ is assigned "<lowest concentration tested" (usually <0.4 μM). If the inhibition of the reaction is still <50% at the highest concentration of the test compound, the IC$_{50}$ is assigned "> highest concentration tested" (usually >50 μM). Example A.1A, Example B.1.2B and Example C.2A exhibit IC$_{50}$ values >50 μM in this assay.

Assay for Determination of Cytochrome P450 2C8 Inhibition

The inhibition of cytochrome P450 2C8-isoenzyme catalysed deethylation of Amodiaquine by the test compound is assayed at 37° C. with human liver microsomes. All assays are carried out on a robotic system in 96 well plates. The final incubation volume contains TRIS buffer (0.1 M), MgCl$_2$ (5 mM), human liver microsomes (0.05 mg/ml), Amodiaquine (1 μM) and the test compound at five different concentrations or no compound (high control) in duplicate (e.g. highest concentration 10-50 μM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC$_{50}$ of a positive control inhibitor (Montelukast) is determined. Experimental IC$_{50}$ values are calculated by least square regression according to the following equation:

% control activity=(100% control activity/(1+(I/IC$_{50}$)*S))–B (I=inhibitor concentration, S=slope factor, B=background activity)

If the inhibition of the reaction is already >50% at the lowest concentration of the test compound, the IC$_{50}$ is assigned "<lowest concentration tested" (usually <0.4 μM). If the inhibition of the reaction is still <50% at the highest concentration of the test compound, the IC$_{50}$ is assigned "> highest concentration tested" (usually >50 μM). Example A.1A, Example B.1.2B and Example C.2A exhibit IC$_{50}$ values >50 μM in this assay.

Assay for Determination of Cytochrome P450 Induction

To assess induction of metabolizing enzyme CYP3A4, cryopreserved HepaRG® cells are seeded at a density of 1.0×105 per 96 well. Cells are allowed to equilibrate for 72 hours prior to exposure of 10 μM test article for 48 hours with renewal of test article every 24 hours. Known prototypical CYP3A4 inducers Rifampicin is used as a positive control at a concentration of 25 μM. After 48 hours of exposure, medium containing the test article is removed and cells were washed with phosphate buffered saline (PBS) prior to mRNA isolation.

Calculations:

Fold induction=(Enzyme mRNA Compound)/(Enzyme mRNA Solvent Control)

Inducer Potency=(Fold Compound)/(Fold Rifampicin)*100

Assay for Determination of hERG Inhibition

The inhibition of the hERG (human ether-a-go-go-related gene) potassium channel can be determined as described in Rast, G., & Guth, B. D., Journal of Pharmacological and Toxicological Methods (2014), http://dx.doi.org/10.1016/i.vascn.2014.08.001. The hERG inhibition of selected compounds in this patch clamp assay is listed in Table 13.

TABLE 13

| Example | hERG inhibition |
| --- | --- |
| A.1A | IC$_{50}$ > 30 μM (7% at 10 μM) |
| B.1.2B | IC$_{50}$ > 30 μM (12% at 10 μM) |
| C.2A | IC$_{50}$ > 30 μM (7% at 10 μM) |
| D.1A | IC$_{50}$ > 30 μM (8% at 10 μM) |

Combinations

The compounds of general formula 1 may be used on their own or combined with other active substances of formula 1 according to the invention. The compounds of general formula 1 may optionally also be combined with other pharmacologically active substances. These include, 12-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors, non-steroidale anti-inflammatory agents (NSAIDs), Cathepsin C (or DPPI/Dipeptidylaminopeptidase I) inhibitors, CRTH2 antagonists, DP1-receptor modulators, Thromboxane receptor antagonists, CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, CXCR3 antagonists, CXCR4 antagonists, CXCR2 antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergicreceptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immuno-therapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, that is:

Betamimetics with corticosteroids, PDE4-inhibitors, CRTH2-inhibitors or LTD4-antagonists,
Anticholinergics with betamimetics, corticosteroids, PDE4-inhibitors, CRTH2-inhibitors or LTD4-antagonists,
Corticosteroids with PDE4-inhibitors, CRTH2-inhibitors or LTD4-antagonists
PDE4-inhibitors with CRTH2-inhibitors or LTD4-antagonists
CRTH2-inhibitors with LTD4-antagonists.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury; acute respiratory distress syndrome;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, Candida, aspergillus, cryptococcal meningitis, Pneumocystis carnii, cryptosporidiosis, histoplasmosis, toxoplasmosis, trypanosome infection and leishmaniasis and, 9. other diseases: traumatic brain injury, abdominal aortic aneurism The present invention is directed to compounds of general formula 1 which are useful in the prevention and/or treatment of a disease and/or condition wherein the activity of inhibitors of neutrophil elastase is of therapeutic benefit, including but not limited to the treatment and/or prevention of asthma and allergic diseases, gastrointestinal inflammatory diseases, glomerulonephritis, eosinophilic diseases, chronic obstructive pulmonary disease, infection by pathogenic microbes, rheumatoid arthritis, neutrophilic diseases, cystic fibrosis (CF), non-cystic fibrosis, idiopathic pulmonary fibrosis, bronchiectasis, ANCA-associated vasculitis, lung cancer, non-cyctic fibrosis bronchiectasis, emphysema, chronic bronchitis, acute lung injury (ALI), acute respiratory distress syndrome (ARDS), pulmonary hypertension, pulmonary arterial hypertension (PAH), Alpha-1-antitrypsin deficiency (AATD), obesity and related inflammation, e.g. chronic adipose tissue inflammation, adipose inflammation, high-fat diet induced inflammation, insulin resistance, diabetes, fatty liver and liver steatosis.

A correlation between the biological activity and the medical indications is described in the literature e.g. "Henriksen, P. A. Current Opinion in Hematology (2014), 21(1), 23-28" Accordingly, the present invention relates to a compound of general formula 1 as a medicament.

In a further aspect of the present invention the present invention relates to methods for the treatment or prevention of above mentioned diseases and conditions, which method comprises the administration of an effective amount of a compound of general formula 1 to a human being.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon a patient's unique condition.

| LIST OF ABBREVIATIONS | |
|---|---|
| ACN | acetonitrile |
| aq. | aqueous |
| BOC | tert.-butyloxycarbonyl-- |
| d | day |
| DCM | dichloromethane |
| DEA | diethylamine |
| DIPEA | N,N-diisopropylethylamine |
| DIPE | diisopropyl ether |
| DMAP | 4-dimethylaminopyridine |
| DMF | N,N-dimethylformamide |
| DMSO | dimethyl sulfoxide |
| EA | ethyl acetate |
| FA | formic acid |
| h | hour |
| HATU | O-(7-azabenzotriazol-1-yl)-N,N,N',N'-tetramethyluronium hexafluorophosphate |
| LiOH | lithium hydroxide |
| MeOH | methanol |
| MeTHF | 2-methyltetrahydrofuran |
| NaH | sodium hydride |
| PE | petrol ether |
| RT, r.t. | room temperature |
| rt | retention time |
| TBME | tert-butyl methyl ether |
| TBTU | o-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | toluene sulfonic acid |

What we claim:

1. A compound of formula 1

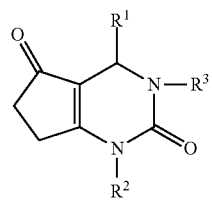

wherein
R¹ is
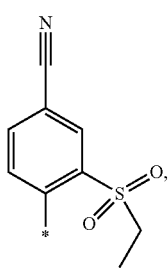
R² is
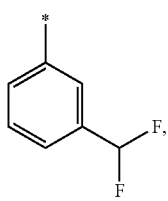
and R³ is H;
or
R¹ is
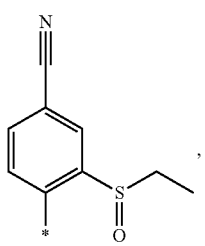 [SMILES: *c1ccc(C#N)cc1S(=O)CC]
R² is
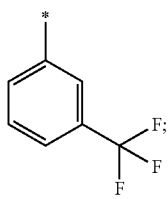
and R³ is CH₃;
or
R¹ is
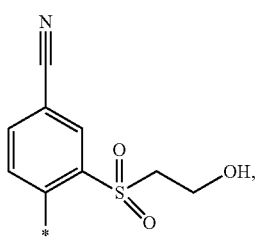
R² is
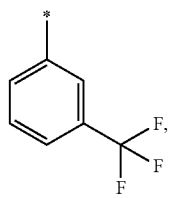 [SMILES: *c1cccc(C(F)(F)F)c1]
and R³ is CH₃;
wherein * indicates the point of attachment;
or a pharmaceutically acceptable salt thereof.
2. The compound according to claim 1, of formula 1.a
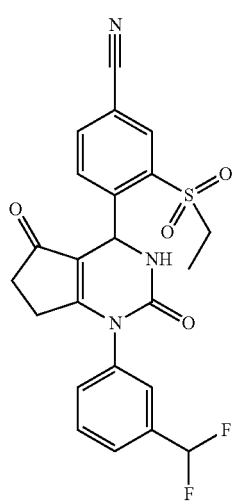
1.a
or a pharmaceutically acceptable salt thereof.
3. The compound according to claim 1, of formula 1.b
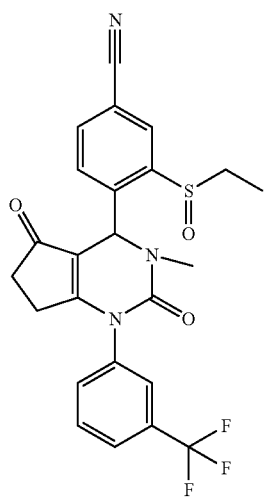
1.b
or a pharmaceutically acceptable salt thereof.

4. The compound according to claim 1, of formula 1.d

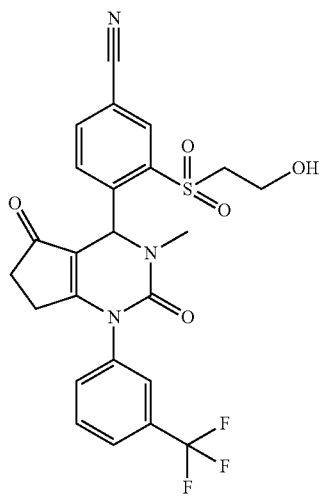

1.d or a pharmaceutically acceptable salt thereof.

5. The compound according to claim 1, wherein the configuration of formula 1 is formula 1'

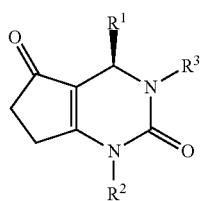

1' or a pharmaceutically acceptable salt thereof.

6. The compound according to claim 5, of formula 1.a'

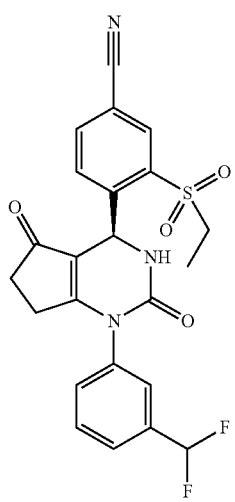

1.a' or a pharmaceutically acceptable salt thereof.

7. The compound according to claim 5, of formula 1.b'

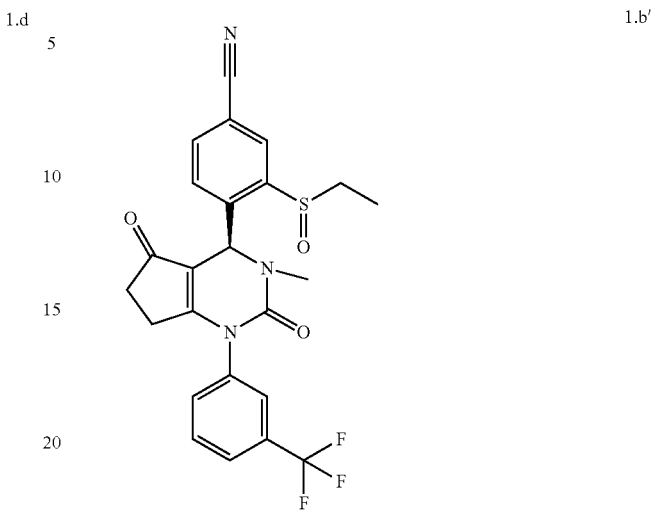

1.b' or a pharmaceutically acceptable salt thereof.

8. The compound according to claim 5, of formula 1.d'

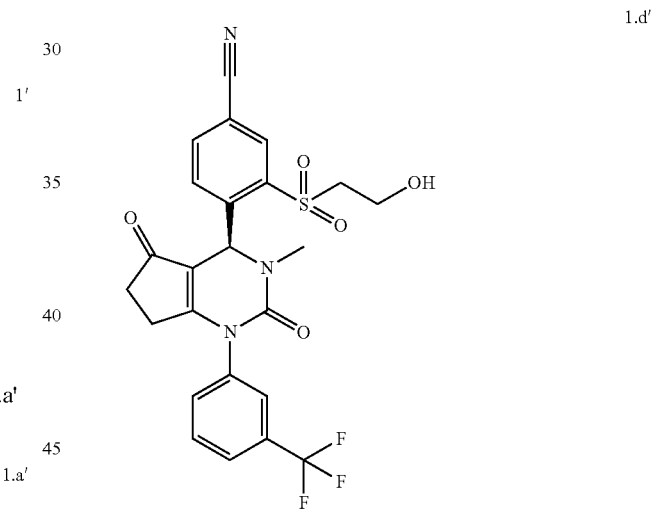

1.d' or a pharmaceutically acceptable salt thereof.

9. A pharmaceutical composition comprising a compound according to claim 1 and a pharmaceutically acceptable carrier.

10. A pharmaceutical composition comprising a compound according to claim 5 and a pharmaceutically acceptable carrier.

11. A method for the treatment of a disease associated with increased neutrophil elastase activity selected from chronic obstructive pulmonary disease (COPD), alpha-1-antitrypsin deficiency (AATD) and emphysema comprising administering a therapeutically effective amount of a compound according to claim 1 to a patient in need thereof.

12. The method according to claim 11 wherein the disease is chronic obstructive pulmonary disease (COPD).

13. A method for the treatment of a disease associated with increased neutrophil elastase activity selected from chronic obstructive pulmonary disease (COPD), alpha-1- antitrypsin deficiency (AATD) and emphysema comprising administering a therapeutically effective amount of a compound according to claim 5 to a patient in need thereof.

14. The method according to claim 13 wherein the disease is chronic obstructive pulmonary disease (COPD).

* * * * *